(12) United States Patent
Inagaki et al.

(10) Patent No.: US 8,420,764 B2
(45) Date of Patent: Apr. 16, 2013

(54) COMPOUND HAVING SILSESQUIOXANE SKELETON AND ITS POLYMER

(75) Inventors: Jyun-ichi Inagaki, Chiba (JP); Yasuyuki Sasada, Chiba (JP); Takashi Kato, Chiba (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 13/423,548

(22) Filed: Mar. 19, 2012

(65) Prior Publication Data

US 2012/0178894 A1 Jul. 12, 2012

Related U.S. Application Data

(60) Continuation of application No. 12/659,478, filed on Mar. 10, 2010, now Pat. No. 8,236,917, which is a division of application No. 11/704,253, filed on Feb. 9, 2007, now Pat. No. 7,705,105, which is a continuation of application No. 10/798,872, filed on Mar. 12, 2004, now abandoned.

(30) Foreign Application Priority Data

Mar. 13, 2003 (JP) ................................. 2003-067768
Apr. 18, 2003 (JP) ................................. 2003-114221
Feb. 27, 2004 (JP) ................................. 2004-53219

(51) Int. Cl.
*C08G 77/00* (2006.01)

(52) U.S. Cl.
USPC .......................................................... 528/43

(58) Field of Classification Search ...................... 528/43
See application file for complete search history.

(56) References Cited

U.S. PATENT DOCUMENTS

| | | |
|---|---|---|
| 6,750,308 B2 | 6/2004 | Andoh et al. |
| 6,767,930 B1 | 7/2004 | Svejda et al. |
| 6,770,724 B1 * | 8/2004 | Lichtenhan et al. ............ 528/14 |
| 6,927,270 B2 | 8/2005 | Lichtenhan et al. |
| 2004/0249103 A1 | 12/2004 | Morimoto et al. |

FOREIGN PATENT DOCUMENTS

WO 03/024870 3/2003

* cited by examiner

*Primary Examiner* — Kuo-Liang Peng
(74) *Attorney, Agent, or Firm* — Wenderoth, Lind & Ponack, L.L.P.

(57) ABSTRACT

A polymer having a structural unit represented by Formula (3):

(3)

[structural formula of silsesquioxane polymer showing Si-O cage with R$^1$ substituents and Q$^1$, Q$^2$, Q$^3$ groups]

wherein R$^1$ is phenyl in which any hydrogen may be replaced by halogen or alkyl having 1 to 5 carbon atoms; in the alkyl having 1 to 5 carbon atoms, any —CH$_2$—, which is not adjacent to each other, may be replaced by —O—, and any hydrogen may be replaced by halogen; Q$^1$ is hydrogen, halogen, alkyl having 1 to 10 carbon atoms, cyclopropyl, cyclobutyl, cyclopentyl, cyclohexyl, cyclohexenyl, or phenyl in which any hydrogen may be replaced by halogen or alkyl having 1 to 5 carbon atoms; in the alkyl having 1 to 10 carbon atoms and alkyl having 1 to 5 carbon atoms which is a substituent of phenyl, any —CH$_2$—, which is not adjacent to each other, may be replaced by —O—, —CH=CH— or —C≡C—, and any hydrogen may be replaced by halogen; and Q$^3$ is a group represented by Formula (4):

$$<\!\!-Z^0\!-\!(A^1\!-\!Z^1)_l\!-\!(A^2\!-\!Z^2)_m\!-\!(A^3\!-\!Z^3)_n\!-\!(A^4)_p\!-\!Z^5\!\!-\quad (4)$$

wherein a code < represents a bonding point with silicon; l, m, n and p are independently 0, 1, 2 or 3; and A$^1$, A$^2$, A$^3$, A$^4$, Z$^0$, Z$^1$, Z$^2$, Z$^3$ and Z$^5$ are as defined in claim 1.

10 Claims, No Drawings

COMPOUND HAVING SILSESQUIOXANE SKELETON AND ITS POLYMER

This application is a Continuation of U.S. application Ser. No. 12/659,478, filed Mar. 10, 2010, now U.S. Pat. No. 8,236, 917, which is a Divisional of U.S. application Ser. No. 11/704,253, filed Feb. 9, 2007, now U.S. Pat. No. 7,705,105, which is a Continuation of U.S. application Ser. No. 10/798, 872, filed Mar. 12, 2004, now abandoned.

FIELD OF THE INVENTION

The present invention relates to a compound having a silsesquioxane skeleton, a polymer obtained using the compound, and uses of the polymer.

BACKGROUND OF THE INVENTION

Polyorganosiloxane has excellent heat resistance, weatherability and surface-modifying function, and therefore it is used for semiconductor insulating protective films, flame retardants and coating material additives. For example, a coating agent prepared by blending an organic polymer with polyorganosiloxane can provide the surface of a material coated with the agent with functions such as water repellency. The representative examples of the organic polymer are acryl resins, polyurethanes and alkid resins. In general, however, these polymers do not have a good compatibility with polyorganosiloxane. Accordingly, there have been the problems that the coating agent is liable to become cloudy by blending polyorganosiloxane, and that a coating film obtained from the coating agent is liable to be whitened. That is, an addition amount of polyorganosiloxane has been restricted.

It has so far been known that an introduction of a polysiloxane structure into principal chain and/or side chain of an organic polymer makes it possible to improve the characteristics of the polymer such as heat resistance, water repellency and weatherability. Disclosed in, for example, the patent document 1 is a process in which a polysiloxane-containing polymer is radically copolymerized with other addition-polymerizable monomers to thereby produce a polysiloxane graft copolymer having a polysiloxane structure in a side chain. Polysilsesquioxane having a structure in which 1.5 oxygen atom is bonded to one silicon atom is disclosed in the patent document 2. It is described in the document that a polysilsesquioxane derivative having a polymerizable unsaturated bond and two or more functional groups such as hydroxyl group and alkoxy group is copolymerized with other addition-polymerizable monomers to thereby obtain a vinyl polymer into which a siloxane side chain is introduced. All of them are considered to be excellent in heat resistance, water repellency and weatherability as compared with the homopolymers of the other addition-polymerizable monomers.

It has so far been tried to enhance the content of a polyorganosiloxane structure in an organic polymer for the purpose of improving the characteristics as described above. However, in the foregoing organic polymer having a polyorganosiloxane structure, such a high improving effect as expected has not been provided to the characteristics such as heat resistance, water repellency, weatherability and electric insulating property. Accordingly, strongly desired is a polyorganosiloxane having a structure which further elevates characteristics such as heat resistance, water repellency and weatherability in the organic polymer.

Patent document 1: JP S60-231720 A/1985
Patent document 2: JP S62-275132 A/1987

An object of the present invention is to provide a useful polysilsesquioxane derivative in order to solve the problems described above, and another object is to provide a novel polymer obtained by using the derivative. Still another object is to provide a coating agent, a plastic substrate and an optical material each obtained by using the polymer.

SUMMARY OF THE INVENTION

First, terms and codes used in the present invention shall be explained. The term "optional" shows that not only the position but also the number are optional. For example, when "optional —$CH_2$— in alkyl may be replaced by —O— or —CH=CH—" is expressed, plural —$CH_2$— may be replaced by different groups respectively. Examples in such case are alkyl, alkoxy, alkoxyalkyl, alkoxyalkenyl and alkenyloxyalkyl. Alkyl and alkylene are used as groups including both of linear group and branched group unless otherwise described. The examples of halogen are fluorine, chlorine and bromine.

The present invention is constituted by the following items [1] to [40].

[1] A compound represented by Formula (1):

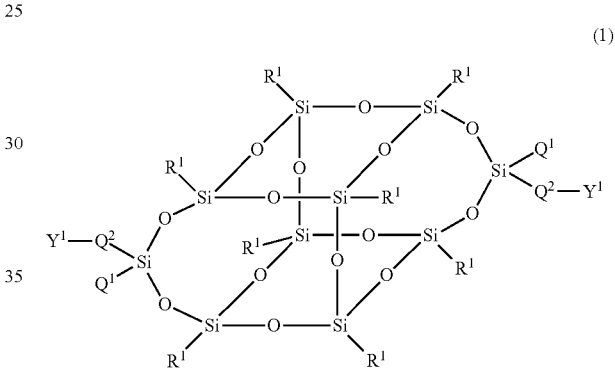

(1)

wherein $R^1$ is phenyl in which optional hydrogen may be replaced by halogen or alkyl having 1 to 5 carbon atoms; in the alkyl having 1 to 5 carbon atoms, optional —$CH_2$— which is not adjacent to each other may be replaced by —O—, and optional hydrogen may be replaced by halogen; $Q^1$ is hydrogen, halogen, alkyl having 1 to 10 carbon atoms, cyclopropyl, cyclobutyl, cyclopentyl, cyclohexyl, cyclohexenyl or phenyl in which optional hydrogen may be replaced by halogen or alkyl having 1 to 5 carbon atoms; in the alkyl having 1 to 10 carbon atoms and the alkyl having 1 to 5 carbon atoms which is a substituent of phenyl, optional —$CH_2$— which is not adjacent to each other may be replaced by —O—, —CH=CH— or —C≡C—, and optional hydrogen may be replaced by halogen; and $Q^2$ is a group represented by Formula (2):

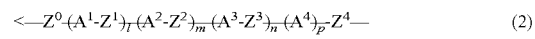

(2)

wherein the code < represents a bonding point with silicon; l, m, n and p are independently 0, 1, 2 or 3; $A^1$, $A^2$, $A^3$ and $A^4$ are independently a single bond, 1,4-cyclohexylene, 1,4-cyclohexenylene, a condensed ring group having 6 to 10 carbon atoms which is a divalent group, or 1,4-phenylene; in these rings, optional —$CH_2$— which is not adjacent to each other may be replaced by —O—, and optional —CH= may be replaced by —N=; optional hydrogen in all rings may be replaced by halogen, —CN, —$NO_2$ or alkyl having 1 to 5 carbon atoms; in the alkyl having 1 to 5 carbon atoms, optional —CH$_2$— which is not adjacent to each other may be replaced by —O—, —CH=CH— or —C≡C—, and optional hydrogen may be replaced by halogen; $Z^0$, $Z^1$, $Z^2$ and $Z^3$ are independently a single bond, —CH=CH—, —C≡C—, —COO—, —OCO—, or alkylene in which the number of carbon atoms is 1 to 20, and optional —CH$_2$— may be replaced by —O—, —S—, —NH—, —SiR$^2_2$—, —SiR$^2_2$O—, —OSiR$^2_2$—, —OSiR$^2_2$O—, —SiR$^2_2$OSiR$^2_2$—, —COO—, —OCO—, —CH=CH— or —C≡C—; $R^2$ is halogen, alkyl having 1 to 10 carbon atoms, cyclopropyl, cyclobutyl, cyclopentyl, cyclohexyl, cyclohexenyl, or phenyl in which optional hydrogen may be replaced by halogen, or alkyl having 1 to 5 carbon atoms; in the alkyl having 1 to 10 carbon atoms and the alkyl having 1 to 5 carbon atoms which is a substituent of phenyl, optional —CH$_2$— which is not adjacent to each other may be replaced by —O—, —CH=CH— or —C≡C—, and optional hydrogen may be replaced by halogen; $Z^4$ is a single bond, —CH=CH—, —C≡C—, —COO—, —OCO—, or alkylene in which the number of carbon atoms is 1 to 20 and optional —CH$_2$— which is not adjacent to each other may be replaced by —O—, —COO—, —OCO—, —CH=CH— or —C≡C—; and $Y^1$ is halogen, —OM$^1$-, —SM$^1$-, —CHO, —COOR$^3$—, —CSOR$^3$—, —CSSR$^3$—, —NHR$^4$—, —COX$^1$—, —CSX$^1$—, —OCOX$^1$—, —OCOOR$^3$—, —N=C=O, —CN, —C≡CH, —CR$^5$=CH$_2$, —CR$^5$=CR$^6$COOR$^3$, —CH=CR$^5$CR$^6$=CH$_2$, —SO$_2$X$^1$, —SiR$^2_2$X$^1$, —SiR$^2_2$OR$^3$, —SiR$^2_2$OCOR$^7$, —SiR$^2_2$OC(CH$_3$)=CH$_2$, —SiR$^2_2$ON=CR$^7$R$^8$, —SiR$^2_2$NR$^7$R$^8$, or any one of groups shown below:

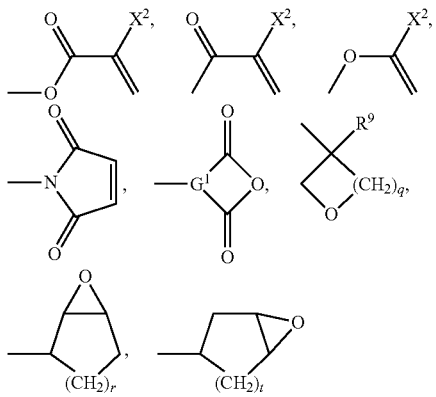

in these groups related to $Y^1$, $M^1$ is hydrogen or alkaline metal; $R^3$ is hydrogen, alkaline metal, or alkyl in which the number of carbon atoms is 1 to 10, optional —CH$_2$— which is not adjacent to each other may be replaced by —O—, and optional hydrogen may be replaced by halogen; $R^4$ is hydrogen, cyclopropyl, cyclobutyl, cyclopentyl, cyclohexyl, cyclohexenyl, alkyl in which the number of carbon atoms is 1 to 10, optional —CH$_2$— which is not adjacent to each other may be replaced by —O— and optional hydrogen may be replaced by halogen, or phenyl in which optional hydrogen may be replaced by halogen or alkyl having 1 to 5 carbon atoms; in the alkyl having 1 to 5 carbon atoms which is a substituent of phenyl, optional —CH$_2$— which is not adjacent to each other may be replaced by =O—, —CH=CH— or —C, and optional hydrogen may be replaced by halogen; $X^1$ is halogen; $R^5$, $R^6$ and $X^2$ are independently hydrogen, halogen, —CN, or alkyl in which the number of carbon atoms is 1 to 10 optional —CH$_2$— which is not adjacent to each other may be replaced by —O—, and optional hydrogen may be replaced by halogen; $R^7$ and $R^8$ are independently alkyl having 1 to 10 carbon atoms; $G^1$ is a trivalent organic group; $R^9$ is hydrogen or alkyl having 1 to 5 carbon atoms; q is 1 or 0; r is an integer of 0 to 5; and t is an integer of 1 to 5.

[2] The compound as described in the item [1], wherein in Formula (1), $R^1$ is phenyl in which optional hydrogen may be replaced by halogen or alkyl having 1 to 5 carbon atoms; in the alkyl having 1 to 5 carbon atoms, optional —CH$_2$— which is not adjacent to each other may be replaced by —O—, and optional hydrogen may be replaced by halogen; $Q^1$ is hydrogen, halogen, alkyl having 1 to 10 carbon atoms, cyclopropyl, cyclobutyl, cyclopentyl, cyclohexyl, cyclohexenyl, or phenyl in which optional hydrogen may be replaced by halogen or alkyl having 1 to 5 carbon atoms; in the alkyl having 1 to 10 carbon atoms and the alkyl having 1 to 5 carbon atoms which is a substituent of phenyl, optional —CH$_2$— which is not adjacent to each other may be replaced by —O—, —CH=CH— or —C≡C—, and optional hydrogen may be replaced by halogen; and $Q^2$ is a group represented by Formula (2);

in Formula (2), the code < represents a bonding point with silicon; l, m, n and p are independently 0, 1, 2 or 3; $A^1$, $A^2$, $A^3$ and $A^4$ are independently a single bond, 1,4-cyclohexylene, 1,4-cyclohexenylene, a condensed ring group having 6 to 10 carbon atoms which is a divalent group, or 1,4-phenylene; in these rings, optional —CH$_2$— which is not adjacent to each other may be replaced by —O—, and optional —CH= may be replaced by —N=; in all rings, optional hydrogen may be replaced by halogen, —CN, —NO$_2$, or alkyl having 1 to 5 carbon atoms; in the alkyl having 1 to 5 carbon atoms, optional —CH$_2$— which is not adjacent to each other may be replaced by —O—, —CH=CH— or —C≡C—, and optional hydrogen may be replaced by halogen; $Z^0$, $Z^1$, $Z^2$ and $Z^3$ are independently a single bond, —CH=CH—, —C≡C—, —COO—, —OCO—, or alkylene in which the number of carbon atoms is 1 to 20, and optional —CH$_2$— may be replaced by —O—, —S—, —NH—, —SiR$^2_2$—, —SiR$^2_2$O—, —OSiR$^2_2$—, —OSiR$^2_2$O—, —SiR$^2_2$OSiR$^2_2$—, —COO—, —OCO—, —CH=CH— or —C≡C—; $R^2$ is halogen, alkyl having 1 to 10 carbon atoms, cyclopropyl, cyclobutyl, cyclopentyl, cyclohexyl, cyclohexenyl, or phenyl in which optional hydrogen may be replaced by halogen or alkyl having 1 to 5 carbon atoms; in the alkyl having 1 to 10 carbon atoms and the alkyl having 1 to 5 carbon atoms which is a substituent of phenyl, optional —CH$_2$— which is not adjacent to each other may be replaced by —O—, —CH=CH— or —C≡C—, and optional hydrogen may be replaced by halogen; $Z^4$ is a Single bond, —CH=CH—, —C≡C—, —COO—, —OCO—, or alkylene in which the number of carbon atoms is 1 to 20, optional —CH$_2$— which is not adjacent to each other may be replaced by —O—, —COO—, —OCO—, —CH=CH— or —C≡C—; and $Y^2$ is halogen, —OM$^1$-, —SM$^1$-, —CHO, —COOR$^3$—, —CSOR$^3$—, —CSSR$^3$—, —NHR$^4$—, —COX$^1$—, —CSX$^1$—, —OCOX$^1$—, —OCOOR$^3$—, —N=C=O, —CN, —C≡CH, —CR$^5$=CH$_2$, —CR$^5$=CR$^6$COOR$^3$, —CH=CR$^5$CR$^6$=CH$_2$, —SO$_2$X$^1$, or any one of groups shown below:

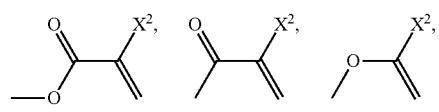

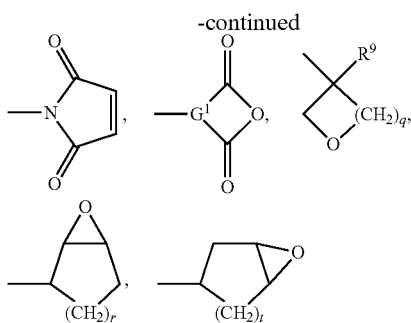

in the above groups related to $Y^1$, $M^1$ is hydrogen or alkaline metal; $R^3$ is hydrogen, alkaline metal, or alkyl in which the number of carbon atoms is 1 to 10, optional —$CH_2$— which is not adjacent to each other may be replaced by —O—, and optional hydrogen may be replaced by halogen; $R^4$ is hydrogen, cyclopropyl, cyclobutyl, cyclopentyl, cyclohexyl, cyclohexenyl, alkyl in which the number of carbon atoms is 1 to 10, optional —$CH_2$— which is not adjacent to each other may be replaced by —O—, and optional hydrogen may be replaced by halogen, or phenyl in which optional hydrogen may be replaced by halogen, or alkyl having 1 to 5 carbon atoms; in the alkyl having 1 to 5 carbon atoms which is a substituent of phenyl, optional —$CH_2$— which is not adjacent to each other may be replaced by =O—, —CH=CH— or —C, and optional hydrogen may be replaced by halogen; $X^1$ is halogen; $R^5$, $R^6$ and $X^2$ are independently hydrogen, halogen, —CN, or alkyl in which the number of carbon atoms is 1 to 10, optional —$CH_2$— which is not adjacent to each other may be replaced by —O—, and optional hydrogen may be replaced by halogen; $G^1$ is a trivalent organic group; $R^9$ is hydrogen or alkyl having 1 to 5 carbon atoms; q is 1 or 0; r is an integer of 0 to 5; and t is an integer of 1 to 5.

[3] The compound as described in the item [1] or [2], wherein $R^1$ is phenyl in which optional hydrogen may be replaced by fluorine or chlorine.

[4] The compound as described in the item [1] or [2], wherein $R^1$ is phenyl in which optional hydrogen may be replaced by fluorine or chlorine; $Q^1$ is cyclopropyl, cyclobutyl, cyclopentyl, cyclohexyl, alkyl in which the number of carbon atoms is 1 to 10, optional hydrogen may be replaced by fluorine, or phenyl in which optional hydrogen may be replaced by fluorine, chlorine or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine.

[5] The compound as described in the item [1] or [2], wherein $R^1$ is phenyl in which optional hydrogen may be replaced by fluorine or chlorine; $Q^1$ is cyclopropyl, cyclobutyl, cyclopentyl, cyclohexyl, alkyl in which the number of carbon atoms is 1 to 10, and optional hydrogen may be replaced by fluorine, or phenyl in which optional hydrogen may be replaced by fluorine, chlorine or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine; $A^1$, $A^2$, $A^3$ and $A^4$ are independently a single bond, 1,4-cyclohexylene, 1,4-cyclohexenylene, a condensed ring group having 6 to 10 carbon atoms which is a divalent group, or 1,4-phenylene; in the above rings, optional hydrogen may be replaced by fluorine, chlorine, or alkyl having 1 to 5 carbon atoms; in the above alkyl having 1 to 5 carbon atoms, optional —$CH_2$— which is not adjacent to each other may be replaced by —O—, and optional hydrogen may be replaced by fluorine; $Z^0$, $Z^1$, $Z^2$ and $Z^3$ are independently a single bond, —CH=CH—, —C≡C—, —COO—, —OCO— or alkylene which has a carbon number of 1 to 20 and in which optional —$CH_2$— may be replaced by —O—, —NH—, —$SiR^2_2$—, —$SiR^2_2OSiR^2_2$—, —COO—, —OCO—, —CH=CH— or —C≡C—; $R^2$ is halogen, cyclopropyl, cyclobutyl, cyclopentyl, cyclohexyl, alkyl in which the number of carbon atoms is 1 to 10, and optional hydrogen may be replaced by fluorine, or phenyl in which optional hydrogen may be replaced by fluorine, chlorine, or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine; and $Z^4$ is a single bond, —CH=CH—, —C≡C—, —COO—, —OCO— or alkylene in which the number of carbon atoms is 1 to 20, and optional —$CH_2$— which is not adjacent to each other may be replaced by —O—, —COO—, —OCO—, —CH=CH— or —C≡C—.

[6] The compound as described in the item [1] or [2], wherein $R^1$ is phenyl in which optional hydrogen may be replaced by fluorine or chlorine; $Q^1$ is cyclopropyl, cyclobutyl, cyclopentyl, cyclohexyl, alkyl in which the number of carbon atoms is 1 to 10, and optional hydrogen may be replaced by fluorine, or phenyl in which optional hydrogen may be replaced by fluorine, chlorine, or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine; $A^1$, $A^2$, $A^3$ and $A^4$ are independently a single bond, 1,4-cyclohexylene, 1,4-cyclohexenylene, a condensed ring group having 6 to 10 carbon atoms which is a divalent group, or 1,4-phenylene; in the above rings, optional hydrogen may be replaced by fluorine, chlorine, or alkyl having 1 to 5 carbon atoms; in the above alkyl having 1 to 5 carbon atoms, optional —$CH_2$— which is not adjacent to each other may be replaced by —O—, and optional hydrogen may be replaced by fluorine; $Z^0$, $Z^1$, $Z^2$ and $Z^3$ are independently a single bond, —CH=CH—, —C≡C—, —COO—, —OCO—, or alkylene in which the number of carbon atoms is 1 to 20, and optional —$CH_2$— which is not adjacent to each other may be replaced by —O—, —NH—, —$SiR^2_2$—, —$SiR^2_2O$—, —$OSiR^2_2$—, —$SiR^2_2OSiR^2_2$—, —COO—, —OCO—; —CH=CH— or —C≡C—; $R^2$ is halogen, cyclopropyl, cyclobutyl, cyclopentyl, cyclohexyl, alkyl in which the number of carbon atoms is 1 to 10, and optional hydrogen may be replaced by fluorine, or phenyl in which optional hydrogen may be replaced by fluorine, chlorine, or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine; $Z^4$ is a single bond, —CH=CH—, —C≡C—, —COO—, —OCO—, or alkylene in which the number of carbon atoms is 1 to 20, and optional —$CH_2$— which is not adjacent to each other may be replaced by —O—, —COO—, —OCO—, —CH=CH— or —C≡C—; and $Y^1$ is chlorine, bromine, —$OM^1$-, —$SM^1$-, —CHO, —$COOR^5$—, —$COX^1$—, —$OCOX^1$—, —N=C=O, —CN, —C≡CH, $CR^5=CH_2$, —$CR^5=CR^6COOR^3$, —CH=$CR^5CR^6=CH_2$, —$SO_2X^1$, 2,3-epoxycyclohexyl, 3,4-epoxycyclohexyl, or any one of groups shown below:

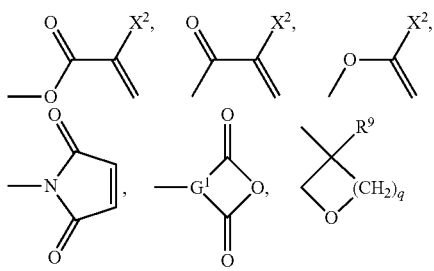

in the above groups related to $Y^1$, $M^1$ is hydrogen or alkaline metal; $R^3$ is hydrogen, alkaline metal, or alkyl having 1 to 5 carbon atoms; $R^4$ is hydrogen, cyclopentyl, cyclohexyl, alkyl in which the number of carbon atoms is 1 to 5, optional —$CH_2$— which is not adjacent to each other may be replaced by —O—, and optional hydrogen may be replaced by fluorine, or phenyl in which optional hydrogen may be replaced by fluorine, chlorine, or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine; $X^1$ is chlorine or bromine; $R^5$, $R^6$ and $X^2$ are independently hydrogen, fluorine; chlorine, or alkyl in which the number of carbon atoms is 1 to 5, optional —$CH_2$— which is not adjacent to each other may be replaced by —O—, and optional hydrogen may be replaced by fluorine; $G^1$ is a trivalent organic group; $R^9$ is hydrogen, methyl or ethyl; and q is 1 or 0.

[7] The compound as described in the item [6], wherein $R^1$ is phenyl.

[8] The compound as described in the item [6], wherein $R^1$ is phenyl; $Q^1$ is cyclopentyl, cyclohexyl, alkyl in which the number of carbon atoms is 1 to 5, and optional hydrogen may be replaced by fluorine, or phenyl in which optional hydrogen may be replaced by fluorine or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine.

[9] The compound as described in the item. [6], wherein $R^1$ is phenyl; $Q^1$ is cyclopentyl, cyclohexyl, alkyl in which the number of carbon atoms is 1 to 5 and optional hydrogen may be replaced by fluorine, or phenyl in which optional hydrogen may be replaced by fluorine or alkyl having 1 to 5 carbon atoms; in the alkyl having 1 to 5 carbon atoms which is a substituent of phenyl, optional —$CH_2$— which is not adjacent to each other may be replaced by —O—, and optional hydrogen may be replaced by fluorine; $A^1$, $A^2$, $A^3$ and $A^4$ are independently a single bond or 1,4-phenylene in which optional hydrogen may be replaced by fluorine, chlorine or alkyl having 1 to 5 carbon atoms; in the alkyl having 1 to 5 carbon atoms which is a substituent for 1,4-phenylene, optional —$CH_2$— which is not adjacent to each other may be replaced by —O—, and optional hydrogen may be replaced by fluorine; and $Z^0$, $Z^1$, $Z^2$, $Z^3$ and $Z^4$ are independently a single bond, —COO—, —OCO—, or alkylene in which the number of carbon atoms is 1 to 20, and optional —$CH_2$— which is not adjacent to each other may be replaced by —O—, —COO—, —OCO—, —CH=CH— or —C≡C—.

[10] The compound as described in the item [6], wherein $R^1$ is phenyl; $Q^1$ is cyclopentyl, cyclohexyl, alkyl in which the number of carbon atoms is 1 to 5, and optional hydrogen may be replaced by fluorine, or phenyl in which optional hydrogen may be replaced by fluorine or alkyl having 1 to 5 carbon atoms; in the alkyl having 1 to 5 carbon atoms which is a substituent of phenyl, optional hydrogen may be replaced by fluorine; $A^1$, $A^2$, $A^3$ and $A^4$ are independently a single bond or 1,4-phenylene in which optional hydrogen may be replaced by fluorine, chlorine or alkyl having 1 to 5 carbon atoms; in the alkyl having 1 to 5 carbon atoms which is a substituent for 1,4-phenylene, optional —$CH_2$— which is not adjacent to each other may be replaced by —O—, and optional hydrogen may be replaced by fluorine; $Z^0$, $Z^1$, $Z^2$, $Z^3$ and $Z^4$ are independently a single bond, —COO—, —OCO— or alkylene in which the number of carbon atoms is 1 to 20, and optional —$CH_2$— which is not adjacent to each other may be replaced by —O—, —COO—, —OCO—, —CH=CH— or —C≡C—; and $Y^1$ is —$OM^1$-, —CHO, —$COOR^3$—, —$NHR^4$—, —$COX^1$—, —$OCOX^1$—, —N=C=O, —$CR^5$=$CH_2$, 2,3-epoxycyclohexyl, 3,4-epoxycyclohexyl, or any one of groups shown below:

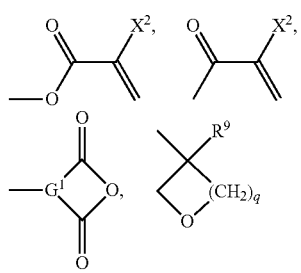

in the above groups related to $Y^1$, $M^1$ is hydrogen, sodium or potassium; $R^3$ is hydrogen, sodium, potassium, or alkyl in which the number of carbon atoms is 1 to 5, optional —$CH_2$— which is not adjacent to each other may be replaced by —O—, and optional hydrogen may be replaced by fluorine; $R^4$ is hydrogen, phenyl, or alkyl in which the number of carbon atoms is 1 to 5, optional —$CH_2$— which is not adjacent to each other may be replaced by —O—, and optional hydrogen may be replaced by fluorine; $X^1$ is chlorine or bromine; $R^5$ and $X^2$ are independently hydrogen, fluorine, chlorine, or alkyl in which the number of carbon atoms is 1 to 5, optional —$CH_2$— which is not adjacent to each other may be replaced by —O—, and optional hydrogen may be replaced by fluorine; $G^1$ is a trivalent organic group; $R^9$ is hydrogen, methyl or ethyl; and q is 1 or 0.

[11] The compound as described in the item [10], wherein $Q^1$ is alkyl having 1 to 5 carbon atoms, or phenyl.

[12] The compound as described in the item [10], wherein $Q^1$ is alkyl having 1 to 5 carbon atoms or phenyl; $A^1$, $A^2$, $A^3$ and $A^4$ are independently a single bond or 1,4-phenylene in which optional hydrogen may be replaced by fluorine or methyl; $Z^0$, $Z^1$, $Z^2$, $Z^3$ and $Z^4$ are independently a single bond, —COO—, —OCO— or alkylene in which the number of carbon atoms is 1 to 20 and optional —$CH_2$—, which is not adjacent to each other, may be replaced by —O—, —COO— or —OCO—.

[13] The compound as described in the item [10], wherein $Q^1$ is alkyl having 1 to 5 carbon atoms or phenyl; $A^1$, $A^2$, $A^3$ and $A^4$ are independently a single bond or 1,4-phenylene in which optional hydrogen may be replaced by fluorine or methyl; $Z^0$, $Z^1$, $Z^2$, $Z^3$ and $Z^4$ are independently a single bond, —COO—, —OCO— or alkylene in which the number of carbon atoms is 1 to 20 and optional —$CH_2$—, which is not adjacent to each other, may be replaced by —O—, —COO— or —OCO—; and $Y^1$ is —$OM^1$-, —$COOR^3$—, —$COX^1$—, —N═C═O, —CR$^5$═CH$_2$, 2,3-epoxycyclohexyl, 3,4-epoxycyclohexyl, or any one of groups shown below:

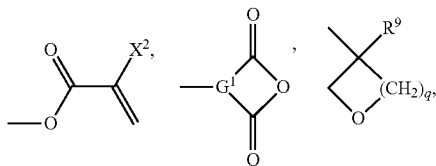

in the above groups related to Y$^1$, M$^1$ is hydrogen, sodium or potassium; R$^3$ is hydrogen, sodium, potassium, methyl or ethyl; R$^4$ is hydrogen, methyl or phenyl; X$^1$ is chlorine or bromine; R$^9$ and X$^2$ are independently hydrogen, fluorine or alkyl in which the number of carbon atoms is 1 to 5 and optional hydrogen may be replaced by fluorine; G$^1$ is a trivalent organic group; R$^9$ is hydrogen, methyl or ethyl; and q is 1 or 0.

[14] The compound as described in the item [13], wherein Q$^1$ is methyl or phenyl.

[15] The compound as described in the item [13], wherein Q$^1$ is methyl or phenyl; A$^1$, A$^2$, A$^3$ and A$^4$ are independently a single bond or 1,4-phenylene; and Z$^0$, Z$^1$, Z$^2$, Z$^3$ and Z$^4$ are independently a single bond, —COO—, —OCO— or alkylene in which the number of carbon atoms is 1 to 20 and optional —CH$_2$—, which is not adjacent to each other, may be replaced by —O—, —COO— or —OCO—.

[16] The compound as described in the item [13], wherein Q$^1$ is methyl or phenyl; A$^1$, A$^2$, A$^3$ and A$^4$ are independently a single bond or 1,4-phenylene; Z$^0$, Z$^1$, Z$^2$, Z$^3$ and Z$^4$ are independently a single bond, —COO—, —OCO— or alkylene in which the number of carbon atoms is 1 to 20 and optional —CH$_2$—, which is not adjacent to each other, may be replaced by —O—, —COO— or —OCO—; and Y$^1$ is —COOR$^3$—, —NHR$^4$—, —COCl—, 2,3-epoxycyclohexyl, 3,4-epoxycyclohexyl, or any one of groups shown below:

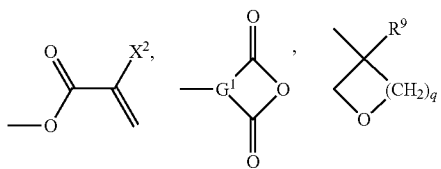

in the above groups related to Y$^2$, M$^2$ is hydrogen, sodium or potassium; R$^3$ is hydrogen, sodium, potassium, methyl or ethyl; R$^4$ is hydrogen or methyl; X$^2$ is hydrogen, fluorine or methyl; G$^1$ is a trivalent organic group; R$^9$ is hydrogen, methyl or ethyl; and q is 1 or 0.

[17] The compound as described in the item [16], wherein Y$^1$ is —OH, —COOR$^3$, —NH$_2$, —COCl, 2,3-epoxycyclohexyl, 3,4-epoxycyclohexyl, or any one of groups shown below:

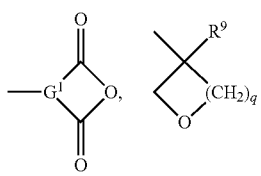

in the above groups related to Y$^1$, R$^3$ is hydrogen, methyl or ethyl; G$^1$ is a trivalent organic group; R$^9$ is hydrogen, methyl or ethyl; and q is 1 or 0.

[18] A polymer having a structural unit represented by Formula (3):

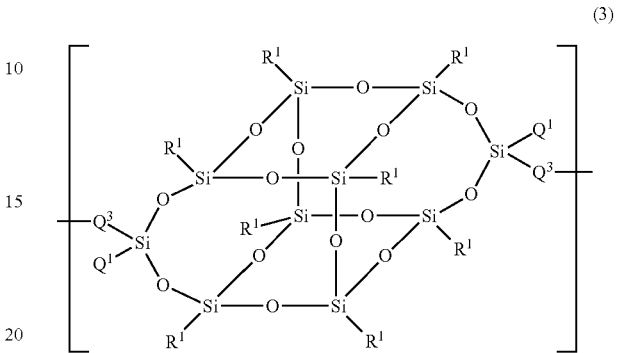

wherein R$^1$ is phenyl in which optional hydrogen may be replaced by halogen or alkyl having 1 to 5 carbon atoms; in the alkyl having 1 to 5 carbon atoms, optional —CH$_2$—, which is not adjacent to each other, may be replaced by —O—, and optional hydrogen may be replaced by halogen; Q$^1$ is hydrogen, halogen, alkyl having 1 to 10 carbon atoms, cyclopropyl, cyclobutyl, cyclopentyl, cyclohexyl, cyclohexenyl, or phenyl in which optional hydrogen may be replaced by halogen or alkyl having 1 to 5 carbon atoms; in the alkyl having 1 to 10 carbon atoms and alkyl having 1 to 5 carbon atoms which is a substituent of phenyl, optional —CH$_2$—, which is not adjacent to each other, may be replaced by —O—, —CH═CH— or —C≡C—, and optional hydrogen may be replaced by halogen; and Q$^3$ is a group represented by Formula (4):

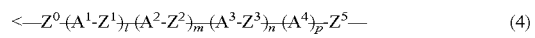

wherein a code < represents a bonding point with silicon; l, m, n and p are independently 0, 1, 2 or 3; A$^1$, A$^2$, A$^3$ and A$^4$ are independently a single bond, 1,4-cyclohexylene, 1,4-cyclohexenylene, a condensed ring group having 6 to 10 carbon atoms which is a divalent group, or 1,4-phenylene; in these rings, optional —CH$_2$—, which is not adjacent to each other, may be replaced by —O—, and optional —CH═ may be replaced by —N═; optional hydrogen in all rings may be replaced by halogen, —CN, —NO$_2$ or alkyl having 1 to 5 carbon atoms; in the alkyl having 1 to 5 carbon atoms, optional —CH$_2$—, which is not adjacent to each other, may be replaced by —O—, —CH═CH— or —C≡C—; and optional hydrogen may be replaced by halogen; Z$^0$, Z$^1$, Z$^2$ and Z$^3$ are independently a single bond, —CH═CH—, —COO—, —OCO— or alkylene in which the number of carbon atoms is 1 to 20 and optional —CH$_2$— may be replaced by —O—, —S—, —NH—, —SiR$^2$$_2$—, —SiR$^2$$_2$O—, —OSiR$^2$$_2$—, —OSiR$^2$$_2$O—, —SiR$^2$$_2$OSiR$^2$$_2$—, —COO—, —OCO—, —CH═CH— or —C≡C—; R$^2$ is halogen, alkyl having 1 to 10 carbon atoms, cyclopropyl, cyclobutyl, cyclopentyl, cyclohexyl, cyclohexenyl, or phenyl in which optional hydrogen may be replaced by halogen or alkyl having 1 to 5 carbon atoms; in the alkyl having 1 to 10 carbon atoms and alkyl having 1 to 5 carbon atoms which is a substituent of phenyl, optional —CH$_2$—, which is not adjacent to each other, may be replaced by —O—, —CH═CH— or —C≡C—, and optional hydrogen may be replaced by halogen; Z$^5$ is a single bond, —CH═CH—, —C≡C—, —COO—, —OCO— or a group represented by —W¹-T¹-; W¹ is a single bond or alkylene in which the number of carbon atoms is 1 to 20 and optional —CH₂—, which is not adjacent to each other, may be replaced by —O—, —COO—, OCO—, —CH═CH— or —C≡C—; and T¹ is —O—, —S—, —SiR²₂—, —SiR²₂O—, —OSiR²₂—, —OSiR²₂O—, —SiR²₂OSiR²₂—, —CO—, —COO—, —OCO—, —CSO—, —OCS—, —CONR¹⁰—, —NR¹⁰CO—, —CONR¹⁰O—, —ONR¹⁰CO—, —OCONR¹⁰—, —NR¹⁰CONR¹⁰—, —NR¹⁰COO—, —OCOO—, —CH(OH)CH₂—, —CH₂CH(OH)—, —CH═CH—, —CH₂CR⁵═CR⁶CH₂—, —C≡C—, —SO₂—, —SO₂O—, —OSO₂—, —SO₂S—, —SSO₂—, —SO₂NR⁷—, —NR¹⁰SO₂—, or any one of groups shown below:

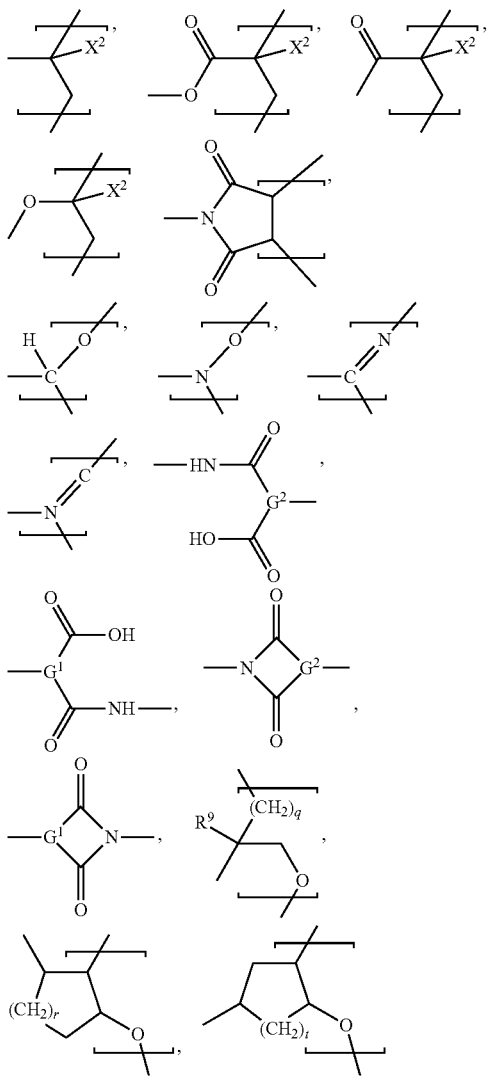

in the groups related to T¹, R² is the same as described above; R¹⁰ is hydrogen, cyclopropyl, cyclobutyl, cyclopentyl, cyclohexyl, cyclohexenyl, alkyl in which the number of carbon atoms is 1 to 10, and optional hydrogen may be replaced by halogen, or phenyl in which optional hydrogen may be replaced by halogen or alkyl having 1 to 5 carbon atoms; in the alkyl having 1 to 5 carbon atoms which is a substituent of phenyl, optional —CH₂—, which is not adjacent to each other, may be replaced by —O—, —CH═CH— or —C, and optional hydrogen may be replaced by halogen; R⁵, R⁶ and X² are independently hydrogen, halogen, —CN or alkyl in which the number of carbon atoms is 1 to 10; optional —CH₂—, which is not adjacent to each other, may be replaced by —O—, and optional hydrogen may be replaced by halogen; G¹ is a trivalent organic group; G² is a part of tricarboxylic acid-derivative's residue or a part of tetracarboxylic acid-derivative's residue; R⁹ is hydrogen or alkyl having 1 to 5 carbon atoms; q is 1 or 0; r is an integer of 0 to 5; and t is an integer of 1 to 5.

[19] The polymer as described in the item [18], wherein R¹ is phenyl in which optional hydrogen may be replaced by fluorine or chlorine.

[20] The polymer as described in the item [18], wherein R¹ is phenyl in which optional hydrogen may be replaced by fluorine or chlorine; Q¹ is cyclopropyl, cyclobutyl, cyclopentyl, cyclohexyl, alkyl in which the number of carbon atoms is 1 to 10 and optional hydrogen may be replaced by fluorine, or phenyl in which optional hydrogen may be replaced by fluorine, chlorine or alkyl having 1 to 5 carbon atoms; and in the alkyl having 1 to 5 carbon atoms which is a substituent of phenyl, optional —CH₂—, which is not adjacent to each other, may be replaced by —O—, and optional hydrogen may be replaced by fluorine.

[21] The polymer as described in the item [18], wherein R¹ is phenyl in which optional hydrogen may be replaced by fluorine or chlorine; Q¹ is cyclopropyl, cyclobutyl, cyclopentyl, cyclohexyl, alkyl in which the number of carbon atoms is 1 to 10 and optional hydrogen may be replaced by fluorine, or phenyl in which optional hydrogen may be replaced by fluorine, chlorine or alkyl having 1 to 5 carbon atoms; in the alkyl having 1 to 5 carbon atoms which is a substituent of phenyl, optional —CH₂—, which is not adjacent to each other, may be replaced by —O—, and optional hydrogen may be replaced by fluorine; A¹, A², A³ and A⁴ are independently a single bond, 1,4-cyclohexylene, 1,4-cyclohexenylene, 1,4-phenylene or a condensed ring group having 6 to 10 carbon atoms which is a divalent group; in these rings, optional hydrogen may be replaced by fluorine, chlorine or alkyl having 1 to 5 carbon atoms; in the alkyl having 1 to 5 carbon atoms, optional —CH₂—, which is not adjacent to each other, may be replaced by —O—, and optional hydrogen may be replaced by fluorine; Z⁰, Z¹, Z² and Z³ are independently a single bond, —CH═CH—, —C≡C—, —COO—, —OCO— or alkylene in which the number of carbon atoms is 1 to 20 and optional —CH₂—, which is not adjacent to each other, may be replaced by —O—, —NH—, —SiR²₂O—, —OSiR²₂—, —SiR²₂OSiR²₂—, —COO—, —OCO—, —CH═CH— or —C≡C—; R² is halogen, cyclopropyl, cyclobutyl, cyclopentyl, cyclohexyl, alkyl in which the number of carbon atoms is 1 to 10 and optional hydrogen may be replaced by fluorine, or phenyl in which optional hydrogen may be replaced by fluorine, chlorine or alkyl having 1 to 5 carbon atoms; in the alkyl having 1 to 5 carbon atoms which is a substituent of phenyl, optional —CH₂—, which is not adjacent to each other, may be replaced by —O—, and optional hydrogen may be replaced by fluorine; Z⁵ is a single bond, —CH═CH—, —C≡C—, —COO—, —OCO— or a group represented by —W¹-T¹; W¹ is a single bond or alkylene in which the number of carbon atoms is 1 to 20 and optional —CH₂—, which is not adjacent to each other, may be replaced by —O—, —COO—, —OCO—, —CH═CH— or —C≡C—; and T¹ is —O—, —COO—, —OCO—, —CONR¹⁰—, —NR¹⁰CO—, —OCOO—, —CH(OH)CH₂—, —CH₂CH(OH)—, —CH═CH—, —SO₂—, or any one of groups shown below:

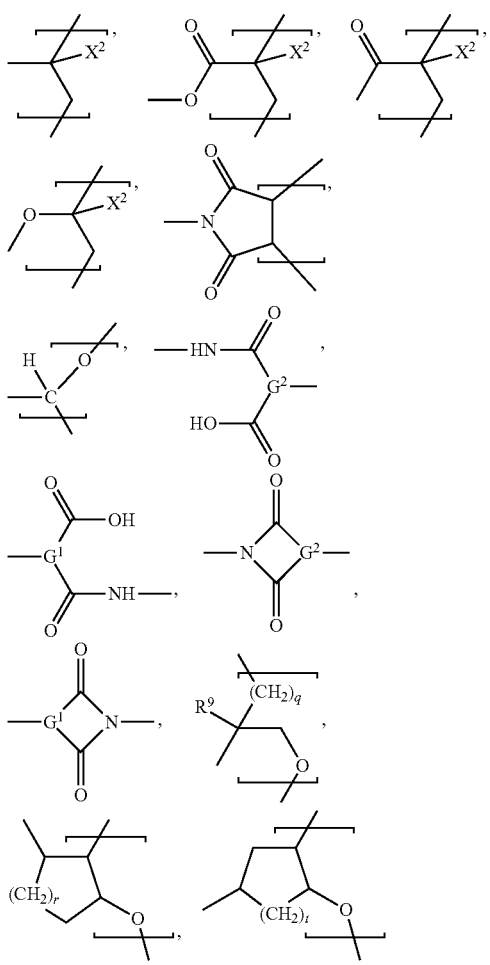

in these groups related to $T^1$, $R^{10}$ is hydrogen, cyclopentyl, cyclohexyl, alkyl in which the number of carbon atoms is 1 to 5 and optional hydrogen may be replaced by fluorine, or phenyl in which optional hydrogen may be replaced by fluorine, chlorine or alkyl having 1 to 5 carbon atoms; in the alkyl having 1 to 5 carbon atoms which is a substituent of phenyl, optional —$CH_2$—, which is not adjacent to each other, may be replaced by —O—, and optional hydrogen may be replaced by fluorine; $X^2$ is hydrogen, fluorine, chlorine or alkyl in which the number of carbon atoms is 1 to 5, optional —$CH_2$—, which is not adjacent to each other, may be replaced by —O— and optional hydrogen may be replaced by fluorine; $G^1$ is a trivalent organic group; $G^2$ is a part of tricarboxylic acid-derivative's residue or a part of tetracarboxylic acid-derivative's residue; $R^9$ is hydrogen, methyl or ethyl; q is 1 or 0; r is an integer of 0 to 5; and t is an integer of 1 to 5.

[22] The polymer as described in the item [21], wherein $R^1$ is phenyl.

[23] The polymer as described in the item [21], wherein $R^1$ is phenyl; $Q^1$ is cyclopentyl, cyclohexyl, alkyl in which the number of carbon atoms is 1 to 5 and optional hydrogen may be replaced by fluorine, or phenyl in which optional hydrogen may be replaced by fluorine or alkyl having 1 to 5 carbon atoms; and in the alkyl having 1 to 5 carbon atoms which is a substituent of phenyl, optional —$CH_2$—, which is not adjacent to each other, may be replaced by —O—, and optional hydrogen may be replaced by fluorine.

[24] The polymer as described in the item [21], wherein $R^1$ is phenyl; $Q^1$ is cyclopentyl, cyclohexyl, alkyl having 1 to 5 carbon atoms, or phenyl in which optional hydrogen may be replaced by fluorine or alkyl having 1 to 5 carbon atoms; in the alkyl having 1 to 5 carbon atoms which is a substituent of phenyl, optional —$CH_2$—, which is not adjacent to each other, may be replaced by —O—, and optional hydrogen may be replaced by fluorine; $A^1$, $A^2$, $A^1$ and $A^4$ are independently a single bond or 1,4-phenylene in which optional hydrogen may be replaced by fluorine, chlorine or alkyl having 1 to 5 carbon atoms; in the alkyl having 1 to 5 carbon atoms which is a substituent of 1,4-phenylene, optional —$CH_2$—, which is not adjacent to each other, may be replaced by —O—, and optional hydrogen may be replaced by fluorine; $Z^0$, $Z^1$, $Z^2$ and $Z^3$ are independently a single bond, —COO—, —OCO— or alkylene in which the number of carbon atoms is 1 to 20 and optional —$CH_2$—, which is not adjacent to each other, may be replaced by —O—, —COO— or —OCO—; $Z^5$ is a single bond, —COO—, —OCO— or a group represented by —$W^1$-$T^1$; $W^1$ is a single bond or alkylene in which the number of carbon atoms is 1 to 20 and optional —$CH_2$—, which is not adjacent to each other, may be replaced by —O—, —COO— or —OCO—; and $T^1$ is —O—, —COO—, —OCO—, —$CONR^{10}$—, —$NR^{10}CO$—, or any one of groups shown below:

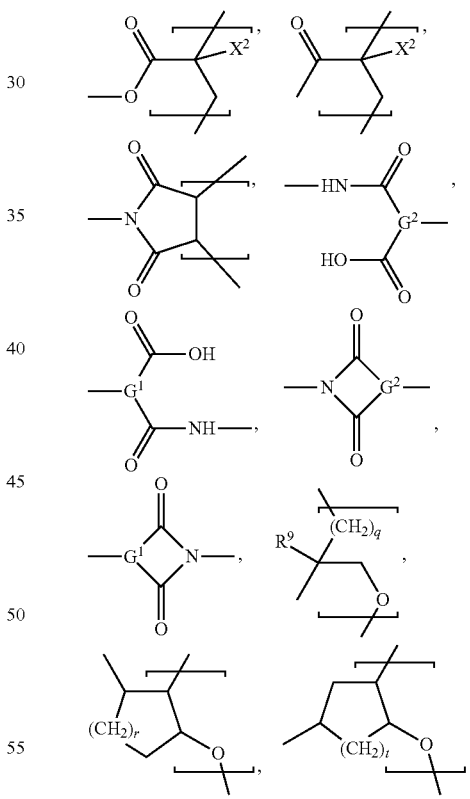

in these groups related to $T^2$, $R^{10}$ is hydrogen, alkyl having 1 to 5 carbon atoms, or phenyl; $X^2$ is hydrogen, fluorine or alkyl having 1 to 5 carbon atoms; $G^1$ is a trivalent organic group; $G^2$ is a part of tricarboxylic acid-derivative's residue or a part of tetracarboxylic acid-derivative's residue; $R^9$ is hydrogen, methyl or ethyl; q is 1 or 0; r is an integer of 0 to 5; and t is an integer of 1 to 5.

[25] The polymer as described in the item [24], wherein $Q^1$ is methyl or phenyl.

[26] The polymer as described in the item [24], wherein $Q^1$ is methyl or phenyl; $A^1$, $A^2$, $A^3$ and $A^4$ are independently a single bond or 1,4-phenylene; $Z^0$, $Z^1$, $Z^2$ and $Z^3$ are independently a single bond, —COO—, —OCO— or alkylene in which the number of carbon atoms is 1 to 20 and optional —CH$_2$—, which is not adjacent to each other, may be replaced by —O—, —COO— or —OCO—; $Z^5$ is a single bond, —COO—, —OCO— or a group represented by —W$^1$-T$^1$; W$^1$ is a single bond or alkylene in which the number of carbon atoms is 1 to 20 and optional —CH$_2$—, which is not adjacent to each other, may be replaced by —O—, —COO— or —OCO—; and T$^1$ is —O—, —COO—, —OCO—, —CONR$^{10}$—, —NR$^{10}$CO—, or any one of groups shown below:

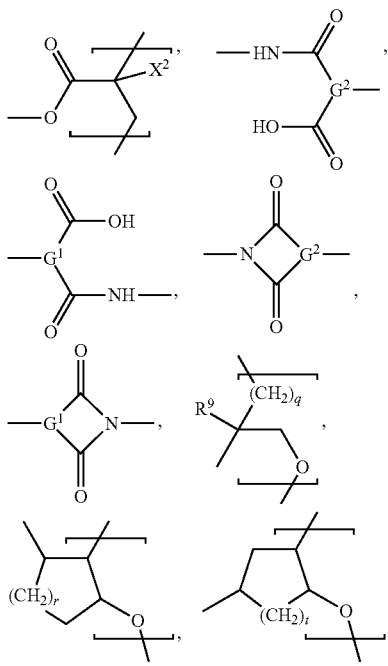

in these groups related to T$^1$, R$^{10}$ is hydrogen or methyl; X$^2$ is hydrogen or methyl; G$^1$ is a trivalent organic group; G$^2$ is a part of tricarboxylic acid-derivative's residue or a part of tetracarboxylic acid-derivative's residue; R$^9$ is hydrogen, methyl or ethyl; q is 1 or 0; r is an integer of 0 to 5; and t is an integer of 1 to 5.

[27] The polymer as described in the item [26], wherein T$^1$ is —O—, —COO—, —CONR$^{10}$—, —NR$^{10}$CO—, or any one of groups shown below:

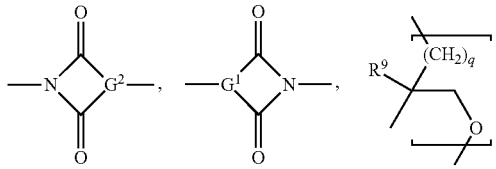

[28] A composition comprising the compound as described in any one of the items [1] to [17].

[29] A polymer obtained by using at least one of the compounds as described in any one of the items [1] to [17].

[30] The polymer as described in the item [29], obtained by using only the compound as described in any one of the items [1] to [17].

[31] The polymer as described in the item [29], obtained by using at least one of the compounds as described in any one of the items [1] to [17] and at least one of compounds other than the compound as described in the item [1].

[32] The polymer as described in any one of the items [18] to [27], or any one of the items [29] to [31], wherein the polymer is polyimide, polyamic acid, polyester, an epoxy resin, polyacrylate or polymethcylate.

[33] A composition comprising at least one of the polymers as described in any one of the items [18] to [27], or any one of the items [29] to [31].

[34] A coating agent comprising the polymer as described in any one of the items [18] to [27], or any one of the items [29] to [31].

[35] A varnish composition comprising the polymer as described in any one of the items [18] to [27], or any one of the items [29] to [31].

[36] A thin film formed by using the varnish composition as described in the item [35].

[37] A multilayer thin film formed by using the varnish composition as described in the item [35] and at least one of compositions of other polymers.

[38] A structural matter, wherein a part or the whole of a structural unit thereof is comprised with at least one of the polymer as described in any one of the items [18] to [27], or any one of the items [29] to [31].

[39] A plastic substrate having the thin film as described in the item [36].

[40] An optical material having the thin film as described in the item [36].

DETAILED DESCRIPTION OF THE INVENTION

In the following explanations, the compound represented by Formula (1) shall be designated as the compound (1), and the polymer having the structural unit represented by Formula (3) shall be designated as the polymer (3). Compounds and polymers represented by other formulas shall be designated by the same abbreviation. A silsesquioxane skeleton shall be designated as a PSQ skeleton.

First, the compound of the present invention shall be explained. The compound of the present invention has a silsesquioxane skeleton and is represented by Formula (1), (1)

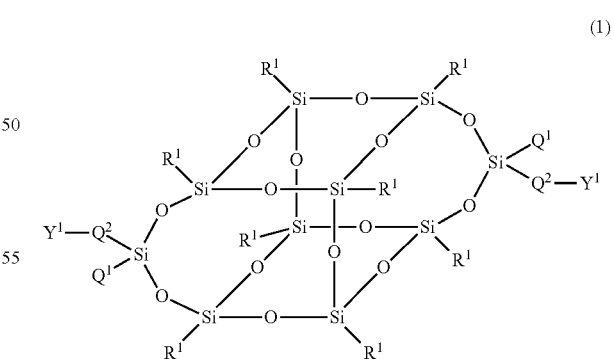

R$^1$ in Formula (1) is phenyl in which optional hydrogen may be replaced by halogen or alkyl having 1 to 5 carbon atoms. In the alkyl having 1 to 5 carbon atoms, optional —CH$_2$—, which is not adjacent to each other, may be replaced by —O—, and optional hydrogen may be replaced by halogen. The preferred examples of R$^1$ are phenyl and phenyl in which at least one hydrogen is replaced by halogen or alkyl having 1 to 5 carbon atoms. More preferred examples of $R^1$ are phenyl and phenyl in which at least one hydrogen is replaced by alkyl having 1 to 5 carbon atoms. The most preferred example of $R^1$ is phenyl.

$Q^1$ in Formula (1) is hydrogen, halogen, cyclopropyl, cyclobutyl, cyclopentyl, cyclohexyl, cyclohexenyl, alkyl having 1 to 10 carbon atoms, or phenyl in which optional hydrogen may be replaced by halogen or alkyl having 1 to 5 carbon atoms. In both of the alkyl having 1 to 10 carbon atoms and the alkyl having 1 to 5 carbon atoms which is a substituent of phenyl, optional —CH$_2$—, which is not adjacent to each other, may be replaced by —O—, —CH=CH— or —C and optional hydrogen may be replaced by halogen.

The preferred examples of $Q^1$ are hydrogen, halogen, cyclopropyl, cyclobutyl, cyclopentyl, cyclohexyl, alkyl having 1 to 10 carbon atoms in which optional —CH$_2$—, which is not adjacent to each other, may be replaced by —CH=CH—, and phenyl in which optional hydrogen may be replaced by halogen or alkyl having 1 to 5 carbon atoms. In the alkyl having 1 to 5 carbon atoms which is a substituent of phenyl, optional —CH$_2$—, which is not adjacent to each other, may be replaced by —O—. In both of the alkyl having 1 to 10 carbon atoms and the alkyl having 1 to 5 carbon atoms which is a substituent of phenyl, optional hydrogen may be replaced by halogen.

More preferred examples of $Q^2$ are hydrogen, —F, —Cl, —CF$_3$, —OCF$_3$, methyl, ethyl, propyl, butyl, pentyl, hexyl, heptyl, methoxy, ethoxy, propoxy, butoxy, pentyloxy, hexyloxy, heptyloxy, methoxymethyl, ethoxymethyl, propoxymethyl, butoxymethyl, methoxyethyl, ethoxyethyl, propoxymethyl, methoxypropyl, ethoxylpropyl, propoxypropyl, 2-fluoroethyl, 3-fluoropropyl, vinyl, 1-propenyl, 2-propenyl, allyl, 3-butenyl, 3-pentenyl, cyclopropyl, cyclobutyl, cyclopentyl, cyclohexyl and phenyl.

$Q^2$ in Formula (1) is a group represented by Formula (2).

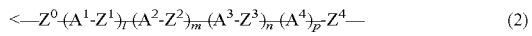 (2)

In Formula (2), a code $<$ represents a bonding point with silicon. $A^1$, $A^2$, $A^3$ and $A^4$ are independently a single bond, 1,4-cyclohexylene, 1,4-cyclohexenylene, a condensed ring group having 6 to 10 carbon atoms which is a divalent group, or 1,4-phenylene. In these rings, optional —CH$_2$—, which is not adjacent to each other, may be replaced by —O—, and optional —CH= may be replaced by —N=. However, it is not preferred that two adjacent —CH$_2$— are replaced in the form of —O—O—. The examples of 1,4-cyclohexylene in which —CH$_2$— is replaced by —O—, are 1,3-dioxane-2,5-diyl and 1,4-dioxane-2,5-diyl. The examples of 1,4-phenylene in which —CH= is replaced by —N=, are pyridine-2,5-diyl, pyrimidine-2,5-diyl and pyridazine-3,6-diyl. And, in all the rings described above which are the examples of $A^1$ to $A^4$, optional hydrogen may be replaced by halogen, —CN, —NO$_2$ or alkyl having 1 to 5 carbon atoms. In the alkyl having 1 to 5 carbon atoms, optional —CH$_2$—, which is not adjacent to each other, may be replaced by —O—, —CH=CH— or —C≡C—, and optional hydrogen may be replaced by halogen.

The preferred examples of $A^1$ to $A^4$ are a single bond, 1,4-cyclohexylene, 1,4-cyclohexenylene, bicyclo[3.1.0]hex-3,6-diyl, bicyclo[2.2.2]oct-1,4-diyl, 1,4-phenylene, 1,3-dioxane-2,5-diyl, pyridine-2,5-diyl, pyrimidine-2,5-diyl, pyridazine-3,6-diyl, 1,4-cyclohexylene in which at least one hydrogen is replaced by halogen or alkyl having 1 to 5 carbon atoms, and 1,4-phenylene in which at least one hydrogen is replaced by halogen or alkyl having 1 to 5 carbon atoms.

More preferred examples of $A^1$ to $A^4$ are a single bond, 1,4-cyclohexylene, 1,4-cyclohexenylene, 1,4-phenylene, pyridine-2,5-diyl, pyrimidine-2,5-diyl, pyridazine-3,6-diyl, 1,4-cyclohexylene in which at least one hydrogen is replaced by fluorine or methyl, and 1,4-phenylene in which at least one hydrogen is replaced by fluorine, chlorine, methyl, ethyl or propyl.

Further more preferred examples of $A^1$ to $A^4$ are 1,4-cyclohexylene, 1,4-phenylene, 2-fluoro-1,4-phenylene, 3-fluoro-1,4-phenylene, 2,3-difluoro-1,4-phenylene, 2,5-difluoro-1,4-phenylene, 2,6-difluoro-1,4-phenylene, 3,5-difluoro-1,4-phenylene, 2-methyl-1,4-phenylene, 2-ethyl-1,4-phenylene, 2-propyl-1,4-phenylene, 3-methyl-1,4-phenylene, 3-ethyl-1,4-phenylene and 3-propyl-1,4-phenylene.

$Z^0$, $Z^1$, $Z^2$, and $Z^3$ in Formula (2) are bonding groups. They are independently a single bond, —CH=CH—, —C COO—, —OCO—, or alkylene having 1 to 20 carbon atoms. Optional —CH$_2$—, which is not adjacent to each other, in the alkylene may be replaced by —O—, —S—, —NH—, —SiR$^2_2$—, —SiR$^2_2$O—, —OSiR$^2_2$—, —OSiR$^2_2$O—, —SiR$^2_2$OSiR$^2_2$—, —COO—, —OCO—, ≡CH=CH— or —C The alkylene may have asymmetric carbon and may be optically active.

$R^2$ described above is halogen, cyclopropyl, cyclobutyl, cyclopentyl, cyclohexyl, cyclohexenyl, alkyl having 1 to 10 carbon atoms, or phenyl in which optional hydrogen may be replaced by halogen or alkyl having 1 to 5 carbon atoms. In the alkyl having 1 to 10 carbon atoms and the alkyl having 1 to 5 carbon atoms which is a substituent of phenyl, optional —CH$_2$—, which is not adjacent to each other, may be replaced by —O—, —CH=CH— or —C≡C—, and optional hydrogen may be replaced by halogen.

The preferred examples of $Z^0$ to $Z^3$ are a single bond, —(CH$_2$)$_a$—, —O(CH$_2$)$_a$—, —(CH$_2$)$_a$O—, —O(CH$_2$)$_a$O—, —(CH$_2$)$_a$O(CH$_2$)$_b$—, —O(CH$_2$)$_a$O(CH$_2$)$_b$≡O, —CHOOH— and C—OCO—. The terms a and b are independently an integer of 1 to 18, and the preferred range thereof is 1 to 10. More preferred examples of $Z^0$ to $Z^3$ are a single bond, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —OCH$_2$—, —O(CH$_2$)$_2$—, —O(CH$_2$)$_3$—, —O(CH$_2$)$_4$—, —O(CH$_2$)$_5$—, —O(CH$_2$)$_6$—, —O(CH$_2$)$_7$—, —O(CH$_2$)$_8$—, —O(CH$_2$)$_9$—, —O(CH$_2$)$_{10}$—, —CH$_2$O—, —(CH$_2$)$_2$O—, —(CH$_2$)$_3$O—, —(CH$_2$)$_4$O—, —(CH$_2$)$_5$O—, —(CH$_2$)$_6$O—, —(CH$_2$)$_7$O—, —(CH$_2$)$_8$O—, —(CH$_2$)$_9$O—, —(CH$_2$)$_{10}$O—, —O(CH$_2$)$_2$O—, —O(CH$_2$)$_3$O—, —O(CH$_2$)$_4$O—, —O(CH$_2$)$_5$O—, —O(CH$_2$)$_6$O—, —O(CH$_2$)$_7$O—, —O(CH$_2$)$_8$O—, —O(CH$_2$)$_9$O—, —O(CH$_2$)$_{10}$O—, —CH$_2$OCH$_2$—, —(CH$_2$)$_2$OCH$_2$—, —(CH$_2$)$_3$OCH$_2$—, —(CH$_2$)$_4$OCH$_2$—, —(CH$_2$)$_5$OCH$_2$—, —(CH$_2$)$_6$OCH$_2$—, —(CH$_2$)$_7$OCH$_2$—, —(CH$_2$)$_6$OCH$_2$—, —(CH$_2$)$_5$OCH$_2$—, —(CH$_2$)$_{10}$OCH$_2$—, —O(CH$_2$)$_2$OCH$_2$—, —O(CH$_2$)$_3$OCH$_2$—, —O(CH$_2$)$_4$OCH$_2$—, —O(CH$_2$)$_5$OCH$_2$—, —O(CH$_2$)$_6$OCH$_2$—, —O(CH$_2$)$_7$OCH$_2$—, —O(CH$_2$)$_8$OCH$_2$—, —O(CH$_2$)$_9$OCH$_2$—, —O(CH$_2$)$_{10}$OCH$_2$— and —CH=CH—.

$Z^4$ in Formula (2) is a single bond, —CH=CH—, —COO—, —OCO— or, alkylene having 1 to 20 carbon atoms. In the alkylene having 1 to 20 carbon atoms, optional —CH$_2$—, which is not adjacent to each other, may be replaced by —O—, —COO—, —OCO—, —CH=CH— or —C≡C—. The preferred example of $Z^4$ is alkylene in which the number of carbon atoms is 1 to 20 and optional —CH$_2$—, which is not adjacent to each other, may be replaced by —O—, —COO— or —OCO—.

When rings or bonding groups contained in the group represented by Formula (2) have plural steric configurations, the steric configurations may be any one of cis, trans and a mixture thereof. The bonds of $R^1$, $Q^1$ and $Q^2$ to the PSQ skeleton are not restricted in terms of a steric configuration.

$Y^1$ in Formula (1) is halogen, —$OM^1$, —$SM^1$, —CHO, —$COOR^3$, —$CSOR^3$, —$CSSR^3$, —$NHR^4$, —$COX^1$, —$CSX^1$, —$OCOX^1$, —$OCOOR^3$, —N=C=O, ≡CN, —$CR^5$=$CH_2$, —$CR^5$=$CR^6COOR^3$, —CH=$CR^5CR^6$=$CH_2$, —$SO_2X^1$, —$SiR^2_2X^1$, —$SiR^2_2OR^3$, —$SiR^2_2OCOR^7$, —$SiR^2_2OC$=$CH_2CH_2$, —$SiR^2_2ON$=$CR^7R^8$, —$SiR^2_2NR^7R^8$, or any one of groups shown below:

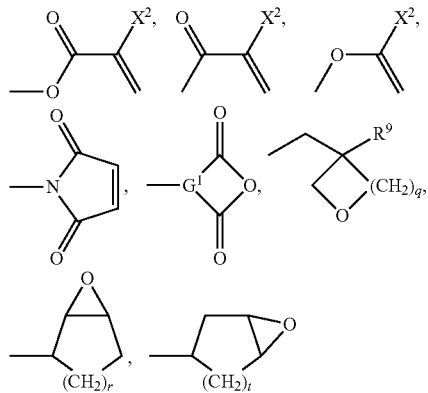

Codes in these groups related to $Y^1$ are defined as follows. $M^1$ is hydrogen or alkaline metal. $R^3$ is hydrogen, alkaline metal or alkyl having 1 to 10 carbon atoms. In the alkyl having 1 to 10 carbon atoms, optional —$CH_2$—, which is not adjacent to each other, may be replaced by —O—, and optional hydrogen may be replaced by halogen. $R^4$ is hydrogen, alkyl having 1 to 10 carbon atoms, cyclopropyl, cyclobutyl, cyclopentyl, cyclohexyl, cyclohexenyl, or phenyl in which optional hydrogen may be replaced by halogen, or alkyl having 1 to 5 carbon atoms. In the alkyl having 1 to 10 carbon atoms, optional —$CH_2$—, which is not adjacent to each other, may be replaced by —O—, and optional hydrogen may be replaced by halogen. In the alkyl having 1 to 5 carbon atoms which is a substituent of phenyl, optional —$CH_2$—, which is not adjacent to each other, may be replaced by —O—, —CH=CH—OC—C, and optional hydrogen may be replaced by halogen. $X^1$ is halogen, and chlorine and bromine are preferred. $R^5$, $R^6$ and $X^2$ are independently hydrogen, halogen, —CN, or alkyl having 1 to 10 carbon atoms the alkyl having 1 to 10 carbon atoms, optional —$CH_2$—, which is not adjacent to each other, may be replaced by —O—, and optional hydrogen may be replaced by halogen. The preferred examples of $R^5$, $R^6$ and $X^2$ are hydrogen, Methyl, —F, —$CF_3$ and phenyl. $R^7$ and $R^8$ are independently alkyl having 1 to 10 carbon atoms. $R^9$ is hydrogen or alkyl having 1 to 5 carbon atoms. The preferred examples of $R^9$ are hydrogen, methyl and ethyl. $G^1$ is a trivalent organic group. This is a part of a tetracarboxylic acid a residue when the compound having a PSQ skeleton is tetracarboxylic anhydride.

The preferred example of $Y^1$ is —$OM^1$, —CHO, —$COOR^3$, —$NHR^4$, —$COX^1$, —N=C=O, —$CR^5$=$CH_2$, 1,2-epoxycyclohexyl, 3,4-epoxycyclohexyl, or any one of groups shown below:

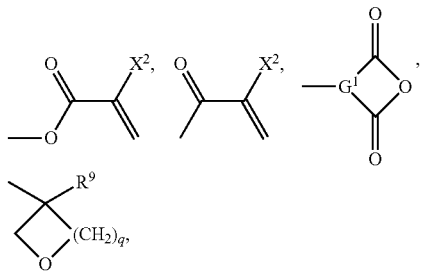

More preferred example of $Y^1$ is —$OM^1$, —$COOR^3$, —$NHR^4$, —$COX^1$, —N=C=O, —$CR^5$=$CH_2$, 1,2-epoxycyclohexyl, 3,4-epoxycyclohexyl, or any one of groups shown below:

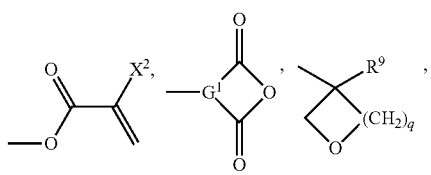

Further more preferred example of $Y^1$ is —OH, —$COOR^3$, —$NH_2$, —COCl, oxiranyl, oxetanyl or a group shown below:

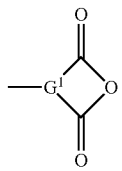

When $Y^1$ is an addition-polymerizable group, it is preferred that an addition-polymerizable group is not contained in $Q^1$ of Formula (1). It is preferred as well that an addition-polymerizable group is not contained in a substituent of a ring constituting $Q^2$. When $Y^1$ is a condensation-polymerizable group, it is preferred that $Q^1$ in Formula (1) is a group which do not react with $Y^1$. It is preferred as well that a group which reacts with $Y^1$ is not contained in a substituent of a ring constituting $Q^2$ and a bonding group connecting rings.

Formula (2) can be specified to preferred formulas such as Formula (1-1) to Formula (1-86) shown below. Codes in these formulas mean the same as described above. Groups showing 1,4-cyclohexylene, 1,4-phenylene and pyridine-2,5-diyl each represent groups shown by the following formulas:

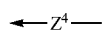 (1-1)

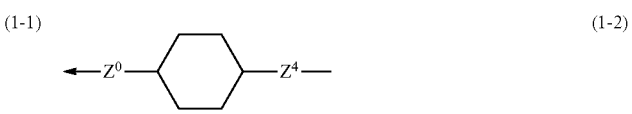 (1-2)

-continued
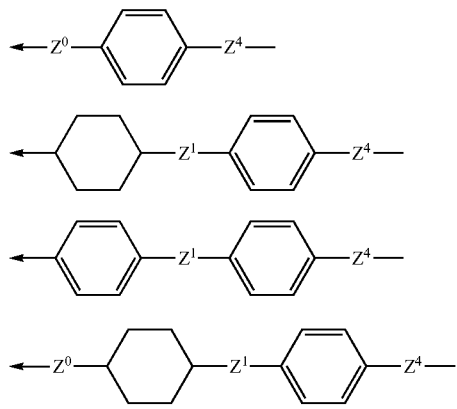(1-3)
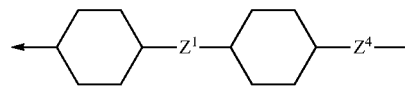(1-4)
(1-5)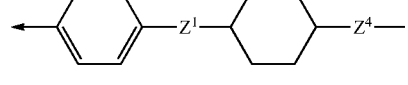(1-6)
(1-7)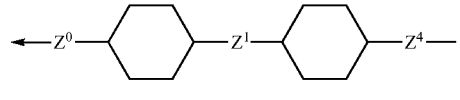(1-8)
(1-9)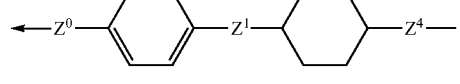(1-10)
(1-11)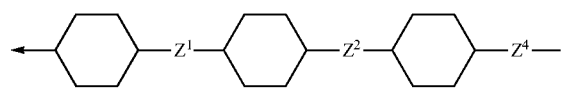(1-12)
(1-13)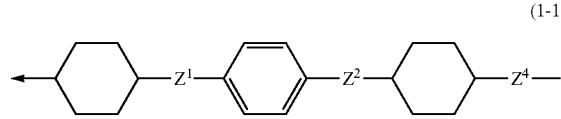(1-14)
(1-15)(1-16)
(1-17)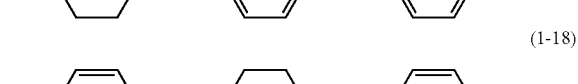(1-18)
(1-19)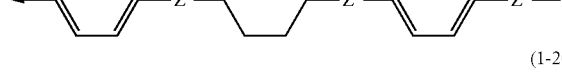(1-20)
(1-21)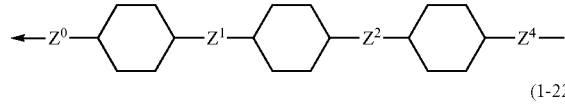(1-22)
(1-23)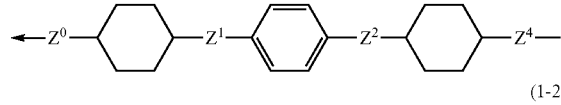(1-24)
(1-25)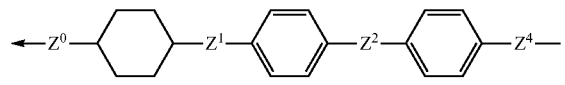(1-26)
(1-26b)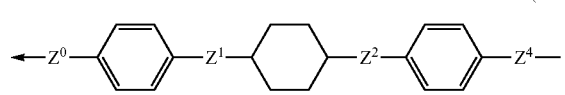(1-27)
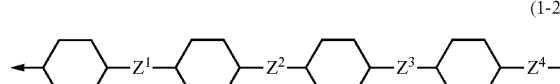(1-28)
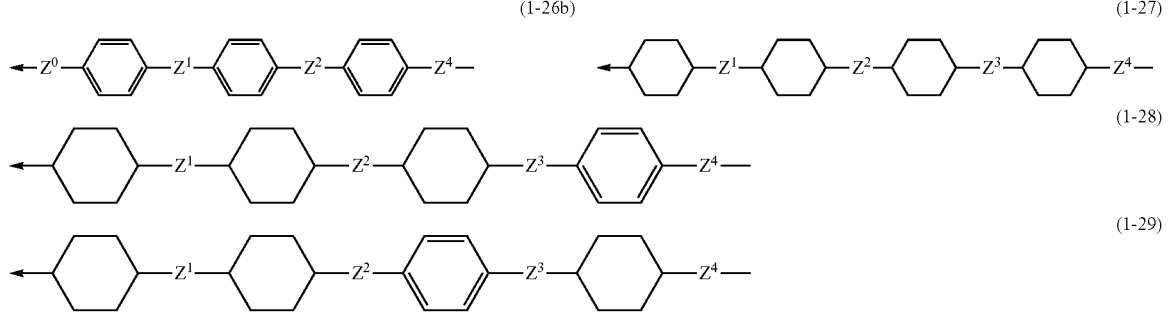(1-29)

-continued
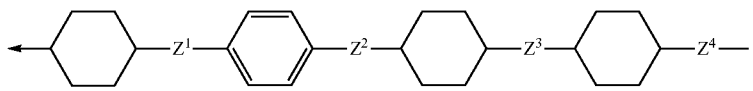
(1-30)
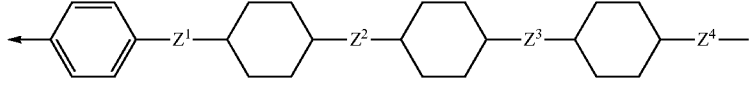
(1-31)
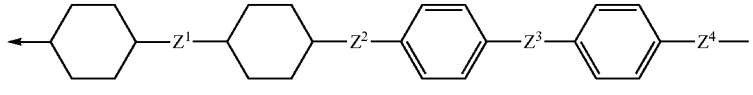
(1-32)
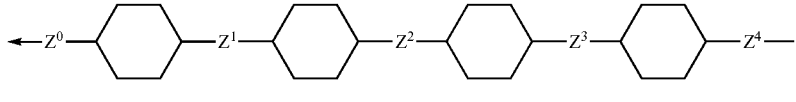
(1-33)
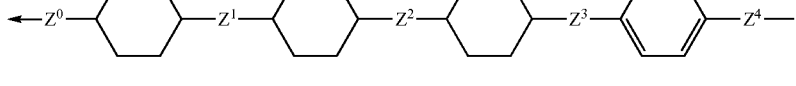
(1-34)
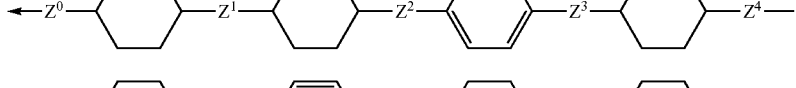
(1-35)
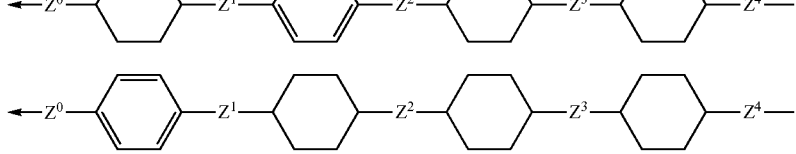
(1-36)
(1-37)
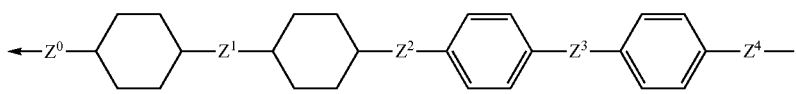
(1-38)
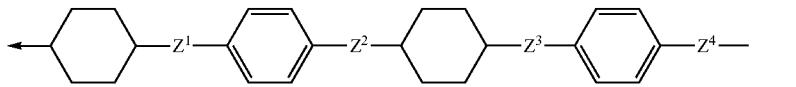
(1-39)
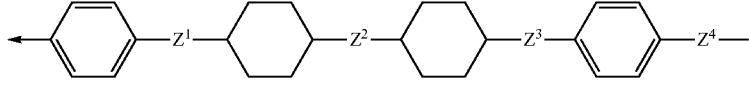
(1-40)
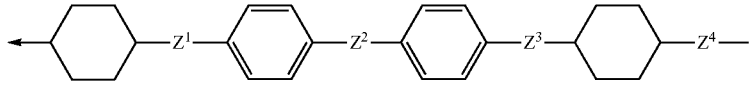
(1-41)
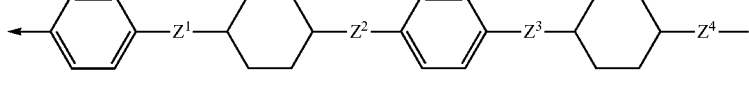
(1-42)
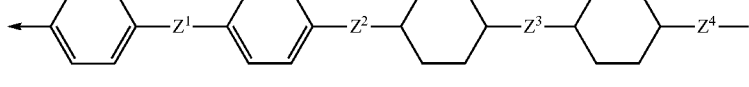
(1-43)
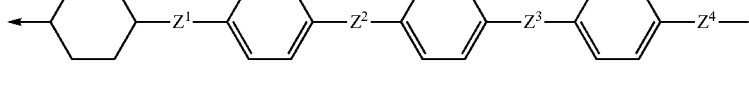
(1-44)
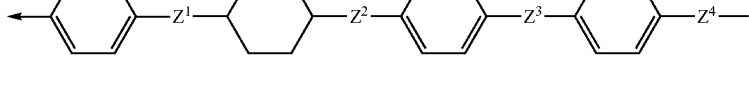
(1-45)

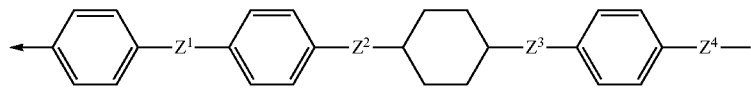
(1-46)
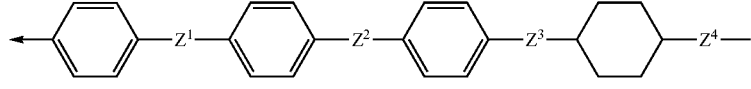
(1-47)
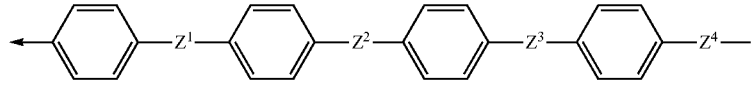
(1-48)
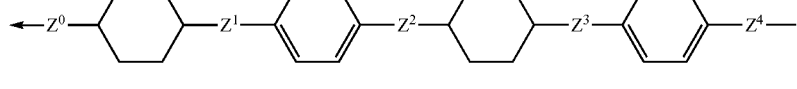
(1-49)
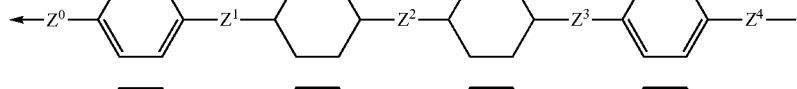
(1-50)
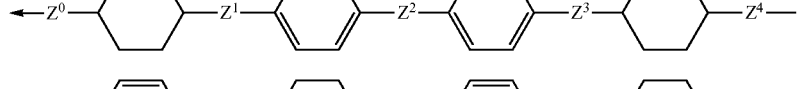
(1-51)
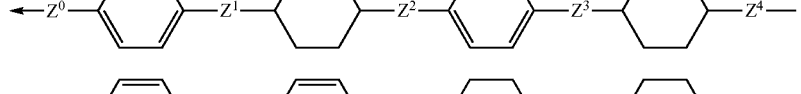
(1-52)
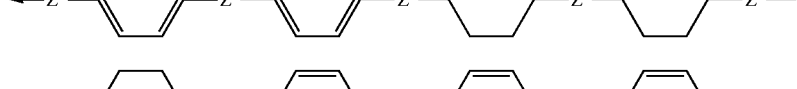
(1-53)
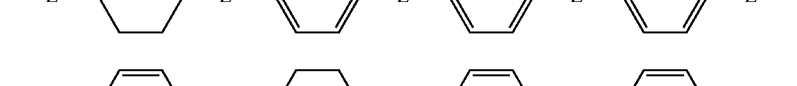
(1-54)
(1-55)
(1-56)
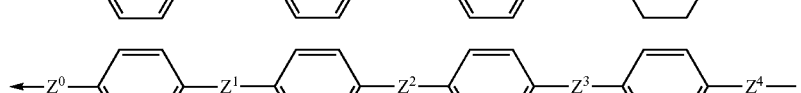
(1-57)
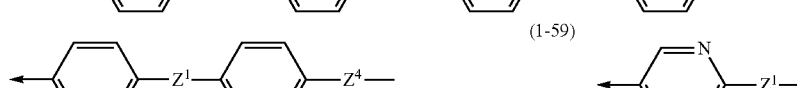
(1-58)
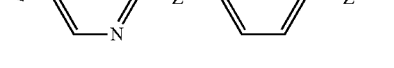
(1-59)
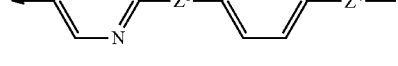
(1-60)
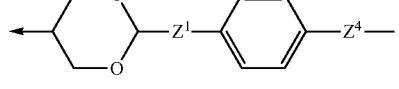
(1-61)
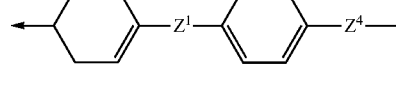
(1-62)
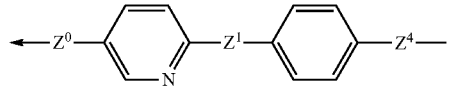
(1-63)
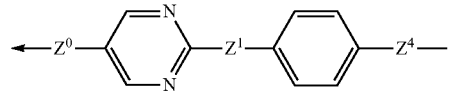
(1-64)

-continued
(1-65) 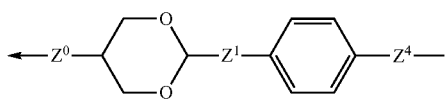
(1-66) 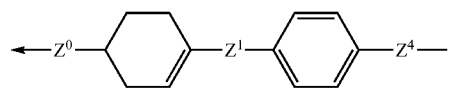
(1-67) 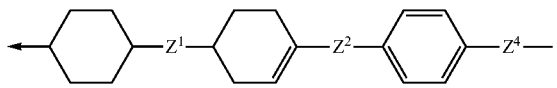
(1-68) 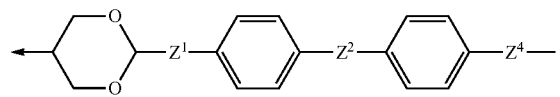
(1-69) 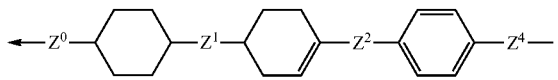
(1-70) 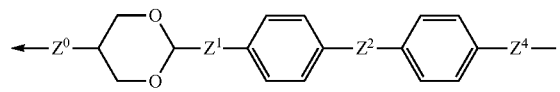
(1-71) 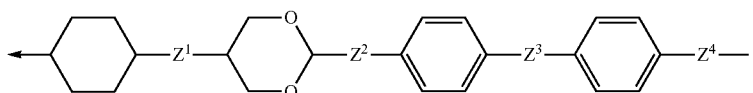
(1-72) 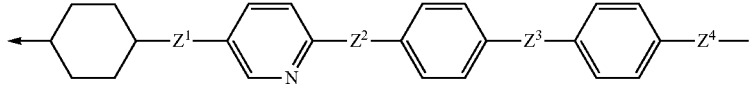
(1-73) 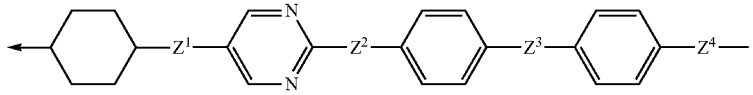
(1-74) 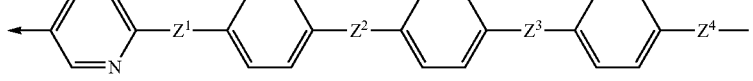
(1-75) 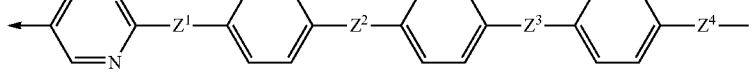
(1-76) 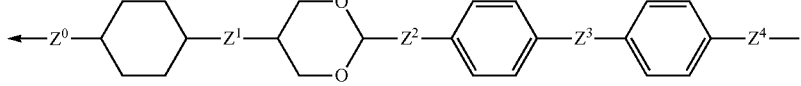
(1-77) 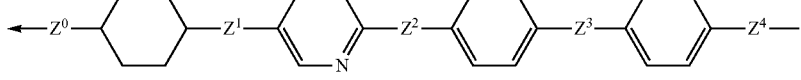
(1-78) 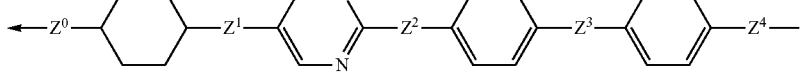
(1-79) 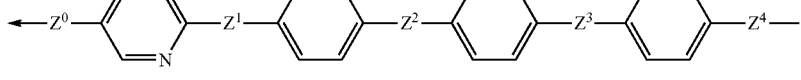
(1-80) 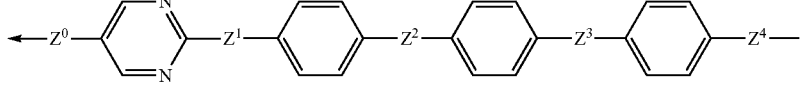
(1-81) 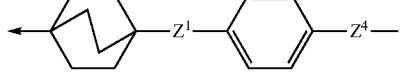
(1-82) 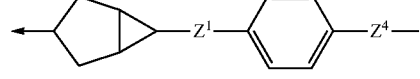

-continued
(1-83)
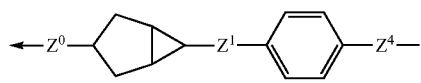
(1-84)
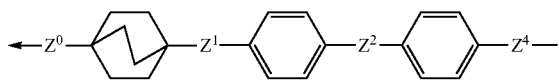
(1-85)
(1-86)
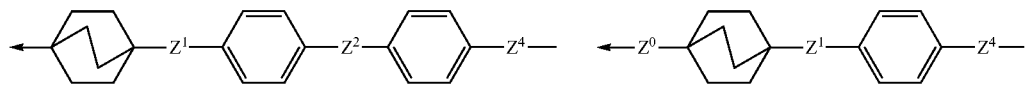
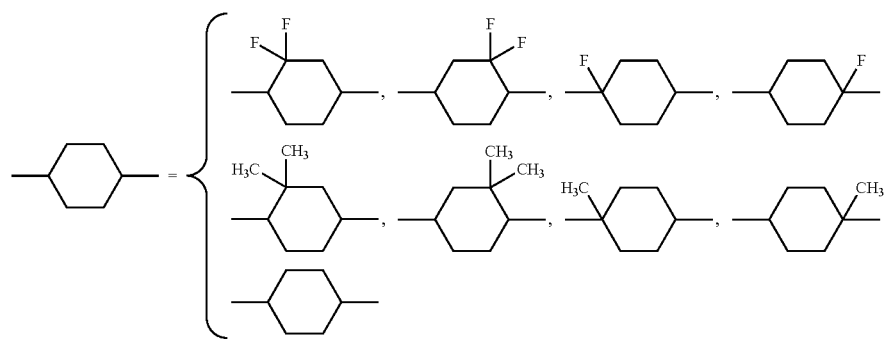
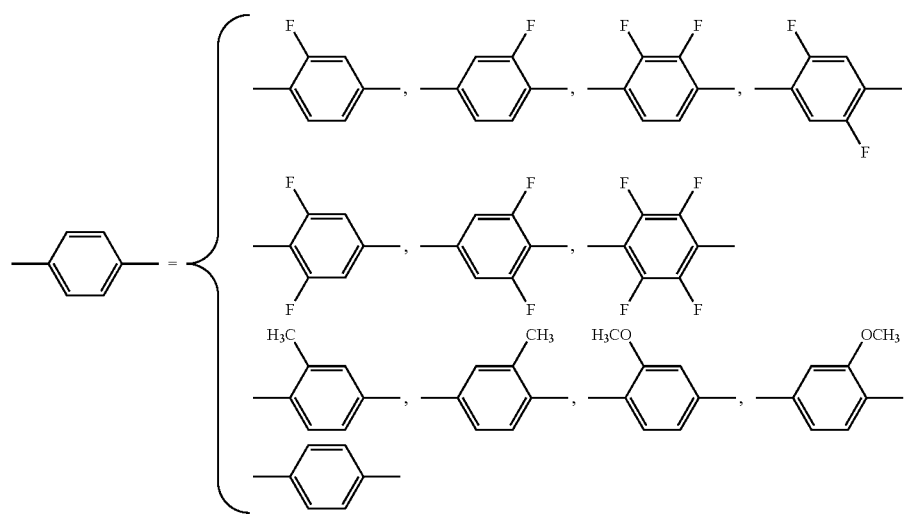
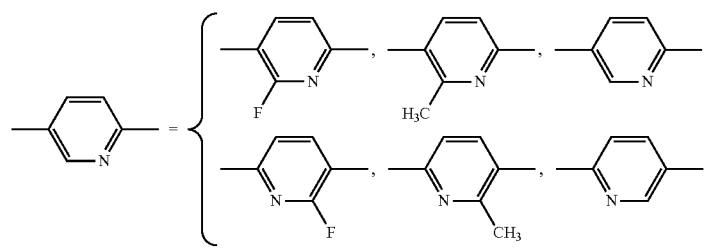

Among the above formulas, Formula (1-1) to Formula (1-80) are more preferred, and Formula (1-1) to Formula (1-58) are further more preferred.

Isotopes such as heavy hydrogen and $^{13}C$ may be contained in the compound (1) in a larger proportion than those of naturally present ones. In such case, the compounds make little difference in physical properties.

Next, the polymer of the present invention shall be explained. The polymer of the present invention is a polymer having a PSQ skeleton and has a structural unit represented by Formula (3):

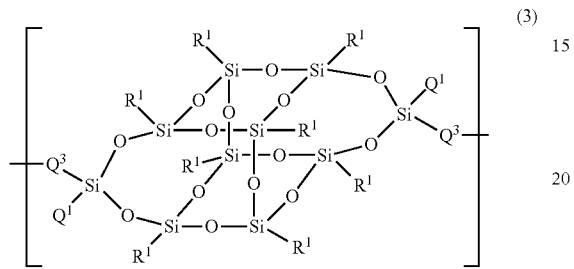

In Formula (3), $R^1$ and $Q^1$ are groups defined in the same manner as these codes in Formula (1), and the preferred examples of them are the same as in Formula (1). And, $Q^3$ is a group represented by Formula (4):

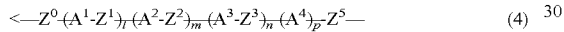

Codes in the formula are groups defined in the same manner as these codes in Formula (2) excluding $Z^5$, and the preferred examples of them are the same as in Formula (2). $Z^5$ is a single bond, —CH=CH—, —C≡C—, —COO—, —OCO—, or a group represented by —$W^1$-$T^1$-. $W^1$ is a single bond or alkylene having 1 to 20 carbon atoms. In the alkylene, optional —$CH_2$—, which is not adjacent to each other, may be replaced by —O—, —COO—, —OCO—, —CH=CH— or —C≡C—. The preferred example of $W^1$ is alkylene in which the number of carbon atoms is 1 to 20 and optional —$CH_2$—, which is not adjacent to each other, may be replaced by —O—, —COO— or —OCO—.

$T^1$ is —O—, —S—, —$OSiR^2_2$—, —$OSiR^2_2O$—, —$SiR^2_2OSiR^2_2$—, —CO—, —COO—, —OCO—, —CSO—, —OCS—, —$CONR^{10}$—, —$NR^{10}CO$—, —$CONR^{10}O$—, —$ONR^{10}CO$—, —$OCONR^{10}$—, —$NR^{10}CONR^{10}$—, —$NR^{10}COO$—, —OCOO—, —CH(OH)$CH_2$—, —$CH_2$CH(OH)—, —CH=CH—, —$CH_2CR^5$=$CR^6CH_2$—, —$SO_2$—, —$SO_2O$—, —$OSO_2$—, —$SO_2S$—, —$SSO_2$—, —$SO_2NR^{10}$—, —$NR^{10}SO_2$—, or any one of groups shown below:

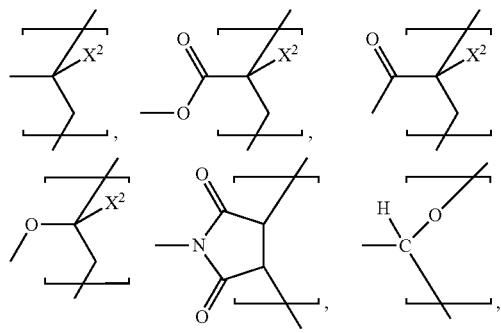

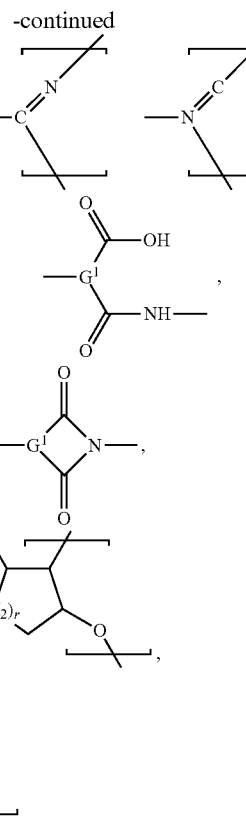

In these groups related to $T^1$, $R^2$ is the same as described above. $R^{10}$ is hydrogen, alkyl having 1 to 10 carbon atoms, cyclopropyl, cyclobutyl, cyclopentyl, cyclohexyl, cyclohexenyl, or phenyl in which optional hydrogen may be replaced by halogen or alkyl having 1 to 5 carbon atoms. In the alkyl having 1 to 10 carbon atoms, optional hydrogen may be replaced by halogen. In the alkyl having 1 to 5 carbon atoms which is a substituent of phenyl, optional —$CH_2$—, which is not adjacent to each other, may be replaced by =O—, —CH=CH— or —C, and optional hydrogen may be replaced by halogen. The preferred examples of $R^{10}$ are hydrogen, methyl, ethyl, propyl, cyclopropyl, cyclobutyl, cyclopentyl, cyclohexyl and phenyl. $R^5$, $R^6$ and $X^2$ have the same meanings as these codes in the definitions related to $Y^1$, and the preferred examples thereof are the same as described above.

$G^1$ is a trivalent organic group. This is a part of tetracarboxylic acid's residue when the structural unit having a PSQ skeleton is derived from tetracarboxylic acid-derivative having a PSQ skeleton. $G^2$ is a part of tricarboxylic acid-derivative's residue or a part of tetracarboxylic acid-derivative's residue. This shows a part of polybasic acid-derivative's residue which are the target of the reaction when the structural unit having a PSQ skeleton is derived from diamine having a PSQ skeleton. The structural unit in which $T^1$ is a group containing $G^1$ is derived by the reaction of tetracarboxylic acid-derivative having a PSQ skeleton with diamine. This diamine may be diamine having a PSQ skeleton or diamine having no PSQ skeleton. The structural unit in which $T^1$ is a group containing $G^2$ is derived by the reaction of diamine having a PSQ skeleton with polybasic acid-derivative. The polybasic acid-derivative may be tetracarboxylic acid-derivative having a PSQ skeleton, or tricarboxylic acid-derivative or tetracarboxylic acid-derivative having no PSQ skeleton. The term "tetracarboxylic acid-derivative(s)" is used as a general term including ester, acid anhydride and acid halide of tetracarboxylic acid in addition to tetracarboxylic acid, in the present invention. Polybasic acid-derivative(s), tricarboxylic acid-derivative(s) and dicarboxylic acid-derivative(s) are terms defined in the same manner as described above.

The compound (1) can be produced by reacting a compound (1a) with dichlorosilane (1b) in the presence of a base such as triethylamine:

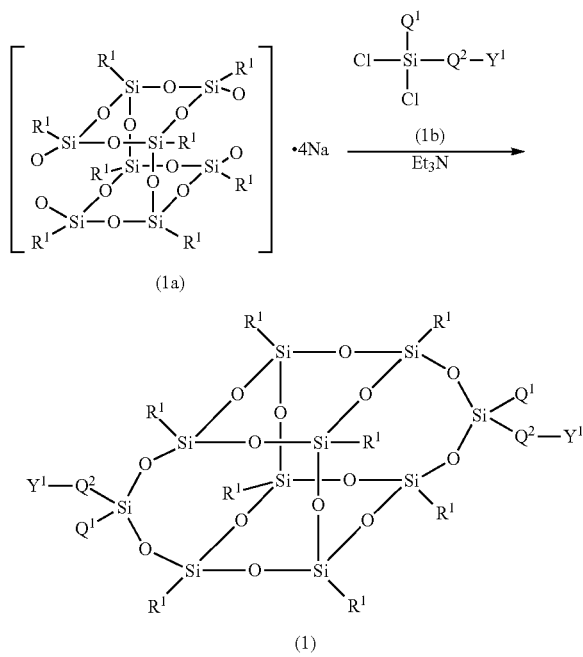

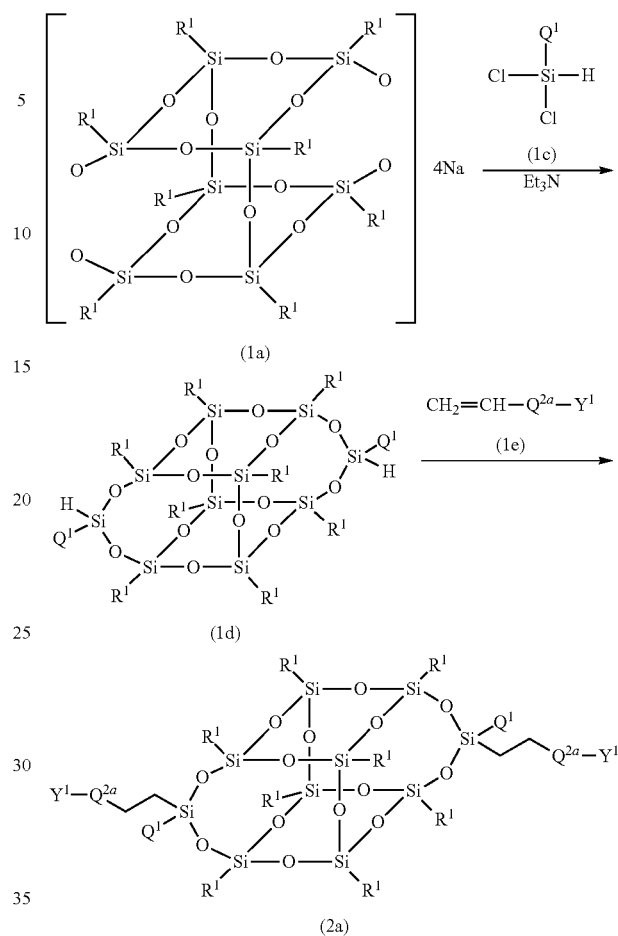

In this scheme, $Et_3N$ is triethylamine, and the other codes have the same meanings as described above. The compound (1a) can be produced by subjecting a silane compound $R^1SiA_3$ to hydrolysis and condensation polymerization in the presence of monovalent alkaline metal hydroxide and water, in the presence or absence of an organic solvent. A is a hydrolyzable group and is preferably chlorine and alkoxy having 1 to 4 carbon atoms. The examples of the monovalent alkaline metal hydroxide are lithium hydroxide, sodium hydroxide, potassium hydroxide and cesium hydroxide. Among them, sodium hydroxide and potassium hydroxide are preferred. The amount of the monovalent alkaline metal hydroxide used is 0.3 to 1.5 in terms of a mole ratio based on the silane compound described above, and more preferred mole ratio is 0.4 to 0.8. The amount of water added is 1:0 to 1.5 in terms of a mole ratio based on the silane compound, and more preferred mole ratio is 1.1 to 1.3. The preferred examples of the organic solvent are linear, branched or cyclic monovalent alcohols. It is estimated that alcohol contributes to a control of the structure in a condensing step.

The compound (1a) is reacted with dichlorosilane (1c) to prepare a compound (1d), and then the compound (1d) may be reacted with a compound (1e) in the presence of a catalytic amount of a radical polymerization initiator (azobisisobutyronitrile, benzoyl peroxide, di-t-butyl peroxide and the like) or a transition metal compound (Pt, Rh, Pd, Ni and the like). Thus, a compound (2a) is obtained.

In the scheme described above, $G^{2a}$ is a group represented by Formula (5), and the other codes have the same meanings as described above.

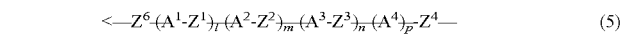

In Formula (5), l, m, n and p are independently 0, 1, 2 or 3, and $Z^6$ is a single bond, —CH═CH—, ═C—, —COO—; —OCO—, or alkylene having 1 to 18 carbon atoms. In the alkylene, optional —CH$_2$— may be replaced by —O—, —S—, —NH—, —SiR$^2_2$—, —SiR$^2_2$O—, —OSiR$^2_2$—, —OSiR$^2_2$O—, —SiR$^2_2$OSiR$^2_2$═C—COO—, —OCO—, —CH═CH— or —C One example of a method for forming the bonding group $Z^1$, $Z^2$, $Z^3$, $Z^4$ or $Z^6$ shall be explained by showing a scheme. $MSG^1$ and $MSG^2$ in the following scheme each are monovalent or divalent organic groups having at least one ring. Plural $MSG^1$ (or $MSG^2$) in the scheme may be the same or different. A compound (1A) to a compound (1H) correspond to the compound (I).

(I) Formation of single bond

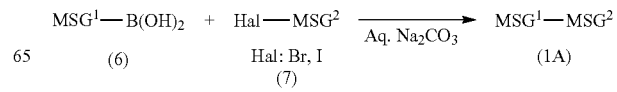

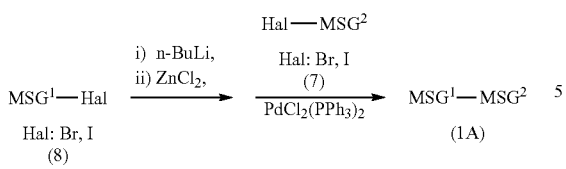

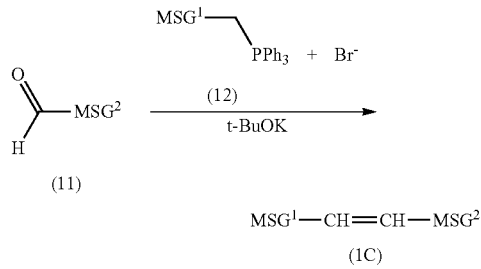

A boric acid derivative (6) and a halide (7) synthesized by a publicly known method are reacted in a carbonate aqueous solution in the presence of a catalyst such as tetrakis(triphenylphosphine)-palladium to synthesize a compound (1A). This compound (1A) can be synthesized as well by first reacting n-butyllithium with a compound (8) synthesized by a publicly known method, then reacting zinc chloride and further reacting the compound (7) in the presence of a catalyst such as dichlorobis-(triphenylphosphine)palladium. The boric acid derivative (6) can be produced by deriving the compound (8) into a Grignard reagent or a lithium reagent and reacting it with trialkylboric acid ester.

(II) Formation of —COO— and —OCO—

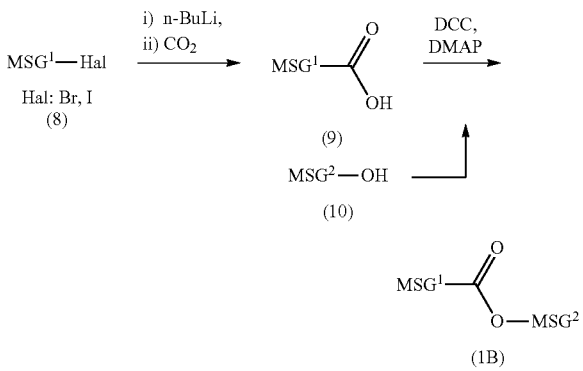

The compound (8) is reacted with n-butyllithium and then carbon dioxide to obtain a carboxylic acid (9). The carboxylic acid (9) is dehydrated with phenol (10) synthesized by a publicly known method, in the presence of DCC (1,3-dichlorohexylcarbodiimide) and DMAP (4-dimethylaminopyridine) to synthesize a compound (1B) having —COO—. A compound having —OCO— can be synthesized as well by the method.

(III) Formation of —CH=CH—

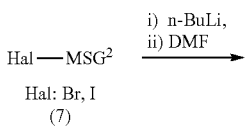

The compound (7) is treated with n-butyllithium and then reacted with formamide such as N,N-dimethyl-formamide to obtain aldehyde (11). A phosphonium salt (12) synthesized by a publicly known method is treated with a base such as potassium t-butoxide to produce phosphorus ylid, and this is reacted with the aldehyde (11) to synthesize a compound (1C). The cis compound is formed depending on the reaction conditions, and therefore the cis compound is isomerized, if necessary, to the trans compound by a publicly known method.

(IV) Formation of —(CH$_2$)$_2$—

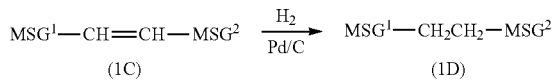

The compound (1C) is hydrogenated in the presence of a catalyst such as palladium carbon to thereby synthesize a compound (1D).

(V) Formation of —(CH$_2$)$_4$—

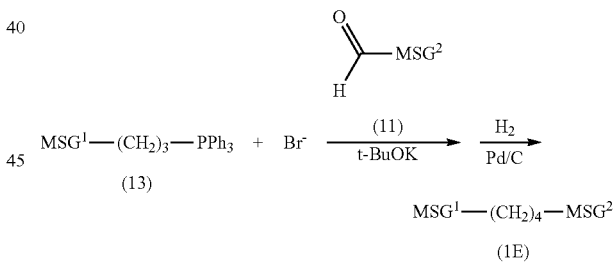

A phosphonium salt (13) is used in place of the phosphonium salt (12) to obtain a compound having —(CH$_2$)$_2$—CH=CH— according to the method described in the item (III). This is catalytically hydrogenated to synthesize a compound (1E).

(VI) Formation of ≡C—

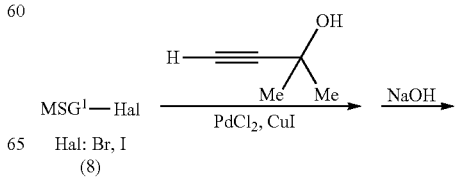

-continued

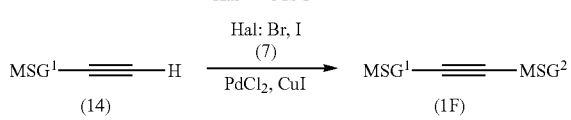

The compound (8) is reacted with 2-methyl-3-butyne-2-ol in the presence of a catalyst of dichloropalladium and copper halide, and then the compound is deblocked on a basic condition to obtain a compound (14). The compound (14) is reacted with the compound (7) in the presence of a catalyst of dichloropalladium and copper halide to synthesize a compound (1F).

(VII) Formation of —CH₂O— or —OCH₂—

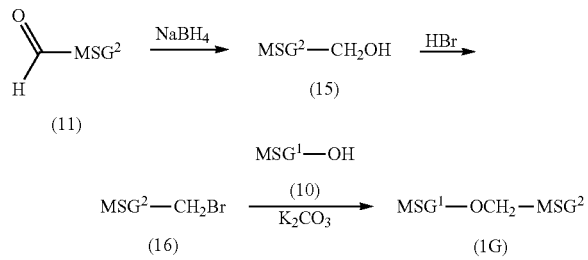

The compound (11) is reduced by a reducing agent such as sodium boron hydride to obtain a compound (15). This is halogenated with hydrobromic acid to obtain a compound (16). The compound (16) is reacted with the compound (10) in the presence of potassium carbonate to synthesize a compound (1G).

(VIII) Formation of —(CH₂)₃O— or —O(CH₂)₃—

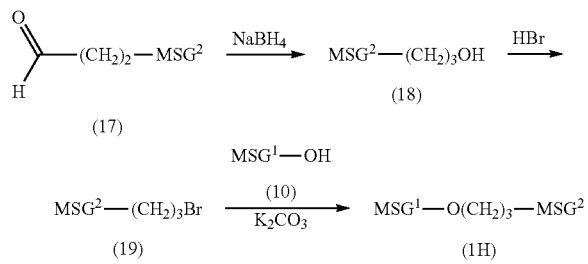

A compound (17) is used in place of the compound (11) to synthesize a compound (1H) according to the method described in the item (VII).

In addition to the examples described above, the compound (1) can be produced by using freely synthetic methods in organic chemistry which are described in Houben-Wyle, Methods of Organic Chemistry, George Thieme Verlag, Stuttgart, Organic Syntheses, John Wiley & Sons Inc., Organic Reactions, John Wiley & Sons Inc., Comprehensive Organic Synthesis, Pergamon Press, and New Experimental Chemical Course (Maruzen).

Next, the polymer of the present invention shall be explained. The homopolymer is obtained by polymerizing only one compound (1). A copolymer of the compound (1) is obtained by polymerizing a polymerizable composition containing at least two compounds (1). The copolymer is obtained as well by polymerizing a polymerizable composition containing the compound (1) and other polymerizable compounds. All of these homopolymer and copolymers have almost the same structural unit as the structural unit represented by Formula (3). A configuration of the structural unit in the copolymer may be any one of random, block, alternation and graft.

The polymer is obtained by subjecting the compound (1) or a polymerizable composition containing the compound (1) to addition polymerization or condensation polymerization. That is, when the functional group $Y^1$ in the compound (1) is an addition-polymerizable group, it is addition-polymerized by heat or light. When $Y^1$ is a condensation-polymerizable group, it is condensation-polymerized with a compound having at least two functional groups which can be reacted with $Y^1$. The polymerizable composition containing the compound (1) is preferably an addition-polymerizable composition or a condensation-polymerizable composition.

The addition-polymerizable composition is a composition containing the compound (1) having an addition-polymerizable group and further containing other addition-polymerizable compounds. The other addition-polymerizable compound may be another compound (1) having an addition-polymerizable group or may be an addition-polymerizable compound which is not the compound (1). They may be blended all together. In the following explanations, the addition-polymerizable compound other than the compound (1) shall be referred to as the other polymerizable compound. The condensation-polymerizable composition is a composition containing the compound (1) having a condensation-polymerizable group and further containing other condensation-polymerizable compounds having at least two functional groups which are reacted with the functional group. The other condensation-polymerizable compound may be another compound (1) having a condensation-polymerizable group, or may be a compound other than the compound (1). They may be blended all together. In the following explanations, the condensation-polymerizable compound other than the compound (1) shall be referred to as the other reactive compound.

When the addition-polymerizable composition is subjected to heat polymerization, the reaction temperature is 0 to 300° C., and the reaction time is 1 to 100 hours. Usually, a radical polymerization initiator is used. The examples of the radical polymerization initiator are benzoyl peroxide, diisopropyl peroxydicarbonate, t-butyl peroxy-2-ethylhexanoate, butyl peroxypivalate, t-butyl peroxydiisobutylate, lauroyl peroxide, dimethyl 2,2'-azobisisobutyrate(MAIB), di-t-butyl peroxide (DTBPO), azobisisobutyronitrile (AIBN) and azobiscyclohexanecarbonitrile (ACN).

When the addition-polymerizable composition is polymerized by irradiation with light or an electron beam, a radical photopolymerization initiator may be used. Darocure 1173 (2-hydroxy-2-methyl-1-phenylpropane-1-one), Irgacure 184 (1-hydroxycyclohexyl phenyl ketone), Irgacure 651 (2,2-dimetoxy-1,2-diphenylethane-1-one), Irgacure 500, Irgacure 2959, Irgacure 907, Irgacure 369, Irgacure 1300, Irgacure 819, Irgacure 1700, Irgacure 1800, Irgacure 1850, Darocure 4265 and Irgacure 784, among the products of Ciba Specialty Chemicals Co., Ltd., can be given as the examples of the radical photopolymerization initiatorare.

The other examples of the radical photopolymerization initiator are p-methoxyphenyl-2,4-bis(trichloromethyl)triazine, 2-(p-butoxystyryl)-5-trichloromethyl-1,3,4-oxadiazole, 9-phenylacridine, 9,10-benzphenazine, a mixture of benzophenone/Michler's ketone, a mixture of hexaarylbiimidazole/mercaptobenzimidazole, 1-(4-isopropylphenyl)-2-hydroxy-2-methylpropane-1-one, benzyldimethylketal, 2-methyl-1-[(4-(methylthio)phenyl]-2-morpholinopropane-1-one, and a mixture of 2,4-diethylxanthone/methyl p-dimethylaminobenzoate.

Used for the condensation polymerization reaction are a method in which the raw materials are reacted in a solution state, a method in which the raw materials are reacted in a molten state, a method in which the raw materials are reacted in a vaporized state by heating under reduced pressure and a method in which they are reacted by giving energy such as light, supersonic wave and plasma from the outside to activate them. Usually, a polymerization accelerator such as acid, alkali, metal compounds and the like is used for the purpose of accelerating the polymerization reaction. For example, polyester is produced by esterification or transesterification. The examples of the polymerization accelerator in the reaction are simple substances such as alkaline metals, alkaline earth metals, tin, germanium, antimony, zinc, cobalt, nickel, titanium and aluminum, and compounds thereof. The examples of the compounds are oxides, hydroxides, halides, carbonates, hydrogencarbonates and acetates. Inorganic acid salts, organic acid salts and complexes of the alkylated compounds thereof can be given.

The examples of the germanium compounds are germanium dioxide, germanium tetraethoxide and germanium tetra-n-butoxide. The examples of the titanium compounds are tetraalkyl titanate (tetraethyl titanate, tetraisopropyl titanate, tetra-n-propyl titanate, tetra-n-butyl titanate and the like) and partially hydrolyzed products thereof, titanyl oxalate compounds (titanyl oxalate, ammonium titanyl oxalate, sodium titanyl oxalate, potassium titanyl oxalate, calcium titanyl oxalate, strontium titanyl oxalate and the like), titanium trimellitate, titanium sulfate and titanium chloride. The examples of the antimony compounds are antimony trioxide, antimony acetate, antimony tartarate, potassium antimony tartarate, antimony oxychloride, antimony glycolate, antimony pentaoxide and triphenylantimony. The examples of the aluminum compounds are aluminum carboxylate (aluminum formate, aluminum acetate, aluminum propionate, aluminum oxalate and the like), aluminum oxide, aluminum hydroxide, aluminum chloride, chloroaluminum hydroxide, aluminum carbonate, aluminum alkoxides (aluminum methoxide, aluminum ethoxide and the like), aluminum acetylacetonate or aluminum chelate compounds with aluminum acetylacetonate; organic aluminum compounds (trimethylaluminum, triethylaluminum and the like) and partially hydrolyzed products thereof.

A stabilizer can be used as well in addition to the polymerization accelerating agent. The examples of the stabilizer are phosphoric acid esters (trimethyl phosphate, triethyl phosphate, tri-n-butyl phosphate, trioctyl phosphate, triphenyl phosphate, methyl acid phosphate, isopropyl acid phosphate, butyl acid phosphate, dibutyl phosphate, monobutyl phosphate, dioctyl phosphate and the like), phosphorous acid esters (triphenyl phosphite, trisdodecyl phosphite, trisnonylphenyl phosphite and the like) and phosphoric acid and polyphosphoric acid.

For example, polyimide can be produced by subjecting diamine and tetracarboxylic dianhydride to condensation polymerization to prepare polyamic acid and then dehydrating it by a thermal imidation method or a chemical imidation method. Usually, a reaction temperature in the thermal imidation method is 50 to 300° C. A dehydrating agent or a basic catalyst having a hydrolyzing ability is used in the chemical imidation method. The examples of the dehydrating agent are N,N-dialkylcarbodiimides, aliphatic carboxylic anhydrides (acetic anhydride, trifluoroacetic anhydride and the like), phosphoric acid derivatives (polyphosphoric acid, phosphorus pentaoxide and the like), acid anhydrides of phosphoric acid derivatives and acid chlorides (methanesulfonyl chloride, phosphorus pentachloride, thionyl chloride and the like). The examples of the basic catalyst are organic bases, tertiary amines and inorganic bases. The examples of the organic bases are N,N-dimethylacetamide, N,N-diethylacetamide, N,N-dimethylformamide, N,N-diethylformamide, N-methyl-2-pyrrolidone, 1,3-dimethyl-2-imidazolidinone, imidazole, N-methylcaprolactam, imidazole, N,N-dimethylaniline and N,N-diethylaniline. The examples of the tertiary amines are pyridine, collidine, lutidine and triethylamine. The examples of the inorganic bases are potassium hydroxide, sodium hydroxide, potassium carbonate, sodium carbonate, potassium hydrogencarbonate and sodium hydrogencarbonate.

The epoxy resin is obtained from an epoxy composition containing at least one epoxy compound and a curing agent or a cationic photopolymerization initiator. The epoxy composition may contain, if necessary, a solvent and/or a curing-accelerating agent. The curing-accelerating agent accelerates the reaction of the epoxy compound with the curing agent. The specific examples of the cationic photopolymerization initiator shall be shown below. Almost all of them are commercially available and can readily be obtained.

The examples of the cationic photopolymerization initiator are diaryliodonium salts (hereinafter abbreviated as DAS) and triarylphosphonium salts (hereinafter abbreviated as TAS). The examples of DAS are diphenyliodonium tetrafluoroborate, diphenyliodonium hexafluorophosfonate, diphenyliodonium hexafluoroarsenate, diphenyliodonium trifluoromethanesulfonate, diphenyliodonium trifluoroacetate, diphenyliodonium p-toluenesulfonate, diphenyliodonium tetra(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoroarsenato, 4-methoxyphenylphenyliodonium trifluoromethanesulfonate, 4-methoxyphenylphenyliodonium trifluoroacetate, 4-methoxyphenylphenyliodonium p-toluenesulfonate, 4-methoxyphenylphenyliodonium diphenyliodonium tetra(pentafluorophenyl)borate, bis(4-tert-butylphenyl)iodonium diphenyliodonium tetrafluoroborate, bis(4-tert-butylphenyl)Iodonium diphenyliodonium hexafluoroarsenate, bis(4-tert-butylphenyl)iodonium diphenyliodonium trifluoromethanesulfonate, bis(4-tert-butylphenyl)Iodonium trifluoroacetate, bis(tert-butylphenyl)iodonium p-toluenesulfonate and bis(4-tert-butylphenyl) Iodonium diphenyliodonium tetra(pentafluorophenyl)borate.

DAS can be highly sensitized by adding a photosensitizer. The examples of the photosensitizer are thioxanthone, phenothiazine, chlorothioxanthone, xanthone, anthracene, diphenylanthradene and rubrene.

The examples of TAS are triphenylsulfonium tetrafluoroborate, triphenylsulfonium hexafluorophosphonate, triphenylsulfonium hexafluoroarcenate, triphenylsulfonium trifluoromethanesulfonate, triphenylsulfonium trifluoroacetate, triphenylsulfonium p-toluenesulfonate, triphenylsulfonium tetra(pentafluorophenyl)borate, 4-methoxyphenyl-diphenylsulfonium tetrafluoroborate, 4-methoxyphenyl-diphenylsulfonium hexafluorophosphonate, 4 methoxyphenyldiphenylsulfonium hexafluoroarcenate, 4-methoxyphenyldiphenylsulfonium trifluoromethane-sulfonate, 4-methoxyphenyldiphenylsulfonium trifluoroacetate, 4-methoxyphenyldiphenylsulfonium p-toluenesulfonate, 4-methoxyphenyldiphenylsulfonium triphenylsulfonium tetra(pentafluorophenyl)borate, 4-phenylthiophenyldiphenylsulfonium tetrafluoroborate, 4-phenylthiophenyldiphenylsulfonium hexafluoro-phosphonate, 4-phenylthiophenyldiphenylsulfonium hexafluoroarcenate, 4-phenylthiophenyldiphenyl-sulfonium trifluoromethanesulfonate, 4-phenylthiophenyldiphenylsulfonium p-toluenesulfonate and 4-phenylthiophenyldiphenylsulfonium tetra(pentafluorophenyl)borate.

Publicly known potential curing agents which are usually used as a curing agent for epoxy resins can be used as the curing agent. The examples of the potential curing agents for epoxy resins are amine base curing agents, novolak resin base curing agents, imidazole base curing agents and acid anhydride base curing agents. The examples of the amine base curing agents are aliphatic polyamines (diethylenetriamine, triethylenetetraamine, tetraethylenepentaamine, m-xylenediamine, trimethylhexamethylenediamine, 2-methylpentamethylenediamine, diethylaminopropylamine and the like), alicyclic polyamines (isophoronediamine, 1,3-bisaminomethylcyclohexane, bis(4-aminocyclohexyl)methane, norbornenediamine, 1,2-diaminocyclohexane, Laromine and the like), aromatic polyamines (diaminodiphenylmethane, diaminodiphenyl ether, metaphenylenediamine, diaminodiphenylsulfone and the like), polyoxypropylenediamine, polyoxypropylenetriamine; polycyclohexylpolyamine mixtures and N-aminoethylpiperazine.

The examples of the novolak resin base curing agents are phenol novolak resins, bisphenol novolak resins, poly(p-vinylphenol) and the like. The examples of the imidazole base curing agents are 2-methylimidazole, ethylhexylimidazole, 2-undecylimidazole, 2-phenylimidazole, 1-cyanoethyl-2-phenylimidazolium trimellitate and 2-phenylimidazoliumisocyanurate.

The examples of the acid anhydride base curing agents include tetrahydrophthalic anhydride, hexahydrophthalic anhydride, methyltetrahydrophthalic anhydride, methylhexahydrophthalic anhydride, methylnadic anhydride, hydrogenate methylnadic anhydride, trialkyltetrahydrophthalic anhydride, methylcyclohexanetetracarboxylic dianhydride, phthalic anhydride, trimellitic anhydride, pyromellitic anhydride, benzophenonetetracarboxylic dianhydride, ethylene glycol bisanhydrotrimellitate, glycerinbis(anhydrotrimellitate) monoacetate, dodecenylsuccinic anhydride, aliphatic dibasic polyanhydride and chlorendic anhydride. The other curing agents include dicyandiamide, ketimine compounds and the like.

The examples of the curing-accelerating agent for accelerating the curing reaction of the epoxy compound with the curing agent are tertiary amines (benzyldimethylamine, tris(dimethylaminomethyl)phenol, dimethylcyclohexylamine and the like), imidazoles (1-cyanoethyl-2-ethyl-4-methylimidazole, 2-ethyl-4-methylimidazole, 1-benzyl-2-methylimidazole and the like), organic phosphorus base compounds (triphenylphosphine, triphenyl phosphite and the like), quaternary phosphonium salts (tetraphenylphosphonium bromide, tetra-n-butylphosphonium bromide and the like), diazabicycloalkenes (1,8-diazabicyclo[5.4.0]undecene-7 and organic acid salts thereof and the like), organic metal compounds (zinc octylate, tin octylate and aluminum acetylacetone complexes thereof and the like), quaternary ammonium salts (tetraethylammonium bromide, tetrabutylammonium bromide and the like), boron compounds (boron trifluoride, triphenyl borate and the like) and metal halide compounds (zinc chloride, stannic chloride and the like). The curing-accelerating agents which can be used in the present invention shall not be restricted to the above examples. The above curing-accelerating agents can be used alone or in a mixture of two or more kinds thereof.

A method for producing the epoxy resin shall not specifically be restricted, and it can be produced by a publicly known method, for example, by blending an epoxy compound, a curing agent, a curing-accelerating agent or a cationic photopolymerization initiator and, if necessary, additives and mixing them by a publicly known method. Also, the epoxy resin can be produced by preparing two liquids of an epoxy composition comprising an epoxy compound as a principal component and a curing-agent composition comprising a curing agent and a curing-accelerating agent as principal components and mixing the epoxy composition with the curing agent composition prior to use. Further, the epoxy resin can be produced as well by blending all of an epoxy compound, a curing agent, a curing-accelerating agent or a cationic photopolymerization initiator and, if necessary, additives in the form of a single liquid.

The examples of the epoxy compound other than the compound (1) used for the epoxy composition are glycidyl ethers-(bisphenol A diglycidyl ether, bisphenol S diglycidyl ether, novolak glycidyl ether, brominated bisphenol A diglycidyl ether and the glycidyl esters (glycidyl hexahydrophthalate, dimer acid glycidyl ester and the like), glycidylamines (triglycidyl isocyanurate, tetraglycidyl-diaminodiphenylmethane, triglycidylparaminophenol, tetraglycidylbisaminomethylcyclohexanone, N,N,N',N'-tetraglycidyl-m-xylenediamine and the like) and alicyclic or aliphatic epoxides (3,4-epoxycyclohexylmethyl carboxylate, epoxidized polybutadiene, epoxidized soy bean oil and the like).

A method for curing the epoxy composition shall not specifically be restricted, and capable of being used are publicly known curing apparatuses such as a closed type curing furnace and a tunnel furnace in which continuous curing can be carried out. The heating source shall not specifically be restricted, and heating can be carried out by publicly known methods such as hot air circulating, infrared heating and high-frequency heating. The curing temperature and the curing time fall preferably in the ranges of 80 to 250° C. and 30 seconds to 15 hours.

The polymer (3) can be produced as well by an anionic polymerization method, a coordinate polymerization method or a living polymerization method. The examples of the preferred catalyst used in these polymerization methods are alkyl alkaline metals (n-butyllithium, sec-butyllithium, t-butyllithium, trialkylaluminum and the like), aluminum compound and transition metal compound.

A solvent may be used for the polymerization reaction. The examples of the solvent are benzene, toluene, xylene, mesitylene, pentane, hexane, heptane, octane, nonane, decane, N,N-dimethylacetamide, N,N-diethylacetamide, N,N-dimethylformamide, N,N-diethylformamide, N-methyl-2-pyrrolidone, 1-3-dimethyl-2-imidazolidinone, imidazole, N-methylcaprolactam, dimethyl sulfoxide, diethyl sulfoxide, dimethyl sulfone, diethyl sulfone, hexamethylsulfoamide, cresol, phenol, xylenol, diethylene glycol dimethyl ether (diglyme), triethylene glycol ldimethyl ether (triglyme), tetraglyme, dioxane, tetrahydrofuran and γ-buthyllactone. At least two of them may be used in a mixture.

Next, the other reactive compounds and the other polymerizable compounds used for copolymerizing with the compound (1) shall be explained. The preferred examples of the other reactive compounds are glycols, dicarboxylic acids, diamines and tetracarboxylic dianhydrides, but they shall not be restricted thereto. The preferred examples of the other polymerizable compounds are vinyl base monomers, fumaric acid diesters and maleimide derivatives, but they shall not be restricted thereto.

The glycols may be belong to any one of groups of aliphatic type, alicyclic type and aromatic type, and they may contain a siloxane group and may be optically active. The examples of the aliphatic glycol are aliphatic diols (ethylene glycol, trimethylene glycol, 1,4-butanediol, 1,5-pentanediol, 1,6-hexanediol, diethylene glycol, propylene glycol, neopentyl glycol and the like) and polyether compounds (polyethylene glycol, polypropylene glycol, polybutylene glycol and the like).

The examples of the alicyclic glycol are 1,3-cyclohexanedimethanol, 1,4-cyclohexanedimethanol, 1,2-decahydronaphthalenedimethanol, 1,3-decahydronaphthalenedimethanol, 1,4-decahydronaphthalenedimethanol, 1,5-decahydronaphthalenedimethanol, 1,6-decahydronaphthalenedimethanol, 2,7-decahydronaphthalenedimethanol, tetralindimethanol, norbornanedimethanol, tricyclodecanedimethanol and pentacyclododecanedimethanol.

The examples of the aromatic glycol are alkylene oxide adducts of bisphenols and alkylene oxide adducts o aromatic dihydroxy compounds. The examples of the alkylene oxide adduct of bisphenol are 4,4'-(1-methylethylidene)bisphenol, methylenebisphenol (bisphenol F), 4,4'-cyclohexylidenebisphenol (bisphenol Z) and 4,4'-xulfonylbisphenol (bisphenol S). The examples of the alkylene oxide adducts of aromatic dihydroxy compounds are hydroquinone, resorcin, 4,4'-dihydroxybiphenyl, 4,4'-dihydroxydiphenyl ether and dihydroxydiphenylbenzophenone.

The glycols described above include ones in which isomers are present, and they may be mixtures containing them. Two or more glycols may be used in combination. When two or more glycols are used, two or more glycols may be selected from the same kind of the glycols described above, or at least one glycol may be selected from each of the different kind of the glycols. The glycols used in the present invention shall not be restricted to the foregoing compounds given as the examples.

The dicarboxylic acids or the derivatives thereof may be belong to any one of groups of aliphatic type, alicyclic type, aromatic type and heterocyclic type, and they may contain a siloxane group and may be optically active. The examples of the aliphatic dicarboxylic acid are malonic acid, oxalic acid, dimethylmalonic acid, succinic acid, fumaric acid, glutaric acid, adipic acid, muconic acid, 2-methyladipic acid, trimethyladipic acid, pimelic acid, 2,2-dimethylglutaric acid, 3,3-diethylsuccinic acid, azelaic acid, sebacic acid and suberic acid.

The examples of the alicyclic dicarboxylic acid are 1,1-cyclopropanedicarboxylic acid, 1,2-cyclopropanedicarboxylic acid, 1,1-cyclobutanedicarboxylic acid, 1,2-cyclobutanedicarboxylic acid, 1,3-cyclobutanedicarboxylic acid, 3,4-diphenyl-1,2-cyclobutanedicarboxylic acid, 2,4-diphenyl-1,3-cyclobutanedicarboxylic acid, 1-cyclobutene-1,2-dicarboxylic acid, 1-cyclobutene-3,4-dicarboxylic acid, 1,1-cyclopentanedicarboxylic acid, 1,2-cyclopentanedicarboxylic acid, 1,3-cyclopentanedicarboxylic acid, 1,1-cyclohexanedicarboxylic acid, 1,2-cyclohexanedicarboxylic acid, 1,3-cyclohexanedicarboxylic acid, 1,4-cyclohexanedicarboxylic acid, 1,4-(2-norbornene)dicarboxylic acid, norbornene-2,3-dicarboxylic acid, bicyclo[2.2.2]octane-1,4-dicarboxylic acid, bicyclo[2.2.2]octane-2,3-dicarboxylic acid, 2,5-dioxo-1,4-bicyclo[2.2.2]octanedicarboxylic acid, 1,3-adamantanedicarboxylic acid, 4,8-dioxo-1,3-adamantanedicarboxylic acid, 2,6-spiro[3.3]heptanedicarboxylic acid, 1,3-adamantanediacetic acid and camphanic acid.

The examples of the aromatic dicarboxylic acid are o-phthalic acid, isophthalic acid, terephthalic acid, 5-methylisophthalic acid, 5-tert-butylisophthalic acid, 5-aminoisophthalic acid, 5-hydroxyisophthalica acid, 2,5-dimethylterephthalic acid, tetramethylterephthalic acid, 1,4-naphthalene-dicarboxylic acid, 2,5-naphthalenedicarboxylic acid, 2,6-naphthalenedicarboxylic acid, 2,7-naphthalene-dicarboxylic acid, 1,4-anthracenedicarboxylic acid, 1,4-anthraquinonedicarboxylic acid, 2,5-biphenyl-dicarboxylic acid, 4,4'-biphenyldicarboxylic acid, 1,5-biphenylenedicarboxylic acid, 4,4"-terphenyldicarboxylic acid, 4,4'-diphenylmethane-dicarboxylic acid; 4,4'-diphenylethanedicarboxylic acid, 4,4-diphenylpropanedicarboxylic acid, 4,4'-diphenylhexafluoropropanedicarboxylic acid, 4,4'-diphenyletherdicarboxylic acid, 4,4'-bibenzyl-dicarboxylic acid, 4,4'-stilbenedicarboxylic acid, 4,4'-trandicarboxylic acid, 4,4'-carbonyldibenzoic acid, 4,4'-sulfonyldibenzoic acid, 4,4'-dithiodibenzoic acid, p-phenylenediacetic acid, 3,3'-p-phenylenedipropionic acid, 4-carboxycinnamic acid, p-phenylenediacrylic acid, 3,3'-(4,4'-(methylenedi-p-phenylene))dipropionic acid, 4,4'-(4,4'-(oxy-di-p-phenylene)) dipropionic acid, 4,4'-(4,4'-(oxy-di-p-phenylene))dibutyric acid, (isopropylidenedi-p-phenylenedioxy)dibutyric acid and bis(p-carboxyphenyl)dimethyl silane.

The examples of the dicarboxylic acid containing heterocycles are 1,5-(9-oxofluorene)dicarboxylic acid, 3,4-furancarboxylic acid, 4,5-thiazoledicarboxylic acid, 2-phenyl-4,5-thiazoledicarboxylic acid, 1,2,5-thiazole-3,4-dicarboxylic acid, 1,2,5-oxadiazole-3,4-dicarboxylic acid, 2,3-pyridinedicarboxylic acid, 2,4-pyridine-dicarboxylic acid, 2,5-pyridinedicarboxylic acid, 2,6-pyridinedicarboxylic acid, 3,4-pyridinedicarboxylic acid and 3,5-pyridinedicarboxylic acid.

The dicarboxylic acids described above: may be monoesters, diesters, acid monohalides, acid dihalides or anhydrides. One of two carboxyl groups may be esterified, and the other may be acid halide. These compounds include ones in which isomers are present, and they may be mixtures containing the isomers. Two or more dicarboxylic acids may be used in combination. When two or more dicarboxylic acids are used, two or more dicarboxylic acids may be selected from the same kind of the dicarboxylic acids described above, or at least one dicarboxylic acid may be selected from each of the different kind of the dicarboxylic acids. The dicarboxylic acids used in the present invention shall not be restricted to the foregoing compounds given as the examples.

The diamines may be belong to any one of groups of aliphatic type, alicyclic type and aromatic type, and they may contain a siloxane group and may be optically active. The examples of the aliphatic diamine are ethylenediamine, trimethylenediamine, tetramethylenediamine, pentamethylenediamine and hexamethylenediamine. In these alkylenediamines, the diamines may have a structure in which optional —$CH_2$— may be replaced by —O—.

The examples of the alicyclic diamine are 1,4-diaminodicyclohexane, 1,3-bis(aminomethyl)cyclohexane, 1,4-bis(aminomethyl)cyclohexane, 4,4'-diaminodicyclohexylmethane, bis(2-methyl-4-aminocyclohexyl)methane, isophoronediamine, bis(aminomethyl)-bicyclo[2.2.1]heptane; 2,6-bis(aminomethyl)-bicyclo[2.2.1]heptane, 2,3-diaminobicyclo[2.2.1]heptane, 2,5-diaminobicyclo[2.2.1]heptane, 2,6-diaminobicyclo[2.2.1]heptane, 2,7-diaminobicyclo[2.2.1]heptane, 2,3-diamino-7-azabicyclo[2.2.1]heptane, 2,5-diamino-7-azabicyclo[2.2.1]heptane, 2,6-diamino-7-azabicyclo-[2.2.1]heptane, 2,3-diamino-7-thiabicyclo-[2.2.1]heptane, 2,5-diamino-7-thiabicyclo-[2.2.1]heptane, 2,6-diamino-7-thiabicyclo-[2.2.1]heptane, 2,3-diaminobicyclo[2.2.2]octane, 2,5-diaminobicyclo[2.2.2]octane, 2,6-diaminobicyclo[2.2.2]octane, 2,5-diaminobicyclo[2.2.2]octane-7-ene, 2,5-diamino-7-azabicyclo[2.2.2]octane, 2,5-diamino-7-oxabicyclo[2.2.2]octane, 2,5-diamino-7-thiabicyclo-[2.2.2]octane, 2,6-diaminobicyclo[3.2.1]octane, 2,6-diaminoazabicyclo[3.2.1]octane, diaminooxabicyclo[3.2.1]octane, 2,6-diaminothiabicyclo[3.2.1]octane, 2,6-diaminobicyclo[3.2.2]nonane, 2,6-diaminobicyclo[3.2.2]nonane-8-ene, 2,6-diamino-8-azabicyclo[3.2.2]nonane, 2,6-diamino-8-oxabicyclo[3.2.2]nonane and 2,6-diamino-8-thiabicyclo[3.2.2]nonane.

The examples of: the aromatic diamine are 2,2-bis(4-aminophenyl)propane, 2,6-diaminopyridine, aminophenyl)diethylsilane, bis-(4-aminophenyl)-diphenylsilane, bis-(4-aminophenyl)ethylphosphine oxide, bis-(4-aminophenyl)-N-butylamine, N,N-bis-(4-aminophenyl)-N-methylamine, N-(3-aminophenyl)-4-aminobenzamide, 3,3'-diaminodiphenylmethane, 3,3'-diaminodiphenyl ether, 3,3'-diaminodiphenyl sulfone, 2,2-bis(3-aminophenyl)propane, 1,3-bis(3-aminophenyl)propane, 3,3'-diaminodiphenyl sulfide, 2,3,5,6-tetramethyl-p-phenylenediamine, 2,5-dimethyl-p-phenylenediamine; p-xylenediamine, m-xylenediamine, p-xylenediamine, m-xylylenediamine, 2,4-diaminotoluene, 2,6-diaminotoluene, 1,2-bis(3-diaminophenyl)ethane, 1,1-bis(3-diaminophenyl)ethane, 4,4'-diaminodiphenylhexafluoropropane, 2,2-bis(4-aminophenyl)hexafluoropropane, 4,4'-diaminobenzophenone, 4,4'-diaminodiphenyl sulfide, 4,4'-diaminodiphenyl sulfone, 4,4'-diaminodiphenyl ether, 3,4'-diaminodiphenyl ether, 1,5-diaminonaphthalene, 2,6-diaminonaphthalene, bis(4-(4-aminophenoxy)phenyl)methane, 1,1-bis(4-(4-aminophenoxy)phenyl)ethane, 1,2-bis(4-(4-aminophenoxy)phenyl)ethane, 1,1-bis[4-(4-aminophenoxy)phenyl]propane, 2,2-bis[4-(4-aminophenoxy)phenyl]propane, 2,2-bis(4-(4-aminophenoxy)phenyl]butane, 4,4'-bis(4-aminophenoxy)-diphenyl ketone, bis(4-(4-aminophenoxy)phenyl)sulfone, bis(4-(4-aminophenoxy)phenyl)sulfide, 1,3-bis(4-(4-aminophenoxy)phenyl)benzene, 1,4-bis(4-(4-aminophenoxy)phenyl)benzene, 4,4'-bis(4-(4-aminophenoxy)phenyl)biphenyl, 1,2-bis(4-(4-aminophenoxy)phenyl)cyclohexane, 1,3-bis(4-(4-aminophenoxy)phenyl)cyclohexane, 1,4-bis(4-(4-aminophenoxy)phenyl)cyclohexane, bis(4-(4-aminophenoxy)phenyl)hexafluoropropane, 2,2-bis(4-(2-aminophenoxy)phenyl)hexafluoropropane, 2,2-bis(4-(3-aminophenoxy)phenyl)hexafluoropropane, 2,2-bis(4-(3-carbamoyl-4-aminophenoxy)phenyl)hexafluoropropane, 2,2-bis-(3-sulfamoyl-4-aminophenyl)hexafluoropropane, 2,2-bis-(3-carboxy-4-aminophenyl)hexafluoropropane, 2,2-bis(4-(3-sulfamoyl-4-aminophenoxy)phenyl)-hexafluoropropane, 2,2-bis(4-(3-carboxy-4-aminophenoxy)phenyl)hexafluoropropane, 1,3-bis(2,2-[4(4-aminophenoxy)phenyl]hexafluoroisopropyl)benzene, 2,4-bis(β-amino-t-butyl)toluene, bis(p-β-methyl-γ-aminopentyl)benzene, bis-p-(1,1-dimethyl-5-aminopentyl)benzene, bis(p-β-amino-t-butylphenyl)ether, bis(4-aminobenzoloxy)methane, bis(4-aminobenzoloxy)ethane, bis(4-aminobenzoloxy)propane, bis(4-aminobenzoloxy)cyclohexane, p-phenylenediamine, m-phenylenediamine, o-phenylenediamine, 4,4'-diaminobiphenyl, 4,4'-diaminodiphenylmethane, 4,4'-diaminodiphenylethane, 4,4'-diaminobiphenyl, 3,3'-methylbenzidine, 1,3-bis(4-aminophenyl)propane, 2,2-bis(4-aminophenyl)propane, bis(4-amino-3-methylphenyl)methane, bis(4-amino-2-methylphenyl)-methane, 1,2-bis(4-amino-3-methylphenyl)ethane, 1,3-bis(4-amino-3-methylphenyl)propane, 1,2-bis(4-amino-2-methylphenyl)ethane, 1,3-bis(4-amino-2-methylphenyl)propane, 1,4-bis(4-aminophenyl)benzene, 1,4-bis((4-aminophenyl)methyl)benzene, 1,4-bis((3-aminophenyl)methyl)benzene, 1,4-bis((4-aminophenyl)ethyl)benzene, 1,4-bis((3-aminophenyl)ethyl)benzene, bis((4-amino-3-methyl-phenyl)methyl)benzene, 1,4-bis((4-amino-3-methyl-phenyl)ethyl)benzene, 4,4'-(4-aminophenyl)biphenyl, bis-((4-(4-aminophenylmethyl)-phenyl)methane, bis-((4-(4-aminophenylmethyl)-phenyl)ethane, bis-((4-(3-aminophenylmethyl)-phenyl)methane, bis((4-(3-aminophenylmethyl)-phenyl)ethane, 2,2-bis((4-(aminophenylmethyl)-phenyl)propane and 2,2-bis-((4-(3-aminophenylmethyl)phenyl)propane.

The diamines described above include ones in which isomers are present, and they may be mixtures containing the isomers. Two or more diamines may be used in combination. When two or more diamines are used, two or more diamines may be selected from the same kind of the diamines described above, or at least one diamine may be selected from each of the different kind of the diamines. The diamines used in the present invention shall not be restricted to the foregoing compounds given as the examples.

The tetracarboxylic dianhydrides may be belong to any one of groups of aliphatic type, alicyclic type and aromatic type, and they may contain a siloxane group and may be optically active. Among them, the examples of the aliphatic tetracarboxylic dianhydride are ethanetetracarboxylic dianhydride and butanetetracarboxylic dianhydride. The examples of the alicyclic tetracarboxylic dianhydride are cyclobutanetetracarboxylic dianhydride, cyclopentanetetracarboxylic dianhydride, bicycloheptanetetracarboxylic dianhydride, bicyclooctanetetracarboxylic dianhydride, bicyclo[2.2.2]-octo-7-ene-2,3,5,6-tetracarboxylic dianhydride, cyclohexane-1,2,5,6-tetracarboxylic dianhydride, 3,4-dicarboxy-1,2,3,4-tetrahydronaphthalene-1-succinic dianhydride, 3,3'-bicyclohexyl-1,1',2,2'-tetracarboxylic dianhydride, 2,3,5-tricarboxycyclopentylacetic dianhydride, 5-(2,5-dioxotetrahydrofural)-3-methyl-3-cyclohexene-1,2-dicarboxylic dianhydride, 1,3,3a,4,5,9b-hexahydro-5-tetrahydro-2,5-dioxo-3-franyl)-naphtho[1,2-c]-furan-1,3-dione, 3,5,6-tricarboxynorbornane-2-acetic dianhydride, 2,3,4,5-tetrahydrofurantetracarboxylic dianhydride and tetracyclo[6.2.1$^{1,3}$.0$^{2,7}$]dodecane-4,5,9,10-tetracarboxylic dianhydride. Further, an acid anhydride having a structure represented by the following formula can be given. In these compounds, optional hydrogen may be replaced by lower alkyl such as methyl and ethyl:

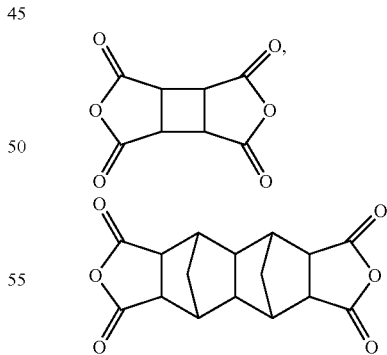

The examples of the aromatic tetracarboxylic dianhydride are pyromellitic dianhydride, 3,3',4,4'-benzophenonetetracarboxylic dianhydride, naphthalenic dianhydride (2,3,6,7-naphthalenic anhydride and the like), 3,3'-4,4'-diphenylmethanetetracarboxylic dianhydride, 3,3'-4,4'-diphenylethanetetracarboxylic dianhydride, 3,3'-4,4'-diphenylpropane-tetracarboxylic dianhydride, 3,3'-4,4'-diphenylsulfonetetracaroxylic dianhydride, 3,3',4,4'- diphenylethertetracarboxylic dianhydride, 3,3',4,4'-dimethyldiphenylsilanetetracarboxylic dianhydride, 4,4'-bis(3,4-dicarboxyphenoxy)diphenylsulfide dianhydride, 4,4'-bis(3,4-dicarboxyphenoxy)-diphenylsulfonic dianhydride, 4,4'-bis(3,4-dicarboxyphenylmethyl)diphenylmethane dianhydride, dicarboxyphenylmethyl)diphenylethane dianhydride, 4,4'-bis(3,4-dicarboxyphenylmethyl)-diphenylpropane dianhydride, 4,4'-bis(3,4-dicarboxyphenoxy)diphenylmethane dianhydride, 4,4'-bis(3,4-dicarboxyphenoxy)diphenylethane dianhydride, 4,4'-bis(3,4-dicarboxyphenoxy)diphenylpropane dianhydride, 3,3',4,4'-perfluoropropylidene-diphthalic dianhydride, 3,3',4,4'-biphenyltetracarboxylic dianhydride, bis(phthalic)-phenylsulfine oxide dianhydride, p-phenylene-bis(triphenylphthalic) dianhydride, m-phenylene-bis(triphenylphthalic) dianhydride, bis(triphenyl-phthalic)-4,4'-diphenyl ether dianhydride and bis(triphenylphthalic)-4,4'-diphenylmethane dianhydride.

The various tetracarboxylic dianhydrides described above include ones in which isomers are present, and they may be mixtures containing the isomers. Two or more tetracarboxylic dianhydrides may be used in combination. When two or more tetracarboxylic dianhydrides are used, two or more tetracarboxylic dianhydrides may be selected from the same kind of the tetracarboxylic dianhydrides described above, or at least one tetracarboxylic dianhydride may be selected from each of the different kind of the tetracarboxylic dianhydrides. The tetracarboxylic dianhydrides used in the present invention shall not be restricted to the foregoing compounds given as the examples.

The tricarboxylic acids may be belong to any one of groups of aliphatic type, alicyclic type and aromatic type, and they may contain a siloxane group and may be optically active. The examples of the tricarboxylic acid are trimellitic acid, trimesic acid, hemimellitic acid, propanetricarboxylic acid and cyclohexane-tricarboxylic acid. These tricarboxylic acids may be monoesters, diesters, triesters, acid monohalides, acid dihalides, acid trihalides or compounds in which two carboxyl groups are reduced to acid anhydrides. They may be monoester acid dihalides, diester acid monohalides or compounds having a structure in which two carboxyl groups are reduced to acid anhydrides and remaining carboxyl group is esterified or is acid halide. These compounds include ones in which isomers are present, and they may be mixtures containing the isomers. Two or more tricarboxylic acids may be used in combination. When two or more tricarboxylic acids are used, two or more tricarboxylic acids may be selected from the same kind of the tricarboxylic acids described above, or at least one tricarboxylic acid may be selected from each of the different kind of the tricarboxylic acids. The tricarboxylic acid-derivatives used in the present invention shall not be restricted to the foregoing compounds given as the examples.

The dicarboxylic acids, tricarboxylic acids and tetracarboxylic acids described above may be used in combination of two or three kinds thereof. That is, the examples of the combination are the combination consisting of at least one of each of dicarboxylic acids and tricarboxylic acids, the combination consisting of at least one of each of dicarboxylic acids and tetracarboxylic acids, the combination consisting of at least one of each of tricarboxylic acids and tetracarboxylic acids and the combination consisting of at least one of each of dicarboxylic acids, tricarboxylic acids and tetracarboxylic acids.

Capable of being given as the vinyl base monomers are olefins, halogenated vinyls, vinyl esters, aromatic vinyl base monomers, styrene derivatives, vinyl ethers, alkyl vinyl ketones, dienes, (meth)acrylates, itaconates, α,β-vinylnaphthalene, N-vinylacetamide and the like. They may contain a siloxane group and may be optically active.

The examples of the olefin are ethylene, propylene and isobutene. The examples of the halogenated vinyl are vinyl chloride and vinyl fluoride. The examples of the vinyl ester are vinyl acetate, vinyl pivalate, vinyl 2,2-dimethylbutanoate, vinyl 2,2-dimethylpentanoate, vinyl 2-methyl-2-butanoate, vinyl propionate, vinyl stearate and vinyl 2-ethyl-2-methylbutanoate. The examples of the aromatic vinyl base monomer are vinyl p-t-butylbenzoate and vinyl N,N-dimethylaminobenzoate. The examples of the styrene derivative are styrene, o-chlorostyrene, chlorostyrene, p-chlorostyrene; o-chloromethylstyrene, m-chloromethylstyrene, p-chloromethylstyrene and α-methylstyrene.

The examples of the vinyl ether are ethyl vinyl ether, hydroxybutyl vinyl ether, t-amyl vinyl ether and cyclohexanedimethanol/methyl vinyl ether. The examples of the alkyl vinyl ketone are methyl vinyl ketone and isobutyl vinyl ketone. The examples of the diene are butadiene and isoprene. The examples of the (meth)acrylate are methyl(meth)acrylate, ethyl(meth)acrylate, butyl(meth)acrylate, 2-ethylhexyl (meth)acrylate and phenyl(meth)acrylate. The examples of the itaconate are dimethyl itaconate, diethyl itaconate, dibutyl itaconate and diisopropyl itaconate. (Meth)acrylate is a general term for acrylate and methacrylate.

The various vinyl base monomers described above include ones in which isomers are present; and they may be mixtures containing the isomers. Two or more kinds of the compounds may be used in combination. The vinyl base monomers used in the present invention shall not be restricted to the foregoing compounds given as the examples.

The fumaric acid diesters may have a siloxane group and may be optically active. The examples of the fumaric acid diester are diethyl fumarate, diisopropyl fumarate, dibutyl fumarate, dicyclohexyl fumarate, di(1-phenyl-2-propyl) fumarate, di-sec-butyl fumarate, di-t-butyl fumarate, di-2-ethylhexyl fumarate, (isopropyl) (ethyl) fumarate, (isopropyl) (propyl) fumarate, (isopropyl) (butyl) fumarate, (isopropyl) (sec-butyl) fumarate, (isopropyl) (t-butyl) fumarate, (isopropyl) (isoamyl) fumarate, (isopropyl) (sec-amyl) fumarate, (isopropyl) (sec-hexyl) fumarate, (isopropyl) (4-methyl-2-pentyl) fumarate, (isopropyl) (2-ethylhexyl) fumarate, (isopropyl) (octyl) fumarate, (isopropyl) (cyclohexyl) fumarate, (isopropyl) (nonyl) fumarate, (t-butyl) (sec-butyl) fumarate, (t-butyl) (cyclohexyl) fumarate, (t-butyl) (4-methyl-2-pentyl) fumarate, (t-butyl) (2-ethylhexyl) fumarate, (isopropyl) (cyclohexyl) fumarate, (isopropyl) (cyclopentyl) fumarate, (isopropyl) (2-phenyl-1-ethyl) fumarate, (isopropyl) (3-phenyl-propyl) fumarate, (isopropyl) (1-phenyl-2-propyl) fumarate, (isopropyl) (1-phenyl)-propyl) fumarate, (isopropyl) (trimethylsilylpropyl) fumarate, (t-butyl) (trimethylsilylpropyl) fumarate, (cyclohexyl) (trimethylsilylpropyl) fumarate, (isopropyl) (3-tris(trimethylsiloxy)silylpropyl) fumarate, (isopropyl) (3-(pentamethyldisiloxanyl)propyl) fumarate, dimethylaminoethyl) (isopropyl) fumarate, (t-butyl) (1-butoxy-2-propyl) fumarate, (2-cyanoethyl) (isopropyl) fumarate, (2-hydroxyethyl) (isopropyl) fumarate, (glycidyl) (isopropyl) fumarate, (isopropyl) (diethylphosphomethyl) fumarate, (2-methylthioethyl) (isopropyl) fumarate, (isopropyl) (2-(hydroxyethylthioethyl)isopropyl) fumarate, (perfluorooctylethyl) (isopropyl) fumarate, (trifluoromethyl) (isopropyl) fumarate, (pentafluoroethyl) (isopropyl) fumarate and (hexaflubroisopropyl) (isopropyl) fumarate.

The fumaric acid diesters described above include ones in which isomers are present, and they may be mixtures containing the isomers. Two or more kinds of the compounds may be used in combination. The fumaric acid diesters used in the present invention shall not be restricted to the foregoing compounds given as the examples.

Multifunctional acrylates can be added in order to enhance more a coating film-forming ability of the polymer (3). The multifunctional acrylates may have a siloxane group and may be optically active. The preferred examples of the multifunctional acrylate are 1,4-butanediol diacrylate, 1,6-hexanediol diacrylate, 1,9-nonanediol diacrylate, neopentyl glycol diacrylate, triethylene glycol diacrylate, dipropylene glycol diacrylate, tripropylene glycol diacrylate, tetraethylene glycol diacrylate, trimethylolpropane triacrylate, trimethylol EO-added triacrylate, pentaerythritol triacrylate, trisacryloyloxyethyl phosphate, bisphenol A EO-added diacrylate, bisphenol A glycidyl ether diacrylate and polyethylene glycol diacrylate. Bisphenol A glycidyl ether diacrylate is commercially available as Biscoat 700 from Osaka Organic Chemical Co., Ltd.

The multifunctional acrylates described above include ones in which isomers are present, and they may be mixtures containing the isomers. Two or more kinds of the compounds may be used in combination. The multifunctional acrylates used in the present invention shall not be restricted to the foregoing compounds given as the examples.

The maleimide derivatives may have a siloxane group and may be optically active. The examples of the maleimide derivative are N-methylmaleimide, N-ethylmaleimide, N-propylmaleimide, N-butylmaleimide, N-pentylmaleimide, N-hexylmaleimide, N-heptylmaleimide, N-octylmaleimide, N-nonylmaleimide, N-decylmaleimide, N-undecylmaleimide, N-dodecylmaleimide, N-octadecylmaleimide, N-isopropylmaleimide, N-(sec-butyl)maleimide, N-It-butyl)maleimide, N-(1-methylbutyl)maleimide, N-(2-methylbutyl)maleimide, N-(3-methylbutyl)maleimide, N-(sec-hexyl)maleimide, N-(4-methyl-2-pentyl)maleimide, N-(sec-heptyl) maleimide, N-(sec-octyl)maleimide, N-cyclopropylmaleimide, N-cyclobutylmaleimide, N-cyclopentylmaleimide, N-cyclohexylmaleimide, N-phenylmaleimide, N-(2-methylphenyl)maleimide, N-(2-ethylphenyl) maleimide, N-(2-isopropylphenyl)maleimide, N-(2,6-dimethylphenyl)Maleimide, N-(2,6-diethylphenyl) maleimide, N-(2,6-diisopropylphenyl)-maleimide, N-(2,4,6-trimethylphenyl)maleimide, N-(2-chlorophenyl)maleimide, N-(3-methylphenyl)maleimide, N-(3-ethylphenyl)maleimide, N-(3-trifluoromethyl-phenyl)maleimide, N-(3,5-dimethylphenyl)maleimide, N-benzylmaleimide, N-(4-methylphenyl)maleimide, N-(4-ethylphenyl)maleimide, N-(4-propylphenyl)maleimide, N-(4-isopropylphenyl)maleimide, N-(4-butylphenyl)-maleimide, N-(4-pentylphenyl)maleimide, N-trifluoromethylmaleimide, N-(1-(trifluoromethyl)ethylmaleimide, N-(3,3,3-trifluoropropyl)maleimide, N-hexafluoroisopropylmaleimide, N-perfluoroisopropylmaleimide, N-perfluorobutylethylmaleimide, N-perfluorooctylethylmaleimide, N-(2-chloroethyl)-maleimide, N-(1-butoxy-2-propyl)maleimide, N-(methoxyethyl)maleimide, N-(trimethylsilyl)maleimide, N-(t-butyldimethylsilyl)maleimide, N-(dimethylmethoxysilyl)maleimide, N-(2-cyanoethyl)maleimide, N-(2-hydroxyethyl)maleimide, N-(3-hydroxypropyl)maleimide, N-(4-hydroxybutyl)-maleimide, N-(5-hydroxypentyl)maleimide, N-(6-hydroxyhexyl)maleimide, N-(7-hydroxyheptyl)maleimide, N-(8-hydroxyoctyl) maleimide, N-(9-hydroxynonyl)-maleimide and N-(10-hydroxydecyl)maleimide.

The maleimide derivatives described above include ones in which isomers are present, and they may be mixtures containing the isomers. Two or more kinds of the compounds may be used in combination. The maleimide derivatives used in the present invention shall not be restricted to the foregoing compounds given as the examples.

When two or more other polymerizable compounds are used for the addition-polymerizable composition, two or more compounds may be selected from the same kind of the addition-polymerizable compounds described above, or at least one compound may be selected from each of the different kind of the addition-polymerizable compounds.

The polymer (3) can be obtained by polymerizing the compound (1), the addition-polymerizable composition or the condensation-polymerizable composition described above. The preferred example of the polymer obtained using the compound (1) is a polymer obtained using the compound (1) having —$OM^1$, —CHO, —$COOR^3$, —$NHR^4$, —$COX^1$, —$OCOX^1$, —N=C=O, —$CR^5$=$CH_2$, oxiranyl, oxetanyl, 3,4-epoxycyclohexyl or any one of groups shown below:

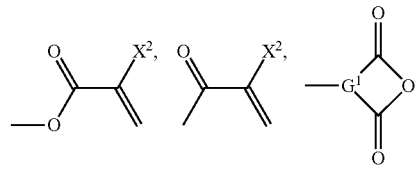

More preferred example of the polymer obtained using the compound (1) is a polymer obtained using the compound (1) having —$OM^1$, —$COOR^3$, —$NHR^4$, —$COX^1$, —N=C=O, —$CR^5$=$CH_2$, oxiranyl, oxetanyl or any one of groups shown below:

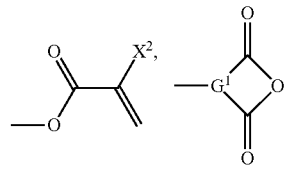

The representative examples of the polymer obtained using the compound (1) are polyimides, polyamic acids, polyesters, epoxy resins, polyacrylates and polymethacrylates. The polyamic acid is obtained by the reaction of the compound (1), which is diamine, with tetracarboxylic dianhydride. This tetracarboxylic dianhydride may be the compound (1), a tetracarboxylic dianhydride other than the compound (1), or a mixture of these tetracarboxylic dianhydrides. Diamines other than the compound (1) may be added to the compound (1) which is diamine. Another example of the polyamic acid is obtained by the reaction of the compound (1), which is tetracarboxylic dianhydride, with diamine. This diamine may be the compound (1), a diamine other than the compound (1), or a mixture of these diamines. Tetracarboxylic dianhydrides other than the compound (1) may be added to the compound (1) which is tetracarboxylic dianhydride. The polyimides are obtained by subjecting the above polyamic acids to dehydration ring-closure.

The polyester is obtained by the reaction of the compound (1), which is diol, with a carboxylic acid derivative having at least two carboxyls, acid halide groups, acid anhydride groups or ester groups. The carboxylic acid derivative may be the compound (1), a carboxylic acid derivative other than the compound (1), or a mixture of these carboxylic acid derivatives. Diols other than the compound (1) may be added to the compound (1) which is diol. Another example of the polyester is obtained by the reaction of the compound (1), which is the carboxylic acid derivative having at least two carboxyls, acid halide groups, acid anhydride groups or ester groups, with diol. This diol may be the compound (1), a diol other than the compound (1), or a mixture of these diols. Carboxylic acid derivatives other than the compound (1) may be added to the compound (1) which is the carboxylic acid derivative.

The epoxy resin is obtained by the addition reaction of the compound (1), which is bisepoxide, with an active hydrogen compound having at least two of any one of amino group, carboxyl group, phenolic hydroxyl group and thiol group, the copolycondensation reaction of the compound (1), which is bisepoxide, with acid anhydride, or the self polymerization of the compound (1), which is bisepoxide, by a basic or acidic catalyst. The active hydrogen compound may be the compound (1), an active hydrogen compound other than the compound (1), or a mixture of these active hydrogen compounds. Also, the acid anhydride may be the compound (1), which is tetracarboxylic dianhydride, a acid anhydride other than the compound (1) or a mixture of these compounds. The basic or acidic catalyst is an anionic polymerization catalyst such as alkoxides of sodium or potassium, hydroxides, amides, hydrides and Na-naphthalene, a cationic polymerization catalyst including Lewis acids such as $SnCl_4$, $BF_3$ and $AlCl_3$, and protonic acids such as HCl, HBr and $H_2SO_4$, and a coordinate polymerization catalyst such as alkoxides of Ca and Ba, oxides, carbonates, amides, alkoxides of Al, Mg and Zn and $Zn(C_2H_5)_n$—$H_2O$ base and $Al(C_2H_5)_3$—$H_2O$ base catalysts. Also, bisepoxides other than the compound (1) may be added to the compound (1) which is bisepoxide. Another example of the epoxy resin is an epoxy resin obtained by the reaction of the compound (1) having at least two of any one of amino group, carboxyl group, phenolic hydroxyl group and thiol group with bisepoxide, or the reaction of the compound (1), which is a tetracarboxylic dianhydride, with bisepoxide. The bisepoxide may be the compound (1), a bisepoxide other than the compound (1), or a mixture of these bisepoxides. Active hydrogen compounds other than the compound (1) may be added to the compound (1) which is an active hydrogen compound. Acid anhydrides compounds other than the compound (1) may be added to the compound (1) which is a tetracarboxylic dianhydride.

The examples of the polyacrylate are a homopolymer of the compound (1) having acryloyloxy, a copolymer obtained from at least two of the above compounds (1), a copolymer of at least one of the above compounds (1) and at least one of the compounds (1) having methacryloyloxy, a copolymer of at least one of the above compounds (1) and at least one of compounds having acryloyloxy or methacryloyloxy other than the compound (1), and a copolymer of at least one of the above compounds (1), at least one of the compounds (1) having methacryloyloxy and at least one of compounds having acryloyloxy or methacryloyloxy other than the compound (1).

The examples of the polymethacrylate are a homopolymer of the compound (1) having methacryloyloxy, a copolymer obtained from at least two of the above compounds (1), a copolymer of at least one of the above compounds (1) and at least one of the compounds (1) having acryloyloxy, a copolymer of at least one of the above compounds (1) and at least one of compounds having acryloyloxy or methacryloyloxy other than the compound (1), and a copolymer of at least one of the above compounds (1), at least one of the compounds (1) having acryloyloxy and at least one of compounds having acryloyloxy or methacryloyloxy other than the compound (1).

The compound (1) and the polymer (3) are characterized by that they are physically and chemically stable very much on conditions usually used and that they have a good compatibility with other polymers and compounds. Suited selection of rings, bonding groups or side chains constituting the compound (1) makes it possible to suitably select the structure of the polymer (3), and therefore capable of being produced is the polymer having optimum transparency, refractive index, mechanical strength, coating property, solubility, crystallinity, shrink property, water permeability, water absorbency, gas permeability, melting point, glass transition point, heat resistance, thermal expansion coefficient, water repellency, electrical insulating property, compatibility and chemical resistance.

The compound (1), the polymer (3) or the composition containing them can be molded into a thin film, a multilayer membrane, a film, a fiber, a powder, a paste and other molded articles by a method which is usually used for producing conventional molded articles of high molecular-materials. In this case, capable of being blended, if necessary, are aliphatic polyols such as ethylene glycol and propylene glycol, aliphatic or aromatic carboxylic acid compounds, carbon dioxide gas-preventing agents such as phenol compounds, flexibility-providing agents such as polyalkylene glycols, antioxidants, plasticizers, lubricants, coupling agents such as silanes, surface treating agents for inorganic fillers, flame retardants, antistatic agents, colorants, leveling agents, ion trapping agents, slid-improving agents, various rubbers, impact-improving agents such as organic polymer beads, swing-providing agents, surfactants, surface tension-reducing agents, defoaming agents, precipitation preventives, light scattering agents, UV absorbers, heat stabilizers, antioxidants, mold releasing agents, fluorescent agents, conductive fillers, foaming agents and additives such as pigments.

For example, the polymer (3) of the present invention is dissolved homogeneously in a solvent, and the resulting solution is cast on a substrate and heated to volatilize the solvent, whereby a uniform film of 1 to 100 μm can be obtained. A polymer film, a glass plate, a silicon rubber plate and a metal plate can be given as the substrate used for molding a film by the above casting method. When a substrate having a prescribed thickness is obtained, the polymer is repeatedly cast and laminated so that the targeted film thickness is obtained, and then it is heated to volatilize the solvent, whereby the substrate having a prescribed thickness can be prepared. In this case, pressing can be carried out as well while heating and applying pressure.

Further, a multilayer substrate can be obtained by laminating a metal conductive layer of gold, copper or aluminum between the films and/or on the outermost layer. Also in this case, a metal conductive film is superposed thereon and heated in the same manner as described above to volatilize the solvent, whereby the substrate having a good adhesive property with the metal conductive film can be obtained. The metal conductive layer is obtained by forming a circuit by etching. Further, it can be formed as well by a vacuum deposition method and a screen printing method.

Capable of being given as the solvent which can be used in the casting method are aromatic hydrocarbon base solvents such as benzene and toluene, ketone base solvents such as methyl ethyl ketone, methyl isobutyl ketone and cyclohexanone, tetrahydrofuran, chloroform, N-methyl-2-pyrrolidone, N,N-dimethylformamide, N,N-dimethylacetamide, N,N-dimethylacetamide dimethylacetal, dimethylsulfoxide, 1,4-dioxane, ethyl acetate, 2-n-butoxyethanol, γ-butyrolactone, trifluoroacetic acid, ethyl trifluoroacetate and hexafluoro-2-propanol. Among the above solvents, two or more solvents may be used in combination. The solvents which can be used in the present invention shall not be restricted to the examples described above.

EXAMPLES

The present invention shall be explained below in more details with reference to examples, but the present invention shall not be restricted by these examples. The structures of the compounds were confirmed by a nuclear magnetic resonance (NMR) spectrum, a mass (MS) spectrum and an infrared absorption (IR) spectrum. The following apparatuses and methods were used for measuring the physical properties in the examples.

<Weight Average Molecular Weight (Mw) and Number Average Molecular Weight (Mn)>

Used were a Shimadzu LC-9A type gel permeation chromatograph (GPC) manufactured by Shimadzu Mfg. Co., Ltd. and a column Shodex GF-7M HQ (developing solvent was DMF or THF, and a standard substance was polystyrene having a known molecular weight) manufactured by Showa Denko Co., Ltd.

<Pencil Hardness>

The polymer thin film formed on a glass plate was measured for a pencil hardness by means of a pencil hardness meter YOSHIMITSU SEIKI C-221 according to JIS "JIS-K-5600-5-4 scratch hardness (pencil method)".

<Refractive Index>

The polymer thin film formed on a glass plate, on which chromium was deposited, was measured for a refractive index. It was measured at a measuring wavelength of 589.3 nm and 25° C. by a reflection system measuring method using a sulfur methylene iodide solution as an intermediate solution by means of an Abbe's refractometer ATAGO DR-M2.

<Light Transmittance>

The polymer thin film formed on a glass plate was measured for a light transmittance by means of a micro color analyzer TC-1800M (manufactured by Tokyo Denshoku Technical Center.

<Surface Free Energy>

The contact angles of purified water (specific resistance: 18 MΩ·cm) and ethylene glycol which were dropped on the polymer thin film were measured at 25° C. by means of a contact angle meter CA-A (manufactured by Kyowa Kaimen Kagaku Co., Ltd.) to calculate the surface free energy.

<Thermal Cracking-Starting Temperature, 5% Weight-Reducing Temperature and 10% Weight-Reducing Temperature>

The polymer thin film formed on a glass plate was peeled to prepare a sample. It was heated from 30° C. to 800° C. at 10° C./minute in aerial atmosphere by means of SEIKO SSC5000 TG/DTA 300 to measure a weight change, and the respective temperatures were determined from the inflection points obtained. Codes used in the examples have the following meanings:

Ph: phenyl
Me: methyl
TMS: trtimethylsilyl group
HMDS: hexamethyldisilazane
THF: tetrahydrofuran
NMP: N-methyl-2-pyrrolidone Example 1

Production of Compound (1-3-7)

Compound (1-3-7) was produced via the following route:

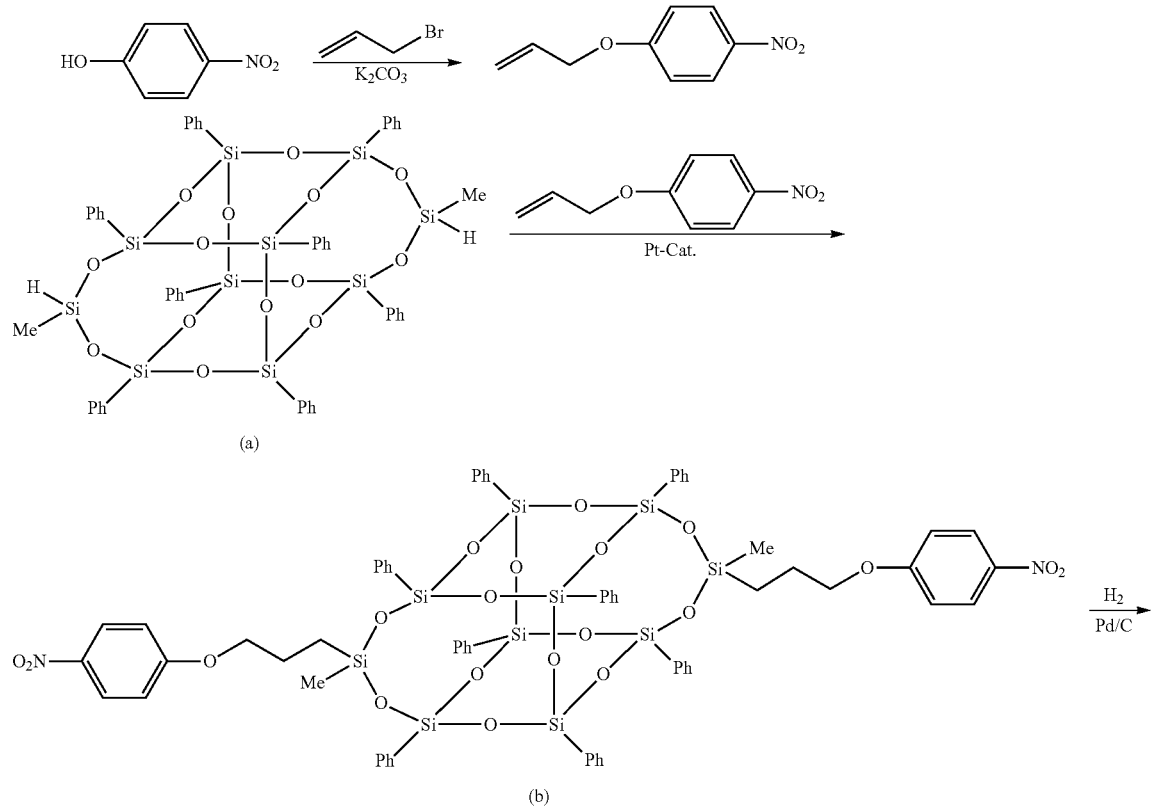

(a)

(b)

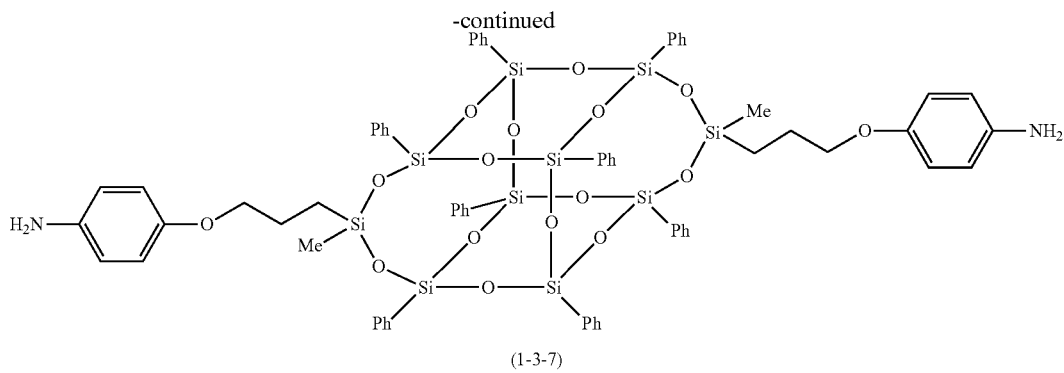

(1-3-7)

First Stage: Production of allyl p-nitrophenyl ether

Potassium carbonate (49.7 g, 0.36 mol) was added to an N,N-dimethylformamide (250 ml) solution of p-nitrophenol (25.0 g, 0.18 mol) under nitrogen atmosphere and suspended, and 3-bromopropene (21.7 g, 0.18 mol) was dropwise added thereto. After finishing dropwise adding, the solution was stirred at a room temperature for 5 hours, and then extracting practice with diethyl ether was carried out after adding water to the solution. The organic layer was washed with water and then dried on anhydrous magnesium sulfate. The solvent was distilled off under reduced pressure, and the residue thus obtained was refined by means of silica gel chromatography (eluent solvent: toluene). Toluene was distilled off under reduced pressure, and then the resulting residue was recrystallized from ethanol to obtain allyl p-nitrophenyl ether (25.7 g).

Second Stage: Production of Compound (b)

Toluene (500 ml) was added to a compound (a) (50.0 g, 43.3 mmol) under nitrogen atmosphere and suspended, and a platinum-divinylsiloxane complex (3 wt % toluene solution, 25 μl) was added thereto and heated to 90° C. Allyl p-nitrophenyl ether (16.3 g, 91 mmol) was dropwise added thereto in 5 minutes, and the solution was heated for 2 hours while refluxing. After standing to cool, toluene (100 ml) and water (300 ml) were added thereto, and extracting practice was carried out. The organic layer was washed with water and then dried on anhydrous magnesium sulfate. Toluene was distilled off under reduced pressure, and the residue thus obtained was refined by means of silica gel chromatography (eluent solvent: toluene). Toluene was distilled off under reduced pressure, and then the resulting residue was recrystallized from ethanol/ethyl acetate to obtain a compound (b) 18.7 g.

$^1$H-NMR (solvent: CDCl$_3$): δ (ppm); 0.34 (s, 6H), 0.85-0.88 (t, 4H), 1.92-1.95 (m, 4H), 3.85-3.88 (t, 4H), 6.60-6.63 (d, 4H), 7.15-7.52 (m, 40H), 7.94-7.97 (d, 4H).

$^{29}$Si-NMR (solvent: CDCl$_3$): δ (ppm); −17.8 (d, 2Si), −78.5 (s, 4Si), −79.4 (t, 4Si).

Third Stage: Production of Compound (1-3-7)

A mixture of the compound (b) (10.0 g, 6.61 mmol), Pd/C (1 g) and THF (100 ml) was stirred at a room temperature for 120 hours under hydrogen atmosphere. After filtering off Pd/C, THF was distilled off under reduced pressure. The resulting residue was refined by means of silica gel chromatography (eluent solvent: ethyl acetate). Ethyl acetate was distilled off under reduced pressure to obtain Compound (1-3-7) 6.3 g.

$^1$H-NMR (solvent: CDCl$_3$): δ (ppm); 0.31 (s, 6H), 0.83-0.87 (t, 4H), 1.82-1.87 (m, 4H), 3.71-3.74 (t, 4H), 6.51-6.57 (d, 8H), 7.14-7.95 (m, 40H).

$^{29}$Si-NMR (solvent: CDCl$_3$): δ (ppm); −17.5 (d, 2Si), −78.6 (s, 4Si), −79.6 (t, 4Si).

Example 2

Production of Compound (1-1-4)

Compound (1-1-4) was produced via the following route:

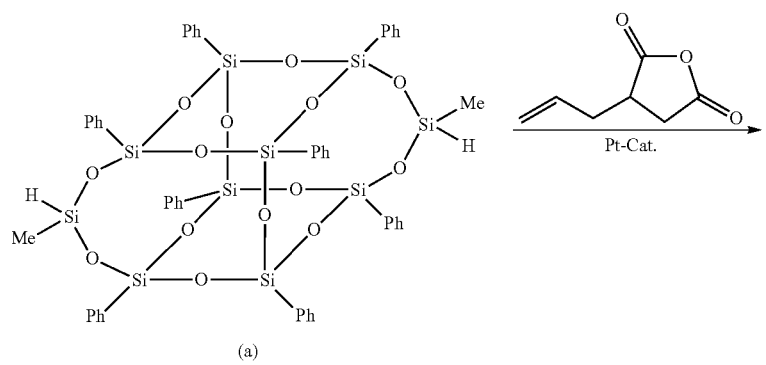

(a)

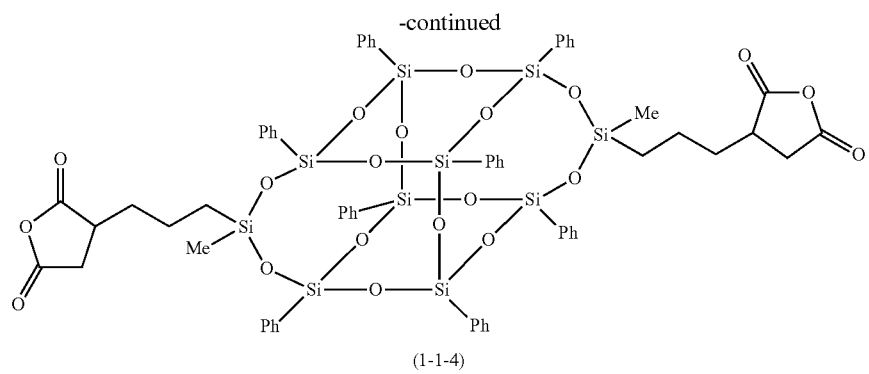

(1-1-4)

THF (150 ml) was added to the compound (a) (50.0 g, 43.3 mmol) under nitrogen atmosphere and suspended, and a platinum-divinylsiloxane complex (3 wt % toluene solution, 320 μl) was added thereto and heated to 90° C. Allylsuccinic anhydride (14.5 g, 103.5 mmol) was dropwise added thereto in 5 minutes, and the solution was heated for 7 hours while refluxing. After standing to cool, the solvent was distilled off under reduced pressure, and then methanol (150 ml) was added to the resulting residue and stirred at a room temperature for 2 hours. The resulting solid matter was filtered and dissolved in THF (150 ml), and activated carbon (6 g) was added thereto, followed by stirring the mixture at a room temperature for 2 hours. After filtering off the activated carbon, THF was distilled off under reduced pressure to obtain Compound (1-1-4) 55.9 g.

$^1$H-NMR (solvent: CDCl$_3$): δ (ppm); 0.32 (s, 6H), 0.70-0.79 (t, 4H), 1.32-1.42 (m, 6H), 1.74-1.80 (m, 2H), 1.89-1.99 (m, 2H), 2.24-2.37 (m, 2H), 2.51-2.60 (m, 2H), 7.15-7.56 (m, 40H).

$^{29}$Si-NMR (solvent: CDCl$_3$): δ (ppm); −18.1 (d, 2Si), −78.5 (s, 4Si), −79.4-1-79.8 (t, 4Si).

Example 3

Production of Compound (1-1-1)

Compound (1-1-1) was produced via the following route:

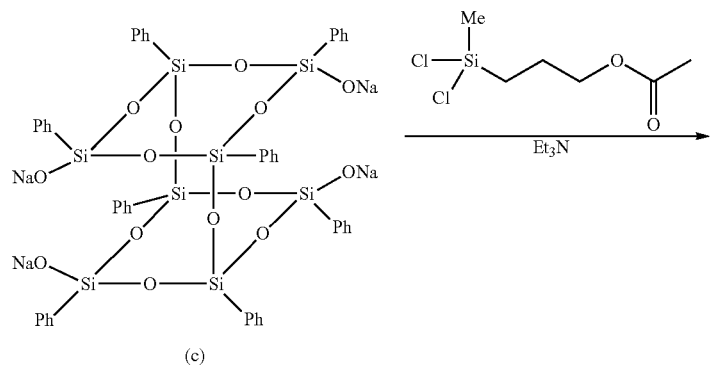

(c)

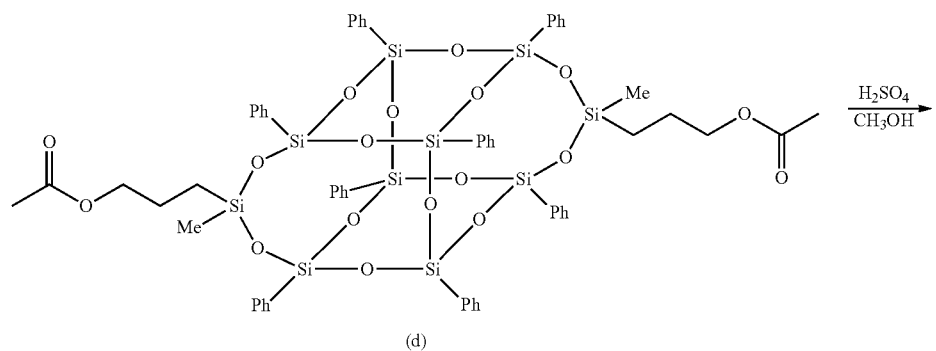

(d)

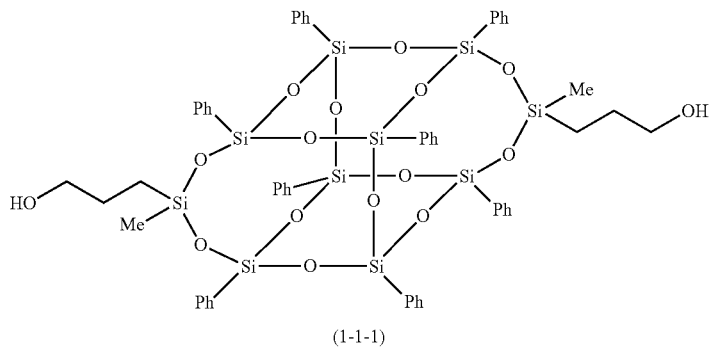

(1-1-1)

First Stage: Production of Compound (d)

3-Acetoxypropylmethyldichlorosilane (5.4 g, 25 mmol) was added to a mixture of a compound (c) (11.6 g, 10 mmol), triethylamine (2.5 g, 25 mmol) and THF (200 ml) under nitrogen atmosphere, and the solution was stirred at a room temperature for 3 hours. Toluene (200 ml) and water (100 ml) were added thereto and stirred, and the organic layer was washed with water and then dried on anhydrous magnesium sulfate. Toluene was distilled off under reduced pressure, and the residue thus obtained was washed with methanol and recrystallized from ethanol/ethyl acetate (100 ml) to obtain a compound (d) 6.51 g.

$^1$H-NMR (solvent: CDCl$_3$): δ (ppm); 0.31 (s, 6H), 0.72-0.75 (t, 4H), 1.70-1.74 (m, 4H), 1.88 (s, 6H), 3.91-3.94 (t, 4H), 7.18-7.52 (m, 40H).

$^{29}$Si-NMR (solvent: CDCl$_3$): δ (ppm); −17.8 (d, 2Si), −78.4 (s, 4Si), −79.3 (t, 4Si).

Second Stage: Production of Compound (1-1-1)

Conc. sulfuric acid (3 ml) was added to a mixture of the compound (d) (9.0 g, 6.85 mmol) and methanol (1,500 ml), and the solution was heated for 3 hours while refluxing. After standing to cool, methanol was distilled off under reduced pressure, and chloroform (200 ml) and water (100 ml) were added to the resulting residue and stirred. The organic layer was washed with water and dried on anhydrous magnesium sulfate, and then chloroform was distilled off under reduced pressure. The resulting residue was washed with methanol to obtain a compound (1-1-1) 5.00 g.

$^1$H-NMR (solvent: CDCl$_3$): δ (ppm); 0.31 (s, 6H), 0.71-0.75 (t, 4H), 1.60-1.66 (m, 4H), 3.45-3.48 (t, 4H), 7.18-7.54 (m, 40H).

$^{29}$Si-NMR (solvent: CDCl$_3$): δ (ppm); −17.4 (d, 2Si), −78.5 (s, 4Si), −79.5 (t, 4Si).

Example 4

Production of Compound (1-1-2)

Compound (1-1-2) was produced via the following route:

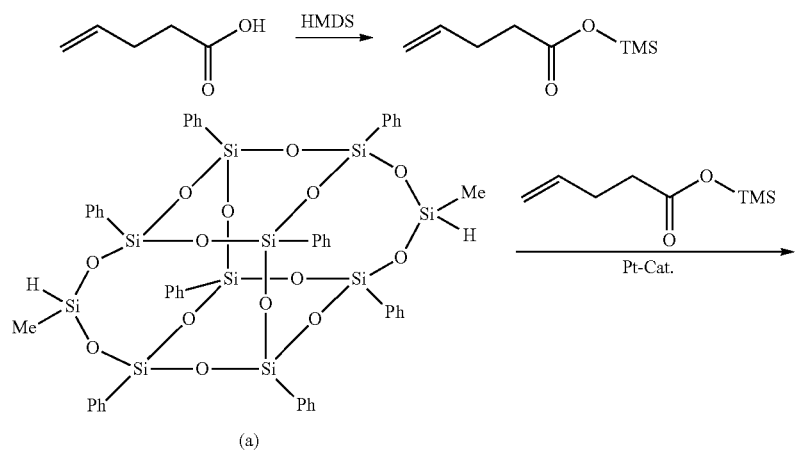

(a)

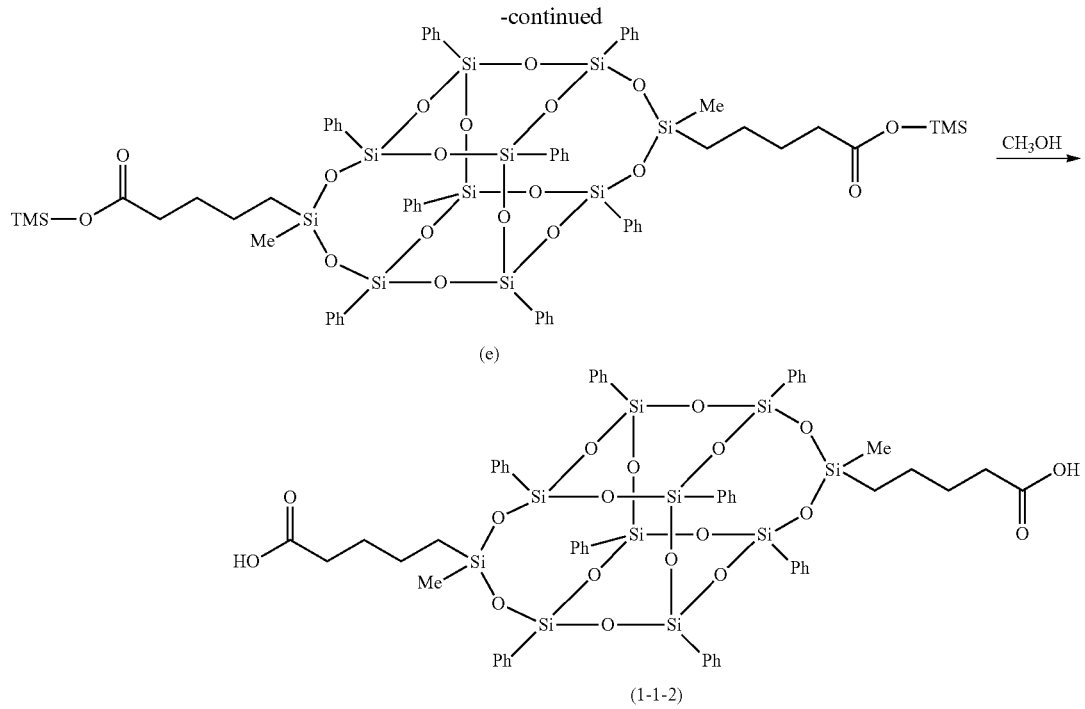

(e)

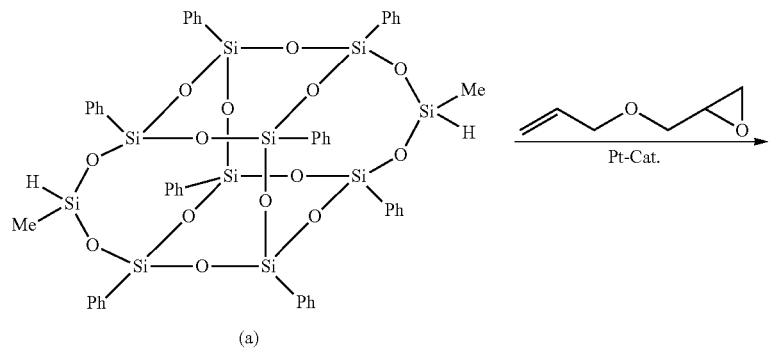

(1-1-2)

First Stage: Production of trimethylsilyl 4-pentenoate

A mixture of HMDS (88.6 g, 0.55 mol) and THF (21.5 g) was heated at 80° C. under nitrogen atmosphere, and a toluene (50 g) solution of 4-pentenoic acid (100 g, 1 mol) was dropwise added thereto. After dropwise adding, the solution was stirred at 100° C. for 2 hours and distilled under reduced pressure to obtain trimethylsilyl 4-pentenoate (130.2 g). This compound had a boiling point of 83 to 84'C/77.1 hPa.

Second Stage: Production of Compound (e)

Toluene (1,000 ml) was added to the compound (a) (100.0 g, 86.7 mmol) under nitrogen atmosphere and suspended, and a platinum-divinylsiloxane complex (3 wt % toluene solution, 50 µl) was added thereto and heated to 90° C. Trimethylsilyl 4-pentenoate (31.4 g, 182 mmol) was dropwise added thereto, and the solution was heated for 5 hours while refluxing. After standing to cool, toluene was distilled off under reduced pressure to obtain a crude compound (e) (92.9 g).

Third Stage: Production of Compound (1-1-2)

Methanol (1,000 ml) was added to the crude compound (e) (92.9 g, 61.8 mmol) and suspended, and the suspension was stirred at a room temperature for 3 hours. A solid matter filtered off from the suspension was dissolved in methanol/toluene, and activated carbon (2.7 g) was added thereto and stirred at a room temperature for 2 hours. The activated carbon was filtered off, and then the solvent was distilled off under reduced pressure. The residue was recrystallized from ethanol/ethyl acetate to obtain a compound (1-1-2) 75.0 g.

$^1$H-NMR (solvent: CDCl$_3$): δ (ppm); 0.28 (s, 6H), 0.72-0.75 (t, 4H), 1.40-1.43 (m, 4H), 1.53-1.56 (m, 4H), 2.08-2.11 (t, 4H), 7.18-7.53 (m, 40H).

$^{29}$Si-NMR (solvent: CDCl$_3$): δ (ppm); −17.7 (d, 2Si), −78.6 (s, 4Si), −79.6 (t, 4Si).

Example 5

Production of Compound (1-1-5)

Compound (1-1-5) was produced via the following route:

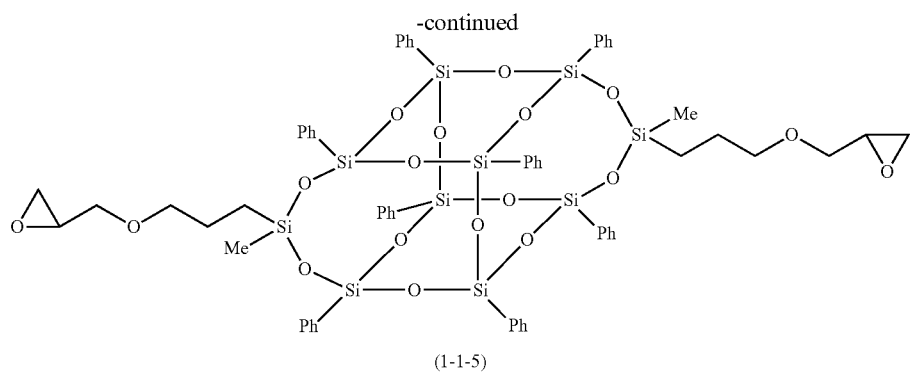

(1-1-5)

Toluene (50 ml) was added to the compound (a) (5:0 g, 4.33 mmol) under nitrogen atmosphere and suspended, and a platinum-divinylsiloxane complex (3 wt % toluene solution, 30 μl) was added thereto and heated to 90° C. Allyl glycidyl ether (1.04 g, 9.1 mmol) was dropwise added thereto, and the solution was heated for 3 hours while refluxing. After standing to cool, toluene (50 ml) and water (100 ml) were added thereto, and extracting practice was carried out. The organic layer was washed with water and then dried on anhydrous magnesium sulfate. Toluene was distilled off under reduced pressure, and the residue thus obtained was refined by means of silica gel chromatography (eluent solvent: toluene/ethyl acetate). The solvent was distilled off under reduced pressure, and then the residue was recrystallized from ethanol/ethyl acetate to obtain a compound (1-1-5) 1.6 g.

$^1$H-NMR (solvent: CDCl$_3$): δ (ppm); 0.30 (s, 6H), 0.73-0.76 (t, 4H), 1.66-1.72 (m, 4H), 2.42-2.44 (m, 2H), 2.64-2.66 (m, 2H), 2.95-2.98 (m, 2H), 3.15-3.19 (m, 2H), 3.28-3.39 (m, 4H), 3.44-3.48 (m, 2H), 7.18-7.53 (m, 40H).

$^{29}$Si-NMR (solvent: CDCl$_3$): δ (ppm); −17.4 (d, 2Si), −78.6 (s, 4Si), −79.5--79.6 (t, 4Si).

Example 6

Production of Compound (1-1-8)

Compound (1-1-8) was produced via the following route:

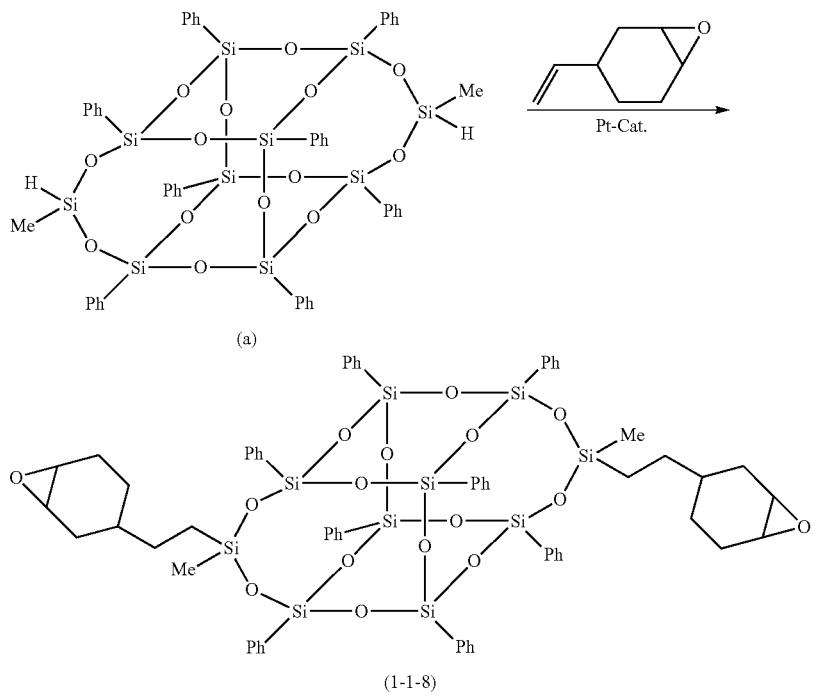

Toluene (30 ml) was added to the compound (a) (3.0 g, 2.60 mmol) under nitrogen atmosphere and suspended, and a platinum-divinylsiloxane complex (3 wt % toluene solution, 5 μl) was added thereto and heated to 90° C. 4-Vinyl-1-cyclohexene 1,2-epoxide (0.68 g, 5.46 mmol) was dropwise added thereto, and the solution was heated for 5 hours while refluxing. After standing to cool, toluene (30 ml) and water (70 ml) were added thereto, and extracting practice was carried out. The organic layer was washed with water and then dried on anhydrous magnesium sulfate. Toluene was distilled off under reduced pressure, and the residue thus obtained was refined by means of silica gel chromatography (eluent solvent: toluene/ethyl acetate). The solvent was distilled off under reduced pressure, and then the residue was recrystallized from ethanol/ethyl acetate to obtain a compound (1-1-8) 0.77 g.

$^1$H-NMR (solvent: CDCl$_3$): δ (ppm); 0.27 (s, 6H), 0.60-0.73 (m, 5H), 0.84-0.92 (m, 1H), 0.97-1.07 (m, 2H), 1.62-1.68 (m, 1H), 1.76-1.84 (m, 2H), 1.94-1.98 (m, 2H), 2.90-3.00 (m, 4H), 7.13-7.54 (m, 40H).

$^{29}$Si-NMR (solvent: CDCl$_3$): δ (ppm); −17.0-1-17.1 (d, 2Si), −78.7 (s, 4Si), −79.6 (s, 4Si).

Compounds shown in the following Table 1 to Table 28 can be produced according to the methods described in Examples 1 to 6. R$^1$, Q$^1$, Q$^2$ and Y$^1$ have the meanings described above.

TABLE 1

| No. | R$^1$ | Q$^1$ | Q$^2$ | Y$^1$ |
|---|---|---|---|---|
| 1-1-1 | phenyl | —CH$_3$ | Q$^2$-1-1 | —OH |
| 1-1-2 | phenyl | —CH$_3$ | Q$^2$-1-2 | —COOH |
| 1-1-3 | phenyl | —CH$_3$ | Q$^2$-1-1 | —OCOCH=CH$_2$ |
| 1-1-4 | phenyl | —CH$_3$ | Q$^2$-1-1 | methyl succinic anhydride group |
| 1-1-5 | phenyl | —CH$_3$ | Q$^2$-1-3 | glycidyl |
| 1-1-6 | phenyl | —CH$_3$ | Q$^2$-1-3 | 3-ethyl-3-oxetanylmethyl |
| 1-1-7 | phenyl | —CH$_3$ | Q$^2$-1-4 | —NH$_2$ |
| 1-1-8 | phenyl | —CH$_3$ | Q$^2$-1-5 | 3,4-epoxycyclohexyl |
| 1-2-1 | 3-methylphenyl | cyclohexyl | Q$^2$-2-1 | —COOH |
| 1-2-2 | 4-isopropylphenyl | —CH$_3$ | Q$^2$-2-2 | —OH |
| 1-2-3 | 2-chlorophenyl | —C$_2$H$_5$ | Q$^2$-2-3 | —Cl |
| 1-2-4 | 4-trifluoromethoxyphenyl | cyclopentyl | Q$^2$-2-4 | —CH=CHCOOCH(CH$_3$)$_2$ |

TABLE 1-continued

| No. | R¹ | Q¹ | Q² | Y¹ |
|---|---|---|---|---|
| 1-2-5 | phenyl | —OCH₃ | Q²-2-5 | —OCOC(CF₃)=CH₂ |
| 1-2-6 | 3-ethylphenyl | —CH₂CH=CH₂ | Q²-2-6 | —CHO |
| 1-2-7 | 2,3-difluorophenyl | —C₂H₅ | Q²-2-7 | —COOH |
| 1-2-8 | 3,5-difluorophenyl | —OCH₃ | Q²-2-8 | epoxycyclohexyl |
| 1-2-9 | 3-chlorophenyl | —CH(CH₃)₂ | Q²-2-9 | epoxyethyl |

TABLE 2

| No. | R¹ | Q¹ | Q² | Y¹ |
|---|---|---|---|---|
| 1-3-1 | phenyl | —CH₃ | Q²-3-1 | —OH |
| 1-3-2 | phenyl | phenyl | Q²-3-2 | —NH₂ |
| 1-3-3 | phenyl | —CH₃ | Q²-3-1 | —COOH |
| 1-3-4 | 3-fluorophenyl | —CH(CH₃)₂ | Q²-3-2 | —OCOC(CH)=CH₂ |
| 1-3-5 | phenyl | cyclopentyl | Q²-3-4 | —Br |
| 1-3-6 | 4-(trifluoromethyl)phenyl | —CH₃ | Q²-3-5 | methylsuccinic anhydride |

TABLE 2-continued

| No. | R¹ | Q¹ | Q² | Y¹ |
|---|---|---|---|---|
| 1-3-7 | phenyl | —CH₃ | Q²-3-2 | —NH₂ |
| 1-3-8 | phenyl | —CH₃ | Q²-3-6 | —NH₂ |
| 1-3-9 | 4-methylphenyl | —CH₃ | Q²-3-7 | —OH |
| 1-3-10 | 2-fluorophenyl | —C₂H₅ | Q²-3-8 | N-maleimidyl |
| 1-3-11 | 3-(trifluoromethyl)phenyl | —C₃H₇ | Q²-3-8 | —OCOCH=CH₂ |
| 1-3-12 | phenyl | —CH(CH₃)₂ | Q²-3-9 | —OCOC(F)=CH₂ |
| 1-3-13 | 4-(trifluoromethoxy)phenyl | cyclopentyl | Q²-3-9 | —OCH=CH₂ |
| 1-3-14 | phenyl | —OCH₃ | Q²-3-10 | —Cl |
| 1-4-1 | 3-ethylphenyl | —CH₂CH=CH₂ | Q²-4-1 | —CHO |
| 1-4-2 | phenyl | —C₂H₅ | Q²-4-1 | —OH |
| 1-4-3 | phenyl | —OCH₃ | Q²-4-1 | —COOCH₃ |

TABLE 3

| No. | R¹ | Q¹ | Q² | Y¹ |
|---|---|---|---|---|
| 1-4-4 | phenyl | —CH₃ | Q²-4-2 | —OH |
| 1-4-5 | phenyl | phenyl | Q²-4-3 | —COCH=CH₂ |

TABLE 3-continued

| No. | R¹ | Q¹ | Q² | Y¹ |
|---|---|---|---|---|
| 1-4-6 | phenyl | —CH₃ | Q²-4-4 | —OH |
| 1-4-7 | 3-fluorophenyl | —CH(CH₃)₂ | Q²-4-5 | —Br |
| 1-5-1 | phenyl | phenyl | Q²-5-1 | —OH |
| 1-5-2 | phenyl | —CH₃ | Q²-5-1 | —COOH |
| 1-5-3 | phenyl | phenyl | Q²-5-1 | —NH₂ |
| 1-5-4 | 4-isopropylphenyl | cyclohexyl | Q²-5-2 | N-maleimidyl |
| 1-5-5 | 3-methylphenyl | —CH₂CH=CH₂ | Q²-5-2 | —OCH=CH₂ |
| 1-5-6 | 4-methoxyphenyl | —CH₃ | Q²-5-2 | methyl succinic anhydride |
| 1-5-7 | phenyl | —C₂H₅ | Q²-5-3 | —COOH |
| 1-5-8 | 4-chlorophenyl | —OCH₃ | Q²-5-3 | —OH |
| 1-5-9 | phenyl | —CH₃ | Q²-5-4 | glycidyl |
| 1-5-10 | 4-(trifluoromethyl)phenyl | cyclopentyl | Q²-5-4 | 3-ethyl-3-methyloxetanyl |
| 1-5-11 | phenyl | —C₄H₉ | Q²-5-5 | —Br |

TABLE 3-continued
| No. | R¹ | Q¹ | Q² | Y¹ |
|---|---|---|---|---|
| 1-5-12 | 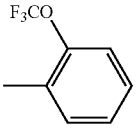 F₃CO | —CH(CH₃)₂ | Q²-5-5 | —OCOC(F)=CH₂ |
| 1-5-13 | 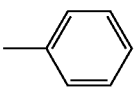 | —OCH₃ | Q²-5-5 | OH |
TABLE 4
| No. | R¹ | Q¹ | Q² | Y¹ |
|---|---|---|---|---|
| 1-6-1 | 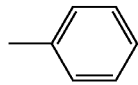 | —CH(CH₃)₂ | Q²-6-1 | —OH |
| 1-6-2 | 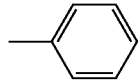 | 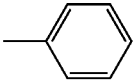 | Q²-6-2 | —COOH |
| 1-6-3 | 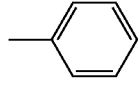 | —OCH₃ | Q²-6-2 | —OH |
| 1-6-4 | 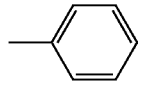 | —CH₃ | Q²-6-3 | —OH |
| 1-6-5 | 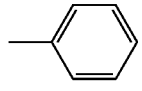 | —CH₂CH=CH₂ | Q²-6-3 | —Br |
| 1-6-6 | 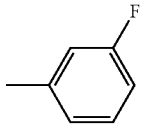 F | —OCH₃ | Q²-6-4 | —Cl |
| 1-6-7 | 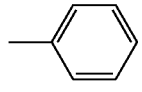 | 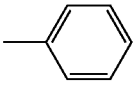 | Q²-6-5 | 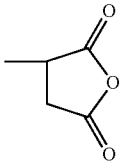 |
| 1-7-1 | 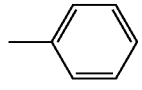 | —CH₃ | Q²-7-1 | —COOH |
| 1-7-2 | 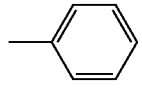 | 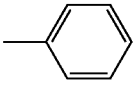 | Q²-7-1 | —NH₂ |
| 1-7-3 | 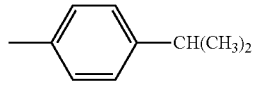 —CH(CH₃)₂ | 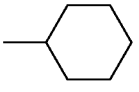 | Q²-7-2 | —OCOC(CH)=CH₂ |
| 1-7-4 | 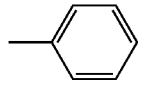 | —CH₃ | Q²-7-2 | 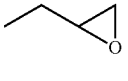 |

TABLE 4-continued
| No. | R¹ | Q¹ | Q² | Y¹ |
|---|---|---|---|---|
| 1-7-5 | 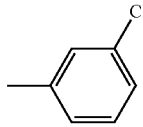 | —C₂H₅ | Q²-7-3 | —OH |
| 1-7-6 | 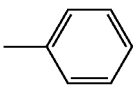 | —C₂H₅ | Q²-7-3 | 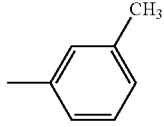 |
| 1-7-7 | 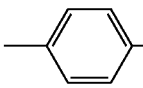 | —C₂H₅ | Q²-7-4 | —COCl |
| 1-7-8 |  | 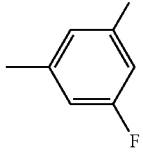 | Q²-7-5 | —COOH |
TABLE 5
| No. | R¹ | Q¹ | Q² | Y¹ |
|---|---|---|---|---|
| 1-8-1 | 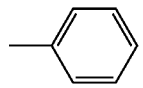 | —C₂H₅ | Q²-8-1 | —COOH |
| 1-8-2 |  | 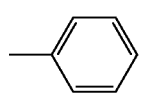 | Q²-8-2 | —OH |
| 1-8-3 | 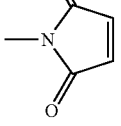 | —CH₃ | Q²-8-3 | 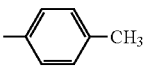 |
| 1-8-4 | 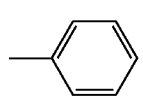 | —CH(CH₃)₂ | Q²-8-4 | —NH₂ |
| 1-8-5 |  | 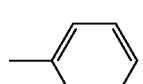 | Q²-8-5 | —OH |
| 1-9-1 | 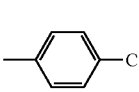 | —CH₃ | Q²-9-1 | —OH |
| 1-9-2 |  | 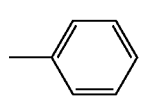 | Q²-9-2 | —COOH |
| 1-9-3 |  | 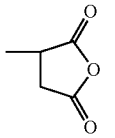 | Q²-9-3 | 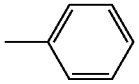 |
| 1-9-4 | 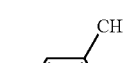 | —CH₃ | Q²-9-4 | —COOH |
| 1-9-5 | 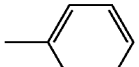 | —C₂H₅ | Q²-9-5 | —Br |
| 1-10-1 |  | 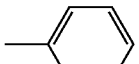 | Q²-10-1 | —COOH |
| 1-10-2 | 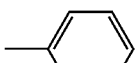 | —OCH₃ | Q²-10-2 | —OH |
| 1-10-3 |  | 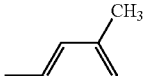 | Q²-10-3 | —COOCH₃ |
| 1-10-4 | 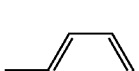 | —C₂H₅ | Q²-10-4 | —COCH=CH₂ |
| 1-10-5 |  | —C₂H₅ | Q²-10-5 |  |

TABLE 6

| No. | R¹ | Q¹ | Q² | Y¹ |
|---|---|---|---|---|
| 1-11-1 | —phenyl | —CH₃ | Q²-11-1 | —COOH |
| 1-11-2 | —phenyl | —phenyl | Q²-11-2 | —OH |
| 1-11-3 | —C₆H₄-Cl (4-Cl phenyl) | —C₂H₅ | Q²-11-3 | —COCl |
| 1-11-4 | —C₆H₃F₂ (3,4-difluorophenyl) | —Cl | Q²-11-4 | (epoxide, —CH₂-CH(O)CH₂—) |
| 1-11-5 | —phenyl | —phenyl | Q²-11-5 | (methyl succinic anhydride) |
| 1-12-1 | —phenyl | —CH₃ | Q²-12-1 | —OCOCH=CH₂ |
| 1-12-2 | —C₆H₄-Cl (4-Cl phenyl) | —phenyl | Q²-12-2 | —OH |
| 1-12-3 | —phenyl | —CH(CH₃)₂ | Q²-12-3 | —COOH |
| 1-12-4 | —phenyl | —phenyl | Q²-12-4 | —OH |
| 1-12-5 | —C₆H₄-CH₃ (2-methylphenyl) | —cyclopentyl | Q²-12-5 | —COCl |
| 1-13-1 | —phenyl | —CH₃ | Q²-13-1 | —COOH |
| 1-13-2 | —phenyl | —CH=CH₂ | Q²-13-2 | —OH |
| 1-13-3 | —C₆H₄F (3-fluorophenyl) | —C₃H₇ | Q²-13-3 | (methyl succinic anhydride) |
| 1-13-4 | —C₆H₃F₂ (3,5-difluorophenyl) | —C₂H₅ | Q²-13-4 | —OCH=CH₂ |
| 1-13-5 | —phenyl | —cyclohexyl | Q²-13-5 | (3-ethyl-3-methyloxetane) |

TABLE 7

| No. | R¹ | Q¹ | Q² | Y¹ |
|---|---|---|---|---|
| 1-14-1 | —C₆H₄—OC₂H₅ (4-ethoxyphenyl) | —CH₃ | Q²-14-1 | —COOH |
| 1-14-2 | —phenyl | —CH₃ | Q²-14-2 | —OH |
| 1-14-3 | —phenyl | —C₃H₇ | Q²-14-3 | (epoxide) |
| 1-14-4 | —C₆H₄—CH₃ (3-methylphenyl) | —H | Q²-14-4 | —COOH |
| 1-14-5 | —phenyl | —phenyl | Q²-14-5 | —OH |

TABLE 7-continued

| No. | R¹ | Q¹ | Q² | Y¹ |
|---|---|---|---|---|
| 1-15-1 | phenyl | —CH$_3$ | Q²-15-1 | —COOH |
| 1-15-2 | 4-(OCF$_3$)phenyl | 4-Cl-phenyl | Q²-15-2 | N-methylmaleimide |
| 1-15-3 | phenyl | —C$_2$H$_5$ | Q²-15-3 | 7-oxabicyclo[4.1.0]heptyl |
| 1-15-4 | phenyl | phenyl | Q²-15-4 | —OCOCH=CH$_2$ |
| 1-15-5 | phenyl | —CH(CH$_3$)$_2$ | Q²-15-5 | —NH$_2$ |
| 1-16-1 | phenyl | —CH$_3$ | Q²-16-1 | —COOH |
| 1-16-2 | 4-Cl-phenyl | —C$_4$H$_9$ | Q²-16-2 | —OH |
| 1-16-3 | phenyl | cyclopentyl | Q²-16-3 | —OH |
| 1-16-4 | 3-F-phenyl | —C$_2$H$_5$ | Q²-16-4 | —NH$_2$ |
| 1-16-5 | phenyl | —CH$_3$ | Q²-16-5 | —CN |

TABLE 8

| No. | R¹ | Q¹ | Q² | Y¹ |
|---|---|---|---|---|
| 1-17-1 | phenyl | —C$_2$H$_5$ | Q²-17-1 | —COOH |
| 1-17-2 | 3-F-phenyl | —CH$_3$ | Q²-17-2 | —OH |

TABLE 8-continued

| No. | R¹ | Q¹ | Q² | Y¹ |
|---|---|---|---|---|
| 1-17-3 | 4-methoxyphenyl | —CH₃ | Q²-17-3 | —COCl |
| 1-17-4 | phenyl | phenyl | Q²-17-4 | —OH |
| 1-17-5 | phenyl | phenyl | Q²-17-5 | —NH₂ |
| 1-18-1 | 4-chlorophenyl | —C₃H₇ | Q²-18-1 | —CH=CHCH=CH₂ |
| 1-18-2 | phenyl | 3-methylphenyl | Q²-18-2 | N-maleimidyl |
| 1-18-3 | phenyl | —CH(CH₃)₂ | Q²-18-3 | —OH |
| 1-18-4 | phenyl | phenyl | Q²-18-4 | 3,3-diethyloxetanyl |
| 1-18-5 | phenyl | —CH(CH₃)₂ | Q²-18-5 | —NH₂ |
| 1-19-1 | 4-methylphenyl | cyclohexyl | Q²-19-1 | methylsuccinic anhydride |
| 1-19-2 | phenyl | cyclopentyl | Q²-19-2 | —OH |
| 1-19-3 | phenyl | —CH₃ | Q²-19-3 | —COOH |
| 1-19-4 | 3-fluorophenyl | —CH₃ | Q²-19-4 | —CH=CH₂ |
| 1-19-5 | phenyl | cyclopentyl | Q²-19-5 | glycidyl |

TABLE 9
| No. | R¹ | Q¹ | Q² | Y¹ |
|---|---|---|---|---|
| 1-20-1 | 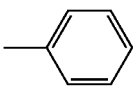 | 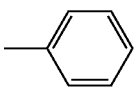 | Q²-20-1 | —OH |
| 1-20-2 | 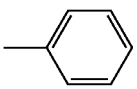 | —CH=CH₂ | Q²-20-2 | —COOH |
| 1-20-3 | 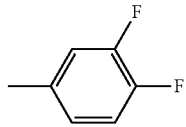 | —CH₃ | Q²-20-3 | 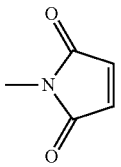 |
| 1-20-4 | 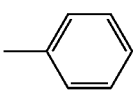 | 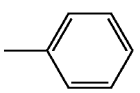 | Q²-20-4 | —CHO |
| 1-20-5 | 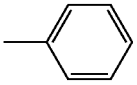 | —C₃H₇ | Q²-20-5 | —OH |
| 1-21-1 | 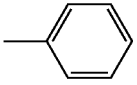 | —C₃H₇ | Q²-21-1 | —COOH |
| 1-21-2 | 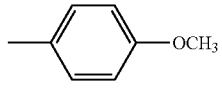 | 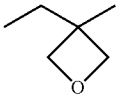 | Q²-21-2 | 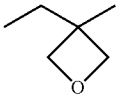 |
| 1-21-3 | 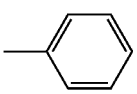 | —C₂H₅ | Q²-21-3 | —Br |
| 1-21-4 | 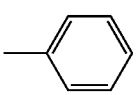 | 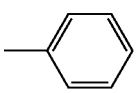 | Q²-21-4 | —OCOCH=CH₂ |
| 1-21-5 | 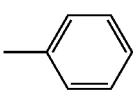 | —CH₃ | Q²-21-5 | 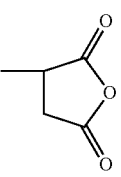 |
| 1-22-1 | 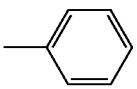 | 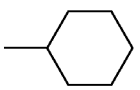 | Q²-22-1 | —COOH |
| 1-22-2 | 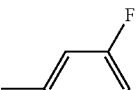 | —OCH₃ | Q²-22-2 | —OCOC(CF₃)=CH₂ |
| 1-22-3 | 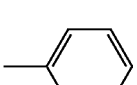 | 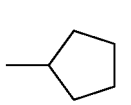 | Q²-22-3 | —COOH |

TABLE 9-continued

| No. | R¹ | Q¹ | Q² | Y¹ |
|---|---|---|---|---|
| 1-22-4 | H₃C–(o-tolyl)– | —CH₃ | Q²-22-4 | —OH |
| 1-22-5 | phenyl– | —CH(CH₃)₂ | Q²-22-5 | —NH₂ |

TABLE 10

| No. | R¹ | Q¹ | Q² | Y¹ |
|---|---|---|---|---|
| 1-23-1 | phenyl– | cyclopentyl | Q²-23-1 | —COOH |
| 1-23-2 | phenyl– | —CH₃ | Q²-23-2 | succinic anhydride |
| 1-23-3 | m-tolyl– (CH₃) | —CH₃ | Q²-23-3 | —OCH=CH₂ |
| 1-23-4 | phenyl– | phenyl– | Q²-23-4 | —OH |
| 1-23-5 | phenyl– | —CH₃ | Q²-23-5 | —NH₂ |
| 1-24-1 | phenyl– | cyclohexyl | Q²-24-1 | succinic anhydride |
| 1-24-2 | phenyl– | —C₂H₅ | Q²-24-2 | —COCl |
| 1-24-3 | 3,4-difluorophenyl– | —CH(CH₃)₂ | Q²-24-3 | —NH₂ |
| 1-24-4 | phenyl– | phenyl– | Q²-24-4 | —COOH |
| 1-24-5 | phenyl– | —CH₃ | Q²-24-5 | —OCOCH=CH₂ |
| 1-25-1 | phenyl– | —OCH₃ | Q²-25-1 | —COOH |
| 1-25-2 | 3-fluorophenyl– | —C₃H₇ | Q²-25-2 | glycidyl (epoxide) |
| 1-25-3 | phenyl– | —CH(CH₃)₂ | Q²-25-3 | —COOH |
| 1-25-4 | phenyl– | —CH₃ | Q²-25-4 | —NH₂ |
| 1-25-5 | phenyl– | —OCH₃ | Q²-25-5 | —OH |

TABLE 11

| No. | R¹ | Q¹ | Q² | Y¹ |
|---|---|---|---|---|
| 1-26-1 | phenyl– | cyclohexyl | Q²-26-1 | —COOH |
| 1-26-2 | phenyl– | —CH₃ | Q²-26-2 | —OH |

TABLE 11-continued
| No. | R¹ | Q¹ | Q² | Y¹ |
|---|---|---|---|---|
| 1-26-3 | 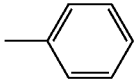 | —CH₃ | Q²-26-3 | 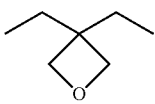 |
| 1-26-4 | 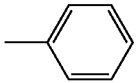 | 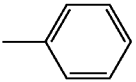 | Q²-26-4 | 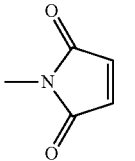 |
| 1-26-5 | 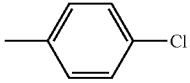 | —C₃H₇ | Q²-26-5 | —COOH |
| 1-27-1 | 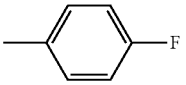 | 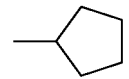 | Q²-27-1 | —COOH |
| 1-27-2 | 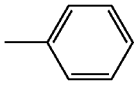 | —C₄H₉ | Q²-27-2 | 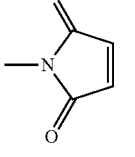 |
| 1-27-3 | 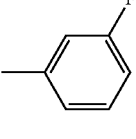 | —CH₃ | Q²-27-3 | —NH₂ |
| 1-27-4 | 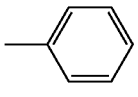 | 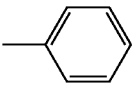 | Q²-27-4 | 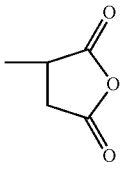 |
| 1-27-5 | 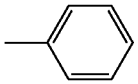 | —CH₃ | Q²-27-5 | 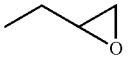 |
| 1-28-1 | 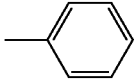 | —C₂H₅ | Q²-28-1 | —COOH |
| 1-28-2 | 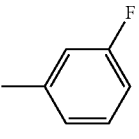 | —CH₃ | Q²-28-2 | —OH |
| 1-28-3 | 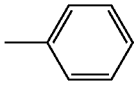 | 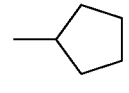 | Q²-28-3 | —COOH |
| 1-28-4 | 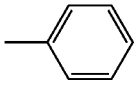 | —OCH₃ | Q²-28-4 | 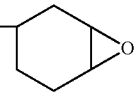 |

TABLE 11-continued

| No. | $R^1$ | $Q^1$ | $Q^2$ | $Y^1$ |
|---|---|---|---|---|
| 1-28-5 | phenyl | phenyl | $Q^2$-28-5 | —$NH_2$ |

TABLE 12

| No. | $R^1$ | $Q^1$ | $Q^2$ | $Y^1$ |
|---|---|---|---|---|
| 1-29-1 | 3,5-difluorophenyl | —$OCH_3$ | $Q^2$-29-1 | —COOH |
| 1-29-2 | phenyl | —$CH_3$ | $Q^2$-29-2 | —OH |
| 1-29-3 | phenyl | phenyl | $Q^2$-29-3 | —$OCOC(CF_3)$=$CH_2$ |
| 1-29-4 | phenyl | phenyl | $Q^2$-29-4 | —$NH_2$ |
| 1-29-5 | phenyl | —$CH(CH_3)_2$ | $Q^2$-29-5 | —COOH |
| 1-30-1 | 4-fluorophenyl | —$C_2H_5$ | $Q^2$-30-1 | —OH |
| 1-30-2 | phenyl | —$CH_3$ | $Q^2$-30-2 | —OCOCH=$CH_2$ |
| 1-30-3 | phenyl | phenyl | $Q^2$-30-3 | —COCl |

TABLE 12-continued

| No. | $R^1$ | $Q^1$ | $Q^2$ | $Y^1$ |
|---|---|---|---|---|
| 1-30-4 | phenyl | phenyl | $Q^2$-30-4 | succinic anhydride group |
| 1-30-5 | phenyl | —$CH_3$ | $Q^2$-30-5 | —COOH |
| 1-31-1 | phenyl | —$CH_3$ | $Q^2$-31-1 | glycidyl (epoxide) |
| 1-31-2 | 3,4-difluorophenyl | 3-fluorophenyl | $Q^2$-31-2 | —OH |
| 1-31-3 | phenyl | cyclohexyl | $Q^2$-31-3 | —COOH |
| 1-31-4 | phenyl | —$OCH_3$ | $Q^2$-31-4 | —OCH=$CH_2$ |
| 1-31-5 | phenyl | phenyl | $Q^2$-31-5 | —OH |

TABLE 13

| No. | $R^1$ | $Q^1$ | $Q^2$ | $Y^1$ |
|---|---|---|---|---|
| 1-32-1 | phenyl | —$C_3H_7$ | $Q^2$-32-1 | —OCH=$CH_2$ |
| 1-32-2 | phenyl | cyclopentyl | $Q^2$-32-2 | —COOH |
| 1-32-3 | phenyl | 3-methylphenyl | $Q^2$-32-3 | —$NH_2$ |

TABLE 13-continued
| No. | R¹ | Q¹ | Q² | Y¹ |
|---|---|---|---|---|
| 1-32-4 | 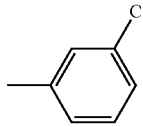 | 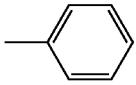 | Q²-32-4 | —OH |
| 1-32-5 | 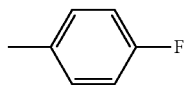 | —C₂H₅ | Q²-32-5 | —OCOC(CH₃)=CH₂ |
| 1-33-1 | 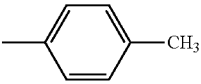 | 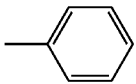 | Q²-33-1 | —CN |
| 1-33-2 | 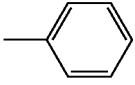 | —CH₃ | Q²-33-2 | —COOH |
| 1-33-3 | 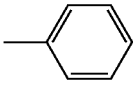 | —CH(CH₃)₂ | Q²-33-3 | 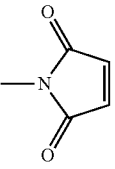 |
| 1-33-4 | 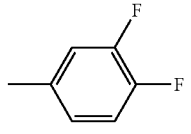 | 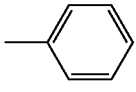 | Q²-33-4 | —COOH |
| 1-33-5 | 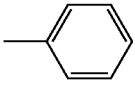 | —CH₃ | Q²-33-5 | 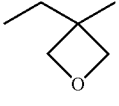 |
| 1-34-1 | 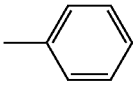 | 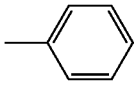 | Q²-34-1 | —OH |
| 1-34-2 | 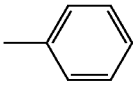 | 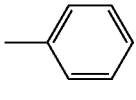 | Q²-34-2 | 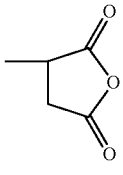 |
| 1-34-3 | 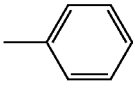 | —CH₃ | Q²-34-3 | —NH₂ |
| 1-34-4 | 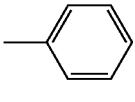 | —OCH₃ | Q²-34-4 | —C≡CH |
| 1-34-5 | 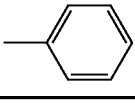 | 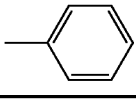 | Q²-34-5 | —OH |

TABLE 14

| No. | R¹ | Q¹ | Q² | Y¹ |
|---|---|---|---|---|
| 1-35-1 | phenyl | phenyl | Q²-35-1 | —OH |
| 1-35-2 | phenyl | phenyl | Q²-35-2 | —COOH |
| 1-35-3 | phenyl | —CH₃ | Q²-35-3 | N-methylmaleimide |
| 1-35-4 | phenyl | phenyl | Q²-35-4 | —NH₂ |
| 1-35-5 | phenyl | —CH(CH₃)₂ | Q²-35-5 | epoxyethyl-CH₂– |
| 1-36-1 | 3-methylphenyl | cyclopentyl | Q²-36-1 | —CH=CHCH=CH₂ |
| 1-36-2 | phenyl | —C₃H₇ | Q²-36-2 | —OH |
| 1-36-3 | phenyl | —C₂H₅ | Q²-36-3 | —Br |
| 1-36-4 | 4-methoxyphenyl | 3,4-difluorophenyl | Q²-36-4 | methyl-substituted succinic anhydride |
| 1-36-5 | phenyl | —CH₃ | Q²-36-5 | —COOH |
| 1-37-1 | 4-fluorophenyl | —OC₂H₅ | Q²-37-1 | 3,3-diethyloxetanyl |
| 1-37-2 | phenyl | phenyl | Q²-37-2 | —OH |
| 1-37-3 | 3-fluorophenyl | cyclohexyl | Q²-37-3 | —CHO |

TABLE 14-continued

| No. | R¹ | Q¹ | Q² | Y¹ |
|---|---|---|---|---|
| 1-37-4 | (phenyl) | —OCH₃ | Q²-37-4 | —OH |
| 1-37-5 | (3-fluorophenyl) | (3-fluorophenyl) | Q²-37-5 | (methyl succinic anhydride) |

TABLE 15

| No. | R¹ | Q¹ | Q² | Y¹ |
|---|---|---|---|---|
| 1-38-1 | (phenyl) | (4-methoxyphenyl) | Q²-38-1 | NH₂ |
| 1-38-2 | (4-chlorophenyl) | (phenyl) | Q²-38-2 | —OCOCH=CH₂ |
| 1-38-3 | (phenyl) | —C₃H₇ | Q²-38-3 | —OCH=CH₂ |
| 1-38-4 | (phenyl) | (phenyl) | Q²-38-4 | —OH |
| 1-38-5 | (phenyl) | —CH₃ | Q²-38-5 | —OCH=CH₂ |
| 1-39-1 | (phenyl) | (phenyl) | Q²-39-1 | (maleimide) |
| 1-39-2 | (4-methoxyphenyl) | —CH(CH₃)₂ | Q²-39-2 | —OH |
| 1-39-3 | (3,4-difluorophenyl) | —CH₃ | Q²-39-3 | (methyl succinic anhydride) |
| 1-39-4 | (phenyl) | (phenyl) | Q²-39-4 | —COOH |
| 1-39-5 | (3-fluorophenyl) | (phenyl) | Q²-39-5 | (cyclohexene oxide) |

TABLE 15-continued

| No. | R¹ | Q¹ | Q² | Y¹ |
|---|---|---|---|---|
| 1-40-1 | phenyl | —OCH₃ | Q²-40-1 | —OH |
| 1-40-2 | phenyl | phenyl | Q²-40-2 | —NH₂ |
| 1-40-3 | 3-fluorophenyl | —CH(CH₃)₂ | Q²-40-3 | —OH |
| 1-40-4 | phenyl | —C₂H₅ | Q²-40-4 | —OCH=CH₂ |
| 1-40-5 | 4-chlorophenyl | phenyl | Q²-40-5 | —COOH |

TABLE 16

| No. | R¹ | Q¹ | Q² | Y¹ |
|---|---|---|---|---|
| 1-41-1 | 3-fluorophenyl | —CH₃ | Q²-41-1 | —COOH |
| 1-41-2 | 4-fluorophenyl | phenyl | Q²-41-2 | —NH₂ |
| 1-41-3 | phenyl | —OC₂H₅ | Q²-41-3 | —OCOC(CH)=CH₂ |
| 1-41-4 | 4-chlorophenyl | 4-methoxyphenyl | Q²-41-4 | —NH₂ |
| 1-41-5 | phenyl | —C₄H₉ | Q²-41-5 | glycidyl (epoxide) |
| 1-42-1 | phenyl | 3-fluorophenyl | Q²-42-1 | —OH |
| 1-42-2 | phenyl | —CH(CH₃)₂ | Q²-42-2 | —NH₂ |
| 1-42-3 | phenyl | —CH₃ | Q²-42-3 | —COOH |

TABLE 16-continued
| No. | R¹ | Q¹ | Q² | Y¹ |
|---|---|---|---|---|
| 1-42-4 | 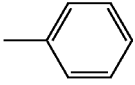 | 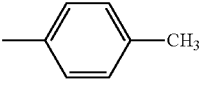—CH₃ | Q²-42-4 | 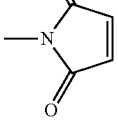 |
| 1-42-5 | 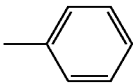 | 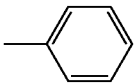 | Q²-42-5 | 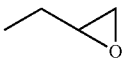 |
| 1-43-1 | 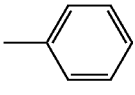 | —C₂H₅ | Q²-43-1 | 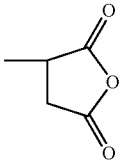 |
| 1-43-2 | 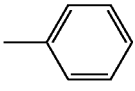 | 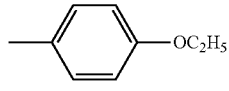—OC₂H₅ | Q²-43-2 | —CH=CH₂ |
| 1-43-3 | 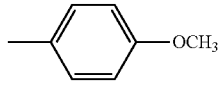—OCH₃ | —CH(CH₃)₂ | Q²-43-3 | —COOH |
| 1-43-4 | 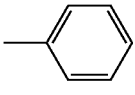 | —CH₃ | Q²-43-4 | —OCOCH=CH₂ |
| 1-43-5 | 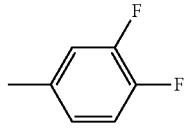 | 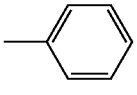 | Q²-43-5 | 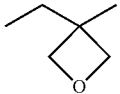 |
TABLE 17
| No. | R¹ | Q¹ | Q² | Y¹ |
|---|---|---|---|---|
| 1-44-1 | 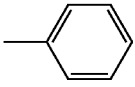 | 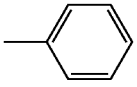 | Q²-44-1 | —COOH |
| 1-44-2 | 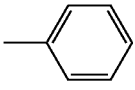 | —CH₃ | Q²-44-2 | —OCH=CH₂ |
| 1-44-3 | 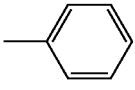 | —CH(CH₃)₂ | Q²-44-3 | 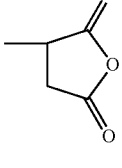 |
| 1-44-4 | 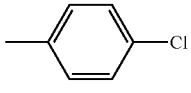—Cl | —OCH₃ | Q²-44-4 | —OH |
| 1-44-5 | 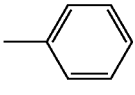 | —C₃H₇ | Q²-44-5 | —COOH |

TABLE 17-continued

| No. | R¹ | Q¹ | Q² | Y¹ |
|---|---|---|---|---|
| 1-45-1 | phenyl | 3-methylphenyl | Q²-45-1 | 3-ethyloxetan-3-ylmethyl |
| 1-45-2 | 4-methoxyphenyl | —CH=CH₂ | Q²-45-2 | —NH₂ |
| 1-45-3 | phenyl | —CH₃ | Q²-45-3 | —COOH |
| 1-45-4 | 3,4-difluorophenyl | phenyl | Q²-45-4 | —NH₂ |
| 1-45-5 | phenyl | 4-ethoxyphenyl | Q²-45-5 | oxiranylmethyl |
| 1-46-1 | phenyl | —CH₃ | Q²-46-1 | —OH |
| 1-46-2 | phenyl | 4-ethoxyphenyl | Q²-46-2 | —CN |
| 1-46-3 | phenyl | —C₃H₇ | Q²-46-3 | oxiranylmethyl |
| 1-46-4 | 3-fluorophenyl | cyclopentyl | Q²-46-4 | —COOH |
| 1-46-5 | phenyl | 3-fluorophenyl | Q²-46-5 | —OCOC(CF₃)=CH₂ |

TABLE 18

| No. | R¹ | Q¹ | Q² | Y¹ |
|---|---|---|---|---|
| 1-47-1 | 3-methoxyphenyl | phenyl | Q²-47-1 | —COOH |
| 1-47-2 | phenyl | —C₄H₉ | Q²-47-2 | 3-methyloxetan-3-ylmethyl |

TABLE 18-continued

| No. | R¹ | Q¹ | Q² | Y¹ |
|---|---|---|---|---|
| 1-47-3 | phenyl | cyclohexyl | Q²-47-3 | N-maleimidyl |
| 1-47-4 | 4-chlorophenyl | —OCH(CH₃)₂ | Q²-47-4 | —OH |
| 1-47-5 | phenyl | —CH₃ | Q²-47-5 | methyl succinic anhydride |
| 1-48-1 | phenyl | 4-chlorophenyl | Q²-48-1 | —COOH |
| 1-48-2 | 2-fluorophenyl | —CH₃ | Q²-48-2 | —NH₂ |
| 1-48-3 | phenyl | —CH₃ | Q²-48-3 | glycidyl |
| 1-48-4 | 4-methoxyphenyl | phenyl | Q²-48-4 | —OH |
| 1-48-5 | phenyl | phenyl | Q²-48-5 | —OCOCH=CH₂ |
| 1-49-1 | phenyl | —CH(CH₃)₂ | Q²-49-1 | methyl succinic anhydride |
| 1-49-2 | phenyl | 4-chlorophenyl | Q²-49-2 | —COCl |
| 1-49-3 | phenyl | —C₃H₇ | Q²-49-3 | —OCH=CH₂ |

TABLE 18-continued
| No. | R¹ | Q¹ | Q² | Y¹ |
|---|---|---|---|---|
| 1-49-4 | 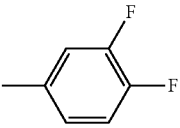 |  | Q²-49-4 | —NH₂ |
| 1-49-5 | 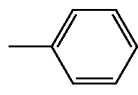 | 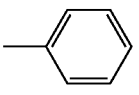 | Q²-49-5 | 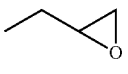 |
TABLE 19
| No. | R¹ | Q¹ | Q² | Y¹ |
|---|---|---|---|---|
| 1-50-1 | 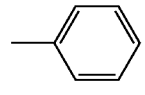 | —CH(CH₃)₂ | Q²-50-1 | —NH₂ |
| 1-50-2 | 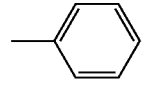 | 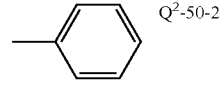 | Q²-50-2 | 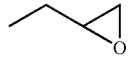 |
| 1-50-3 | 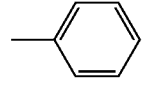 | —OCH₃ | Q²-50-3 | —OH |
| 1-50-4 | 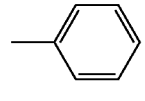 | —CH₃ | Q²-50-4 | 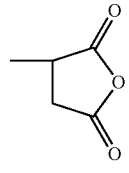 |
| 1-50-5 | 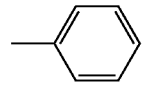 | —CH₂CH═CH₂ | Q²-50-5 | —OCOC(CH₃)═CH₂ |
| 1-51-1 | 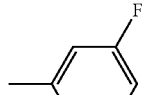 | —OCH₃ | Q²-51-1 | —COOH |
| 1-51-2 | 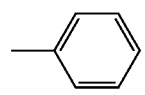 | 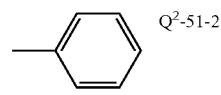 | Q²-51-2 | —NH₂ |
| 1-51-3 | 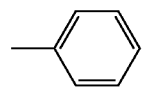 | —CH₃ | Q²-51-3 | 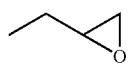 |
| 1-51-4 | 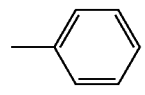 | 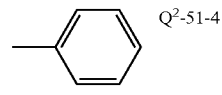 | Q²-51-4 | —NH₂ |
| 1-51-5 | 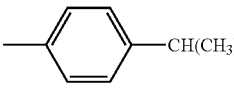 | 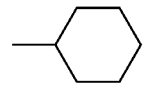 | Q²-51-5 | —COCH═CH₂ |
| 1-52-1 | 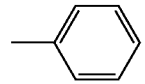 | —CH₃ | Q²-52-1 | —OH |

TABLE 19-continued

| No. | R¹ | Q¹ | Q² | Y¹ |
|---|---|---|---|---|
| 1-52-2 | 3-methylphenyl (CH₃) | —C₂H₅ | Q²-52-2 | —COOH |
| 1-52-3 | phenyl | —C₂H₅ | Q²-52-3 | 3-ethyl-3-methyloxetane |
| 1-52-4 | 3-methylphenyl (CH₃) | —C₂H₅ | Q²-52-4 | —OCOCH=CH₂ |
| 1-52-5 | 4-fluorophenyl | cyclopentyl | Q²-52-5 | —COOH |

TABLE 20

| No. | R¹ | Q¹ | Q² | Y¹ |
|---|---|---|---|---|
| 1-53-1 | 3,5-difluorophenyl | —C₂H₅ | Q²-53-1 | —NH₂ |
| 1-53-2 | phenyl | phenyl | Q²-53-2 | glycidyl (epoxide) |
| 1-53-3 | phenyl | —CH₃ | Q²-53-3 | —NH₂ |
| 1-53-4 | 4-methylphenyl | —CH(CH₃)₂ | Q²-53-4 | —OH |
| 1-53-5 | phenyl | phenyl | Q²-53-5 | glycidyl (epoxide) |
| 1-54-1 | phenyl | —CH₃ | Q²-54-1 | —COOH |
| 1-54-2 | 4-chlorophenyl | phenyl | Q²-54-2 | N-methylmaleimide |
| 1-54-3 | phenyl | phenyl | Q²-54-3 | —OH |
| 1-54-4 | phenyl | —CH₃ | Q²-54-4 | —NH₂ |
| 1-54-5 | 3-methylphenyl | —C₂H₅ | Q²-54-5 | —COCH=CH₂ |
| 1-55-1 | phenyl | cyclopentyl | Q²-55-1 | —COOH |
| 1-55-2 | phenyl | —OCH₃ | Q²-55-2 | methyl succinic anhydride |
| 1-55-3 | phenyl | cyclohexyl | Q²-55-3 | —CH=CH₂ |
| 1-55-4 | 3-methylphenyl | —C₂H₅ | Q²-55-4 | glycidyl (epoxide) |
| 1-55-5 | phenyl | —C₂H₅ | Q²-55-5 | —OH |

TABLE 21
| No. | R¹ | Q¹ | Q² | Y¹ |
|---|---|---|---|---|
| 1-56-1 | 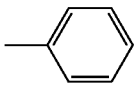 | —CH₃ | Q²-56-1 | —COOH |
| 1-56-2 | 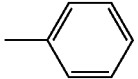 | 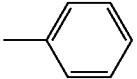 | Q²-56-2 | —OCOC(CH₃)=CH₂ |
| 1-56-3 |  | —C₂H₅ | Q²-56-3 | —OCH=CH₂ |
| 1-56-4 | 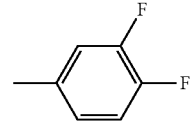 | —Cl | Q²-56-4 | —OH |
| 1-56-5 | 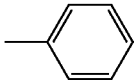 | 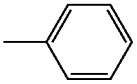 | Q²-56-5 | 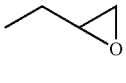 |
| 1-57-1 | 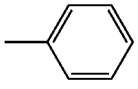 | —CH₃ | Q²-57-1 | —NH₂ |
| 1-57-2 | 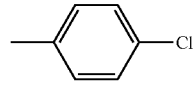 | 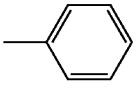 | Q²-57-2 | —COOH |
| 1-57-3 | 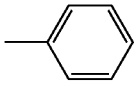 | —CH(CH₃)₂ | Q²-57-3 |  |
| 1-57-4 | 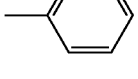 | 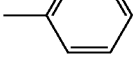 | Q²-57-4 | 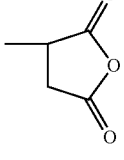 |
| 1-57-5 | 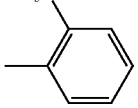 | 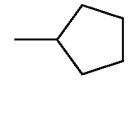 | Q²-57-5 | —OH |
| 1-58-1 | 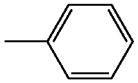 | —CH₃ | Q²-58-1 | —COOH |
| 1-58-2 | 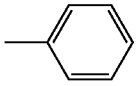 | —CH=CH₂ | Q²-58-2 | —NH₂ |
| 1-58-3 | 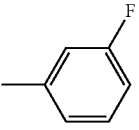 | —C₃H₇ | Q²-58-3 | —OCOCH=CH₂ |

TABLE 21-continued
| No. | R¹ | Q¹ | Q² | Y¹ |
|---|---|---|---|---|
| 1-58-4 | 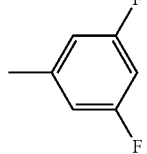 | —C$_2$H$_5$ | Q²-58-4 | 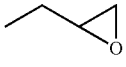 |
| 1-58-5 | 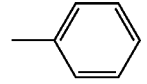 | 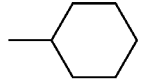 | Q²-58-5 | 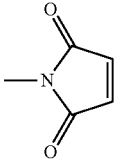 |
TABLE 22
| No. | R¹ | Q¹ | Q² | Y¹ |
|---|---|---|---|---|
| 1-59-1 | 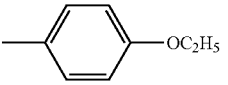 | —CH$_3$ | Q²-59-1 | —OH |
| 1-59-2 | 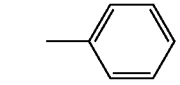 | —CH$_3$ | Q²-59-2 | 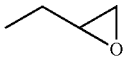 |
| 1-59-3 | 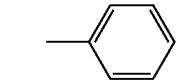 | —C$_3$H$_7$ | Q²-59-3 | —OCOCH=CH$_2$ |
| 1-59-4 | 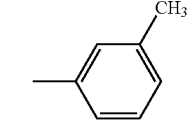 | —H | Q²-59-4 | —COOH |
| 1-59-5 | 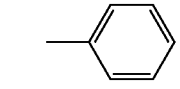 | 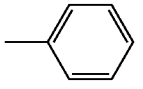 | Q²-59-5 | —OH |
| 1-60-1 | 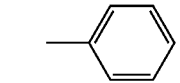 | —CH$_3$ | Q²-60-1 | —NH$_2$ |
| 1-60-2 | 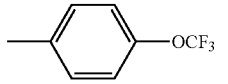 |  | Q²-60-2 | —OCH=CH$_2$ |
| 1-60-3 | 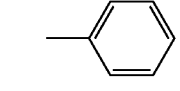 | —C$_2$H$_5$ | Q²-60-3 | 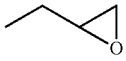 |
| 1-60-4 | 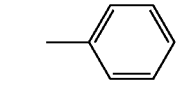 | 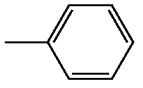 | Q²-60-4 | —NH$_2$ |
| 1-60-5 | 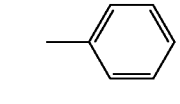 | —CH(CH$_3$)$_2$ | Q²-60-5 | 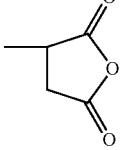 |

TABLE 22-continued

| No. | R¹ | Q¹ | Q² | Y¹ |
|---|---|---|---|---|
| 1-61-1 | phenyl | —CH₃ | Q²-61-1 | —COOH |
| 1-61-2 | 4-chlorophenyl | —C₄H₉ | Q²-61-2 | —OH |
| 1-61-3 | phenyl | cyclopentyl | Q²-61-3 | —NH₂ |
| 1-61-4 | 3-fluorophenyl | —C₂H₅ | Q²-61-4 | —CH=CH₂ |
| 1-61-5 | phenyl | —CH₃ | Q²-61-5 | glycidyl (oxiranylmethyl) |

TABLE 23

| No. | R¹ | Q¹ | Q² | Y¹ |
|---|---|---|---|---|
| 1-62-1 | phenyl | —C₂H₅ | Q²-62-1 | —OH |
| 1-62-2 | 3-fluorophenyl | —CH₃ | Q²-62-2 | —NH₂ |
| 1-62-3 | 4-methoxyphenyl | —CH₃ | Q²-62-3 | —COOH |
| 1-63-1 | phenyl | phenyl | Q²-63-1 | glycidyl (oxiranylmethyl) |
| 1-63-2 | phenyl | phenyl | Q²-63-2 | —COCH=CH₂ |
| 1-63-3 | 4-chlorophenyl | —C₃H₇ | Q²-63-3 | glycidyl (oxiranylmethyl) |
| 1-64-1 | phenyl | 3-methylphenyl | Q²-64-1 | maleimido (N-) |
| 1-64-2 | phenyl | —CH(CH₃)₂ | Q²-64-2 | —OCOCH=CH₂ |

TABLE 23-continued

| No. | R¹ | Q¹ | Q² | Y¹ |
|---|---|---|---|---|
| 1-64-3 | phenyl | phenyl | Q²-64-3 | —COOH |
| 1-65-1 | phenyl | —CH(CH₃)₂ | Q²-65-1 | methyl-substituted succinic anhydride |
| 1-65-2 | 4-methylphenyl | cyclohexyl | Q²-65-2 | —NH₂ |
| 1-65-3 | phenyl | cyclopentyl | Q²-65-3 | —COOH |
| 1-66-1 | phenyl | —CH₃ | Q²-66-1 | —NH₂ |
| 1-66-2 | 3-fluorophenyl | —CH₃ | Q²-66-2 | —OH |
| 1-66-3 | phenyl | cyclopentyl | Q²-66-3 | N-methylmaleimide |

TABLE 24

| No. | R¹ | Q¹ | Q² | Y¹ |
|---|---|---|---|---|
| 1-67-1 | phenyl | phenyl | Q²-67-1 | —OH |
| 1-67-2 | phenyl | —CH=CH₂ | Q²-67-2 | N-maleimide |
| 1-67-3 | 3,4-difluorophenyl | —CH₃ | Q²-67-3 | —COOH |

TABLE 24-continued
| No. | R¹ | Q¹ | Q² | Y¹ |
|---|---|---|---|---|
| 1-68-1 | 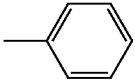 | 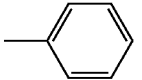 | Q²-68-1 | —OCOC(CF₃)═CH₂ |
| 1-68-2 | 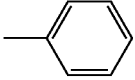 | —C₃H₇ | Q²-68-2 | —Br |
| 1-68-3 | 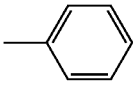 | —C₃H₇ | Q²-68-3 | —COOH |
| 1-69-1 | 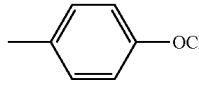 | 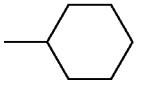 | Q²-69-1 | —OH |
| 1-69-2 | 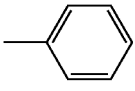 | —C₂H₅ | Q²-69-2 | 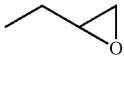 |
| 1-69-3 | 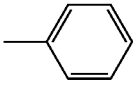 | 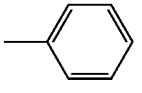 | Q²-69-3 | —CH═CH₂ |
| 1-70-1 | 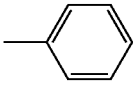 | —CH₃ | Q²-70-1 | —COOH |
| 1-70-2 | 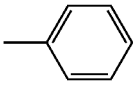 | 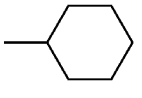 | Q²-70-2 | 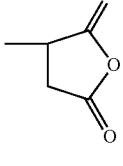 |
| 1-70-3 | 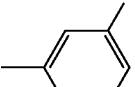 | —OCH₃ | Q²-70-3 | —COCl |
| 1-71-1 | 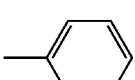 | 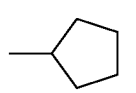 | Q²-71-1 | —NH₂ |
| 1-71-2 | 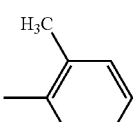 | —CH₃ | Q²-71-2 | —OH |
| 1-71-3 | 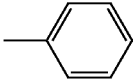 | —CH(CH₃)₂ | Q²-71-3 | —OCH═CH₂ |

TABLE 25

| No. | R¹ | Q¹ | Q² | Y¹ |
|---|---|---|---|---|
| 1-72-1 | phenyl | cyclopentyl | Q²-72-1 | —COOH |
| 1-72-2 | phenyl | —CH₃ | Q²-72-2 | —OH |
| 1-72-3 | 3-methylphenyl | —CH₃ | Q²-72-3 | —OCH=CH₂ |
| 1-73-1 | phenyl | phenyl | Q²-73-1 | —NH₂ |
| 1-73-2 | phenyl | —CH₃ | Q²-73-2 | —OH |
| 1-73-3 | phenyl | cyclohexyl | Q²-73-3 | succinic anhydride |
| 1-74-1 | phenyl | —C₂H₅ | Q²-74-1 | —OH |
| 1-74-2 | 3,4-difluorophenyl | —CH(CH₃)₂ | Q²-74-2 | —COOH |
| 1-74-3 | phenyl | phenyl | Q²-74-3 | succinic anhydride |
| 1-75-1 | phenyl | —CH₃ | Q²-75-1 | epoxide (glycidyl) |
| 1-75-2 | phenyl | —OCH₃ | Q²-75-2 | —COOH |
| 1-75-3 | 3-fluorophenyl | —C₃H₇ | Q²-75-3 | —OH |
| 1-76-1 | phenyl | —CH(CH₃)₂ | Q²-76-1 | —OH |
| 1-76-2 | phenyl | —CH₃ | Q²-76-2 | —OCOCH=CH₂ |
| 1-76-3 | phenyl | —OCH₃ | Q²-76-3 | epoxide (glycidyl) |

TABLE 26

| No. | R¹ | Q¹ | Q² | Y¹ |
|---|---|---|---|---|
| 1-77-1 | phenyl | cyclohexyl | Q²-77-1 | —COOH |
| 1-77-2 | phenyl | —CH₃ | Q²-77-2 | —OH |
| 1-77-3 | phenyl | —CH₃ | Q²-77-3 | —CH=CH₂ |
| 1-78-1 | phenyl | phenyl | Q²-78-1 | —OH |
| 1-78-2 | 4-chlorophenyl | —C₃H₇ | Q²-78-2 | —OCH=CH₂ |
| 1-78-3 | 4-fluorophenyl | cyclopentyl | Q²-78-3 | succinic anhydride |
| 1-79-1 | phenyl | —C₄H₉ | Q²-79-1 | —OH |
| 1-79-2 | 3-fluorophenyl | —CH₃ | Q²-79-2 | —NH₂ |
| 1-79-3 | phenyl | phenyl | Q²-79-3 | —COOH |
| 1-80-1 | phenyl | —CH₃ | Q²-80-1 | —NH₂ |
| 1-80-2 | phenyl | —C₂H₅ | Q²-80-2 | —CN |

TABLE 26-continued

| No. | R¹ | Q¹ | Q² | Y¹ |
|---|---|---|---|---|
| 1-80-3 | 3-fluorophenyl | —CH₃ | Q²-80-3 | —COOH |
| 1-81-1 | phenyl | cyclopentyl | Q²-81-1 | —OH |
| 1-81-2 | phenyl | —OCH₃ | Q²-81-2 | glycidyl (epoxide) |
| 1-81-3 | phenyl | phenyl | Q²-81-3 | glycidyl (epoxide) |

TABLE 27

| No. | R¹ | Q¹ | Q² | Y¹ |
|---|---|---|---|---|
| 1-82-1 | 3,5-difluorophenyl | —OCH₃ | Q²-82-1 | —COOH |
| 1-82-2 | phenyl | —CH₃ | Q²-82-2 | —OH |
| 1-82-3 | phenyl | phenyl | Q²-82-3 | —NH₂ |
| 1-83-1 | phenyl | phenyl | Q²-83-1 | —CH=CH₂ |
| 1-83-2 | phenyl | —CH(CH₃)₂ | Q²-83-2 | —NH₂ |
| 1-84-1 | 4-fluorophenyl | —C₂H₅ | Q²-84-1 | —OH |
| 1-84-2 | phenyl | —CH₃ | Q²-84-2 | 3-ethyl-3-oxetanyl |

TABLE 27-continued

| No. | R¹ | Q¹ | Q² | Y¹ |
|---|---|---|---|---|
| 1-85-1 | phenyl | phenyl | Q²-85-1 | —COCl |
| 1-85-2 | phenyl | phenyl | Q²-85-2 | glycidyl (epoxide) |
| 1-86-1 | phenyl | —CH₃ | Q²-86-1 | —OH |
| 1-86-2 | phenyl | —CH₃ | Q²-86-2 | —COOH |
| 1-86-3 | 3,4-difluorophenyl | 3-fluorophenyl | Q²-86-3 | —OH |
| 1-87-1 | phenyl | cyclohexyl | Q²-87-1 | —CHO |
| 1-87-2 | phenyl | —OCH₃ | Q²-87-2 | 3-methyl-dihydrofuran-2,5-dione |

TABLE 28

| No. | R¹ | Q¹ | Q² | Y¹ |
|---|---|---|---|---|
| 1-88-1 | 4-chlorophenyl | cyclopentyl | Q²-88-1 | —COOH |
| 1-88-2 | phenyl | —CH(CH₃)₂ | Q²-88-2 | 3-methyl-dihydrofuran-2,5-dione |
| 1-89-1 | phenyl | phenyl | Q²-89-1 | —OH |
| 1-89-2 | 4-methoxyphenyl | phenyl | Q²-89-2 | —NH₂ |

In the tables described above, Q²-1-1 to Q²-89-2 described in the column of Q² have meanings shown in the following Formula (Q²-1-1) to Formula (Q²-89-2). A code "<" shown at a left end in these formulas shows a bonding point to an Si atom.

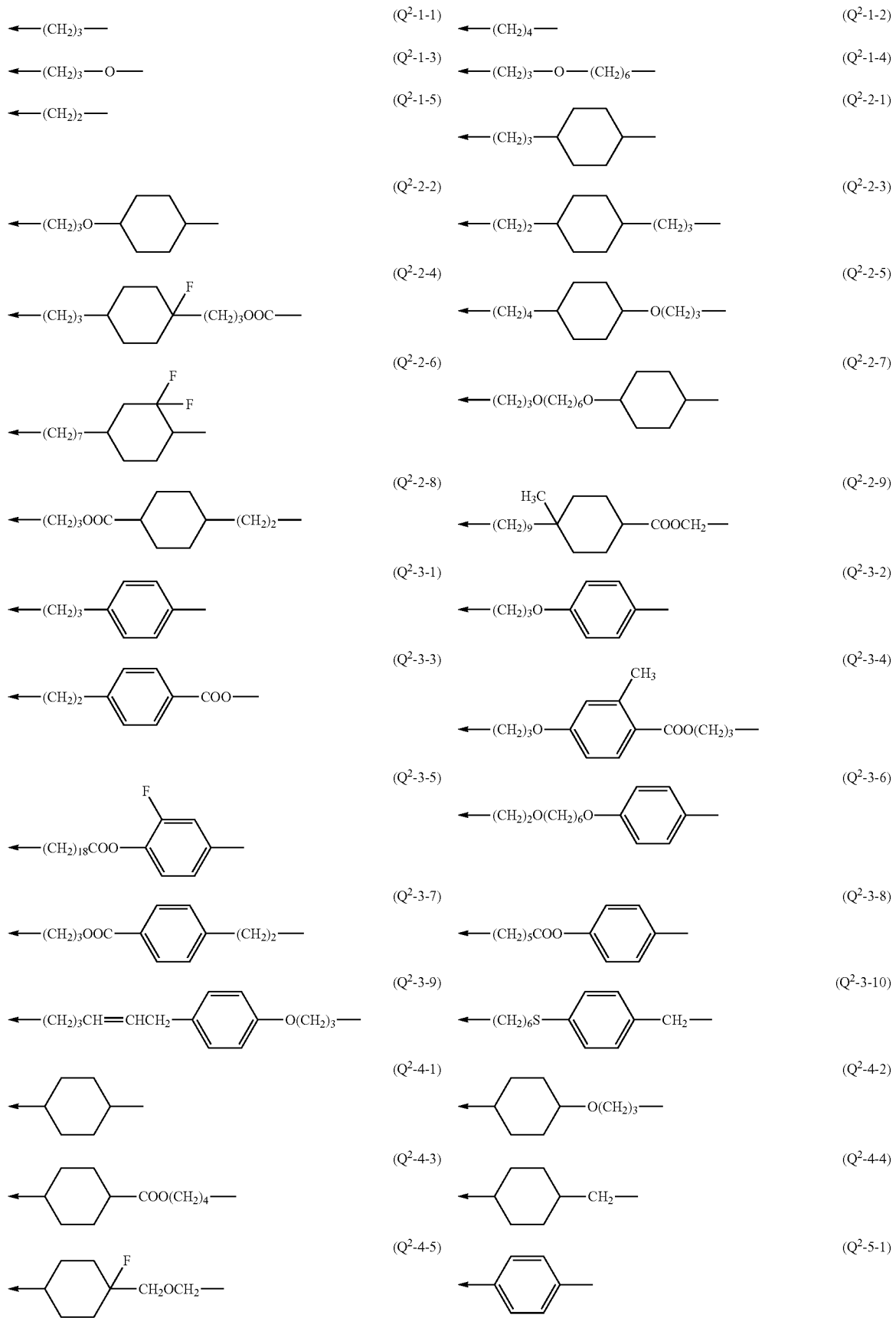

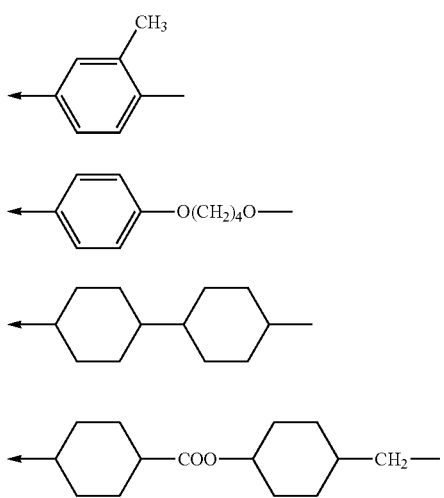
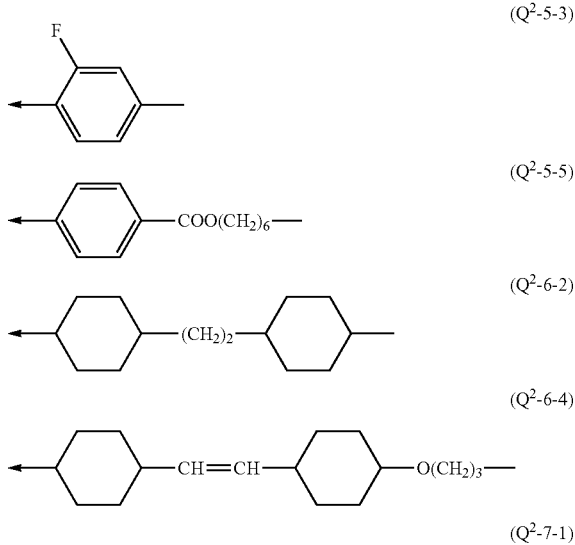
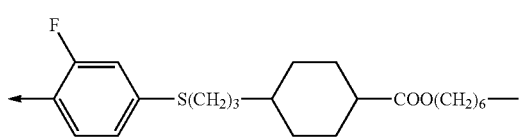

-continued
(Q²-10-1) 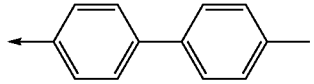
(Q²-10-2) 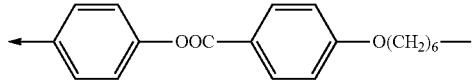
(Q²-10-3) 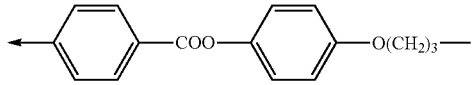
(Q²-10-4) 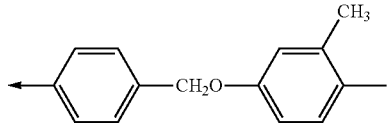
(Q²-10-5) 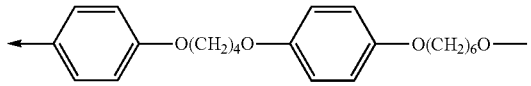
(Q²-11-1) 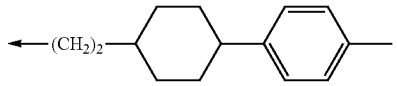
(Q²-11-2) 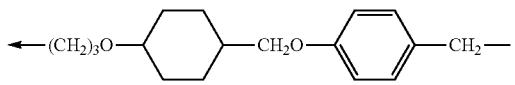
(Q²-11-3) 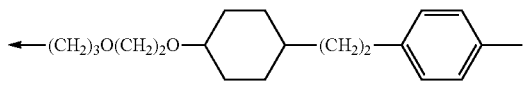
(Q²-11-4) 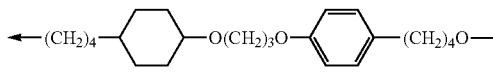
(Q²-11-5) 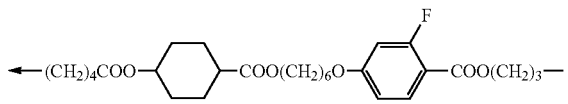
(Q²-12-1) 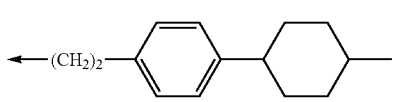
(Q²-12-2) 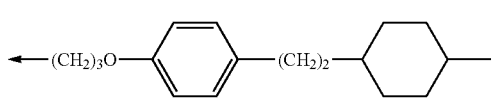
(Q²-12-3) 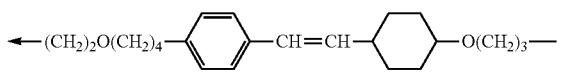
(Q²-12-4) 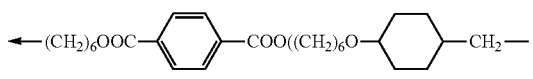
(Q²-12-5) 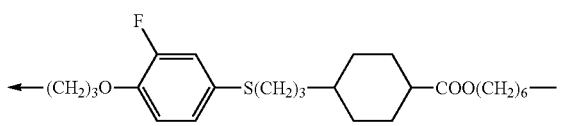
(Q²-13-1) 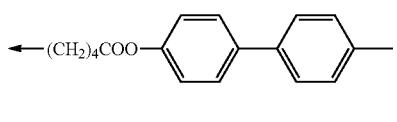
(Q²-13-2) 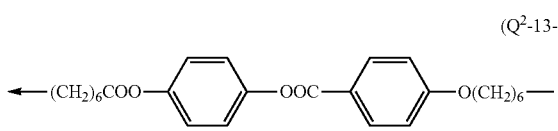
(Q²-13-3) 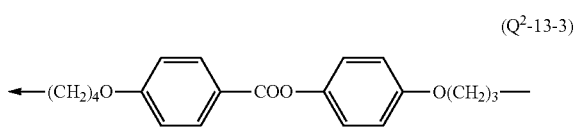
(Q²-13-4) 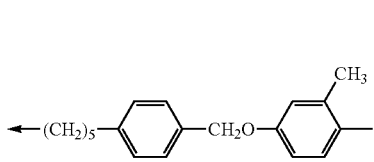
(Q²-13-5) 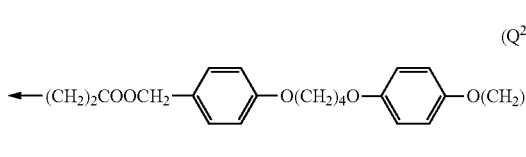
(Q²-14-1) 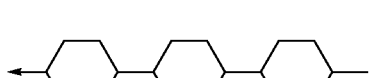
(Q²-14-2) 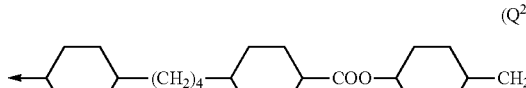
(Q²-14-3) 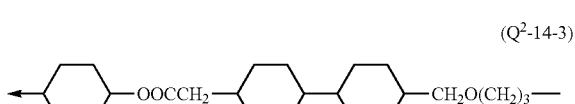
(Q²-14-4) 

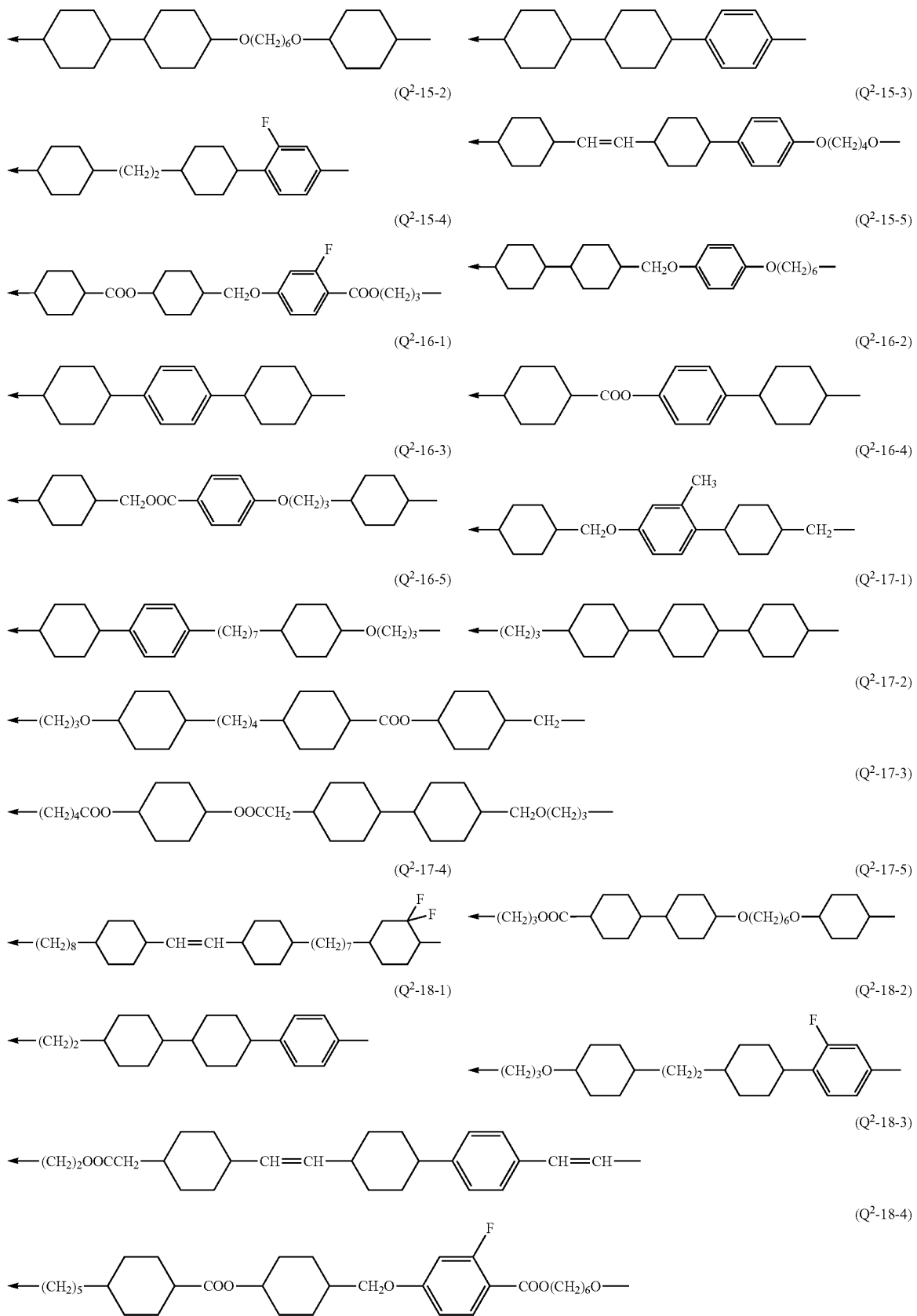

-continued
(Q2-18-5)
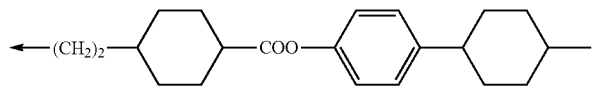
(Q²-19-1)
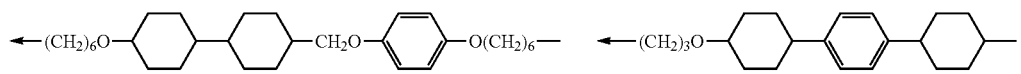
(Q²-19-2)
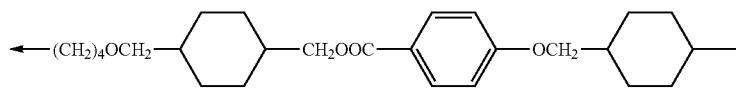
(Q²-19-3)
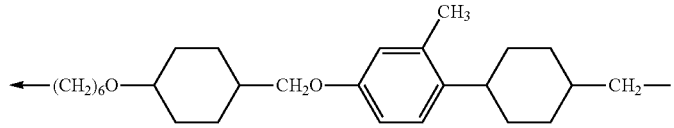
(Q²-19-4)
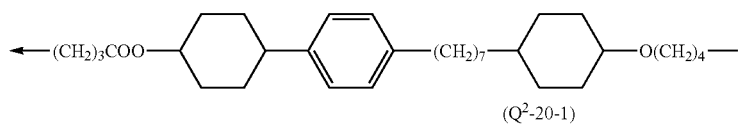
(Q²-19-5)
(Q²-20-1)
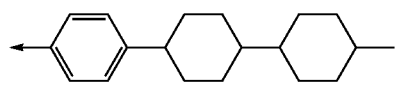
(Q²-20-2)
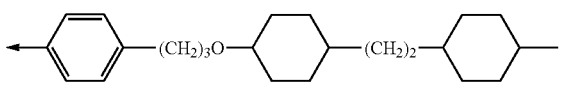
(Q²-20-3)
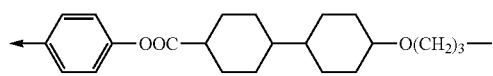
(Q²-20-4)
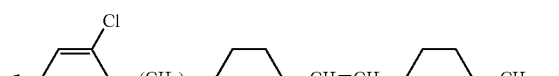
(Q²-20-5)
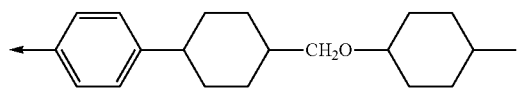
(Q²-21-1)
(Q²-21-2)
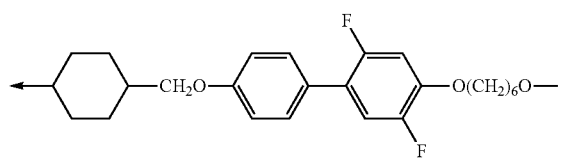
(Q²-21-3)
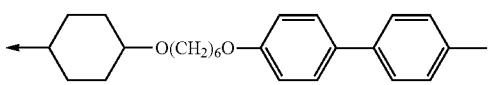
(Q²-21-4)
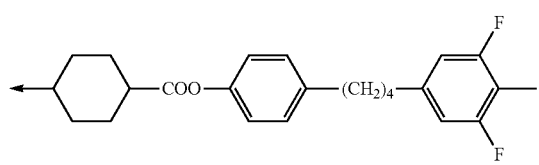
(Q²-21-5)
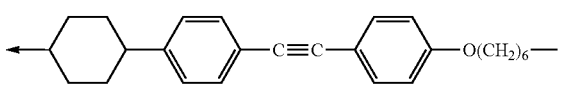
(Q²-22-1)
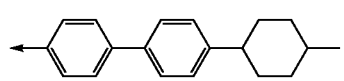
(Q²-22-2)
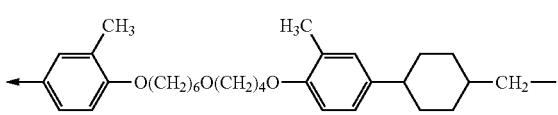
(Q²-22-3)
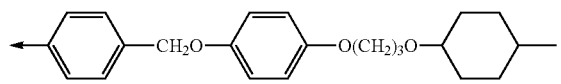
(Q²-22-4)
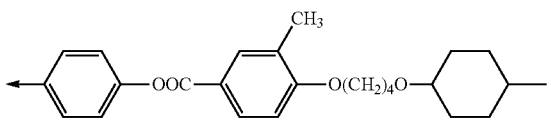

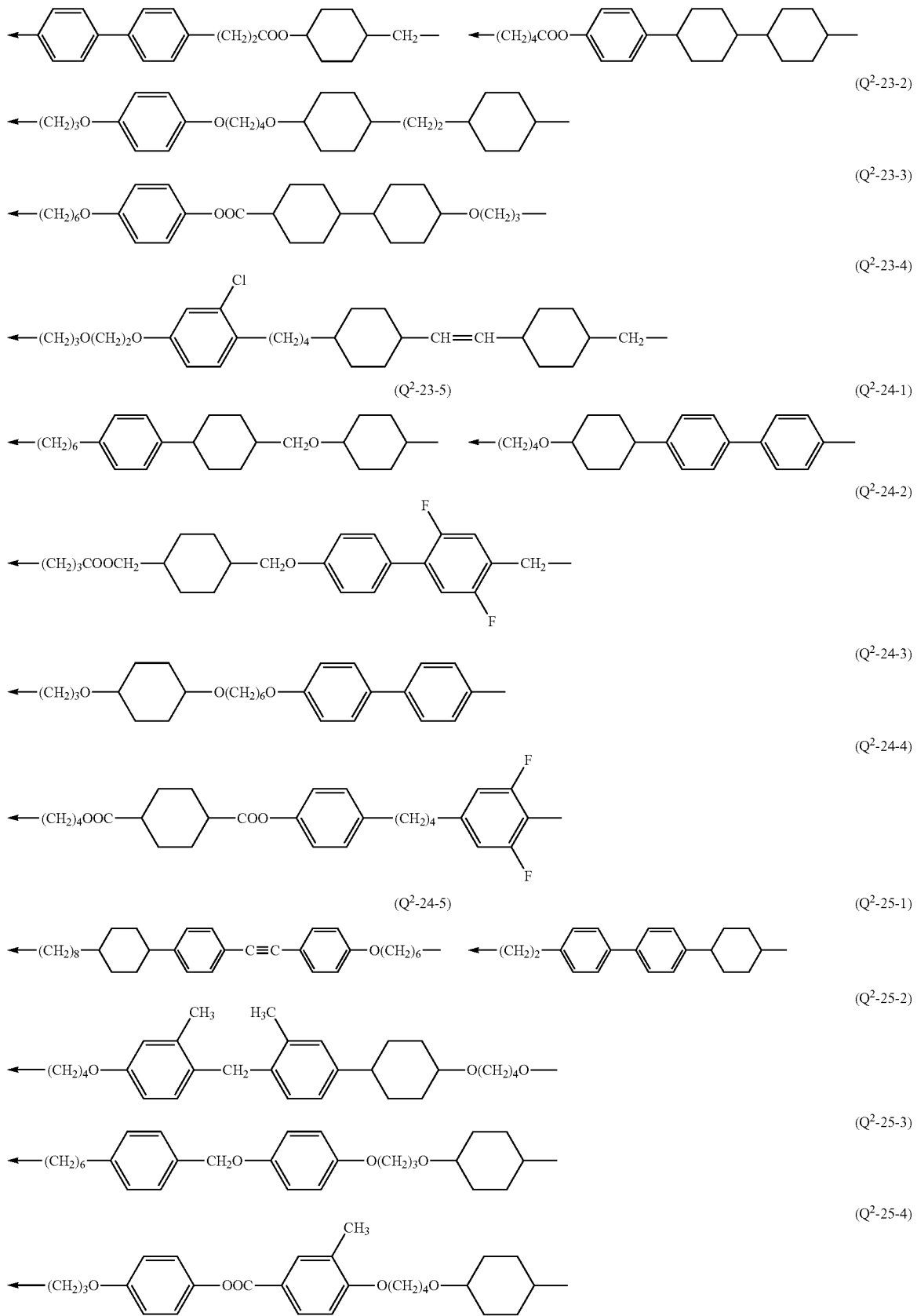

-continued

-continued
(Q²-29-2)
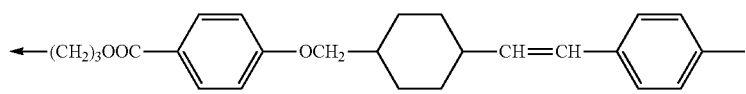
(Q²-29-3)
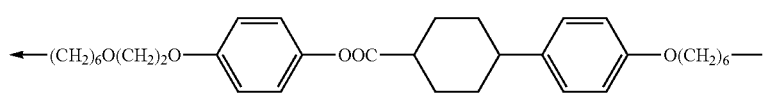
(Q²-29-4)
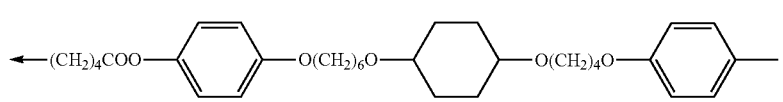
(Q²-29-5)
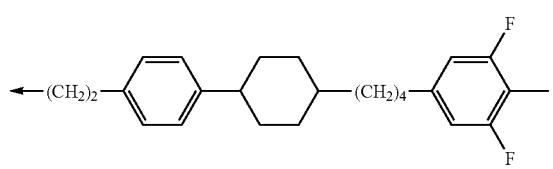
(Q²-30-1)
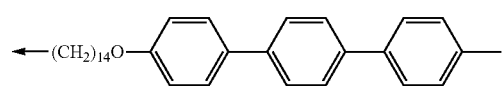
(Q²-30-2)
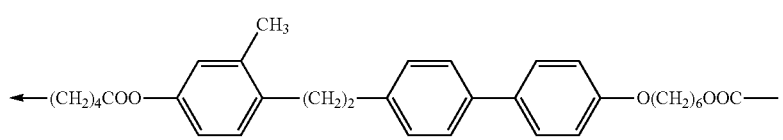
(Q²-30-3)
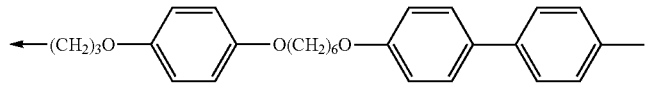
(Q²-30-4)
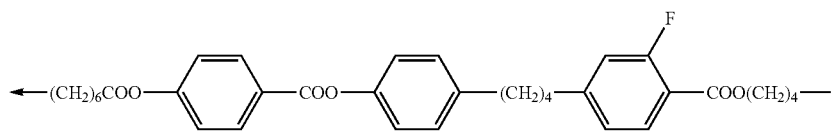
(Q²-30-5)
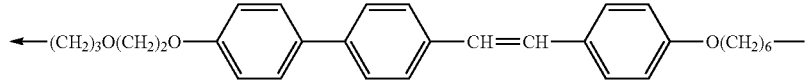
(Q²-31-1)
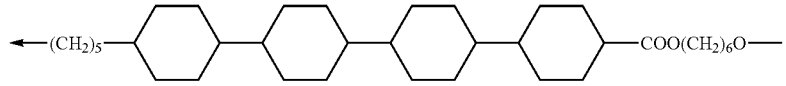
(Q²-31-2)
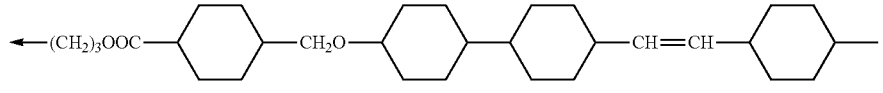
(Q²-31-3)
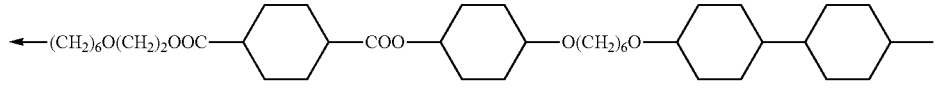
(Q²-31-4)
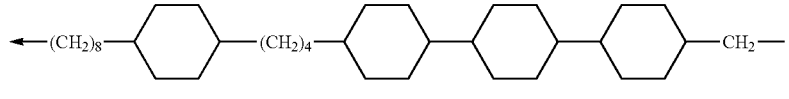
(Q²-31-5)
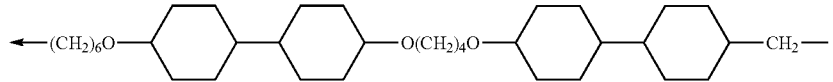

-continued
(Q²-32-1)
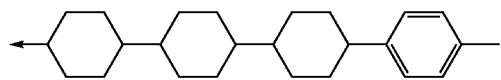
(Q²-32-2)
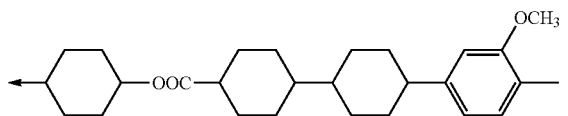
(Q²-32-3)
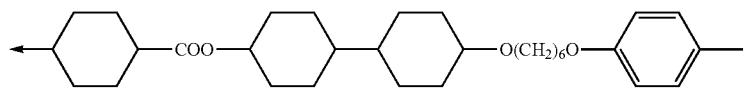
(Q²-32-4)
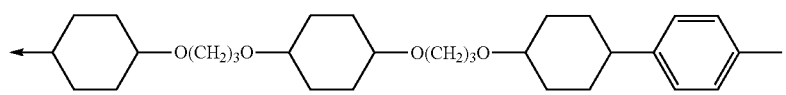
(Q²-32-5)
(Q²-33-1)
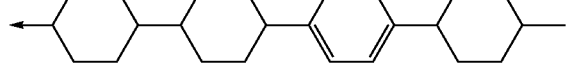
(Q²-33-2)
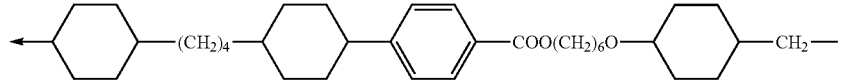
(Q²-33-3)
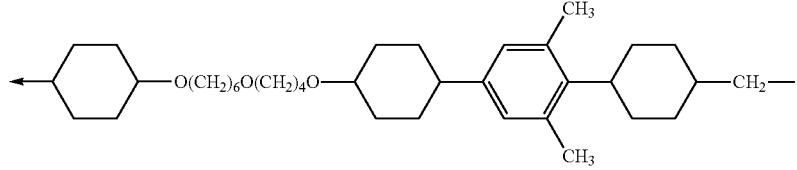
(Q²-33-4)
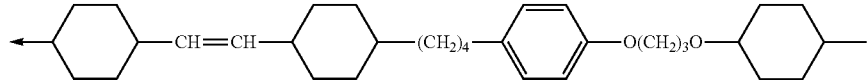
(Q²-33-5)
(Q²-34-1)
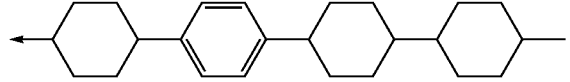
(Q²-34-2)
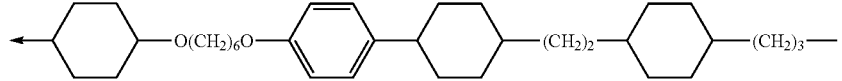
(Q²-34-3)
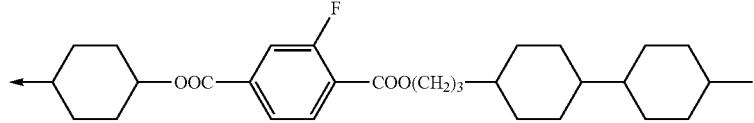
(Q²-34-4)
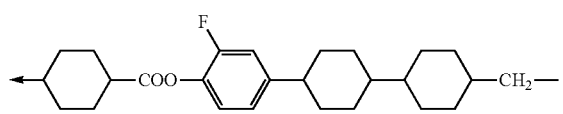
(Q²-34-5)
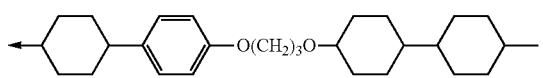

-continued
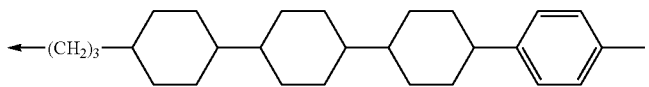
(Q²-35-1)
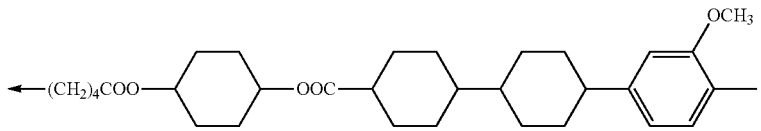
(Q²-35-2)
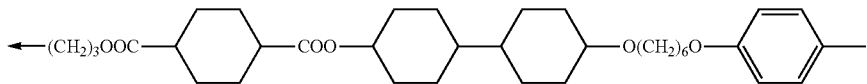
(Q²-35-3)
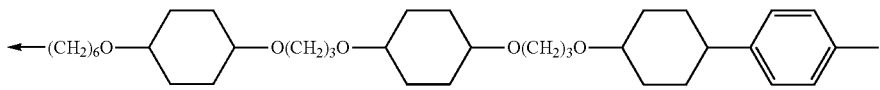
(Q²-35-4)
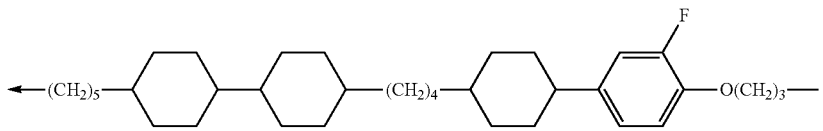
(Q²-35-5)
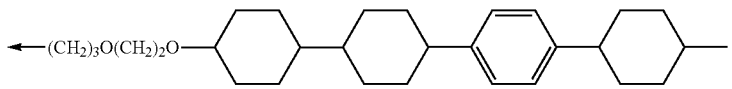
(Q²-36-1)
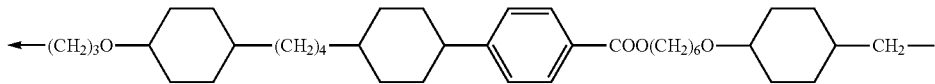
(Q²-36-2)
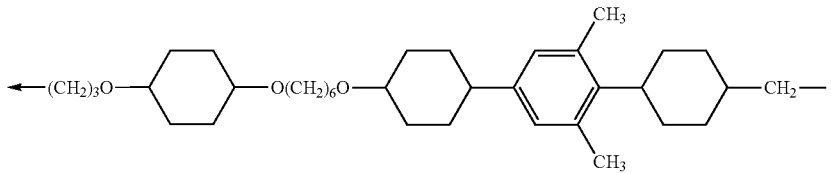
(Q²-36-3)
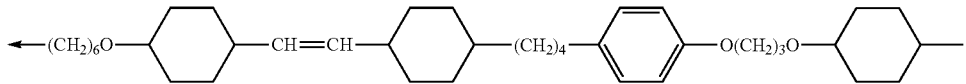
(Q²-36-4)
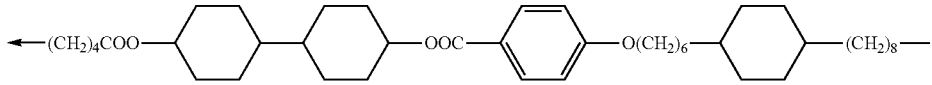
(Q²-36-5)
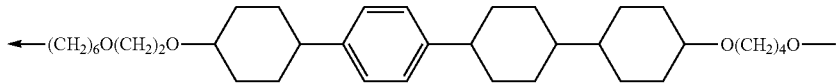
(Q²-37-1)
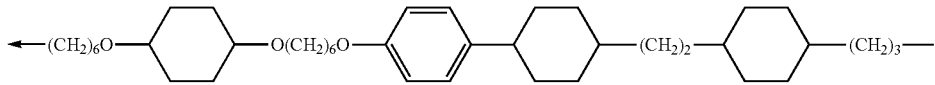
(Q²-37-2)
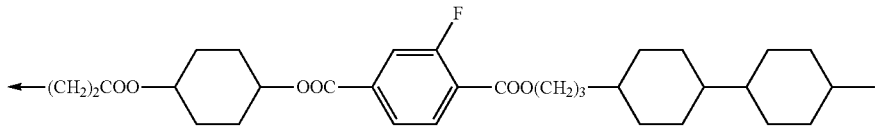
(Q²-37-3)

-continued
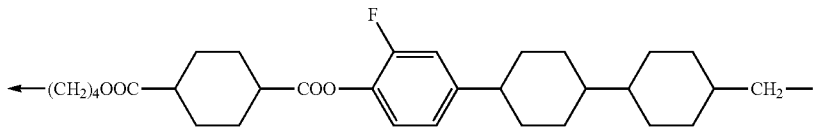
(Q²-37-4)
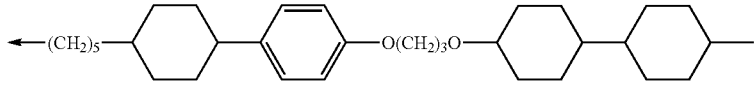
(Q²-37-5)
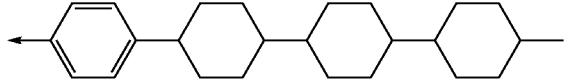
(Q²-38-1)
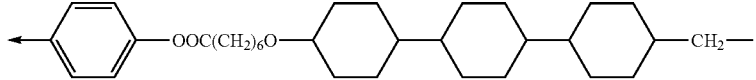
(Q²-38-2)
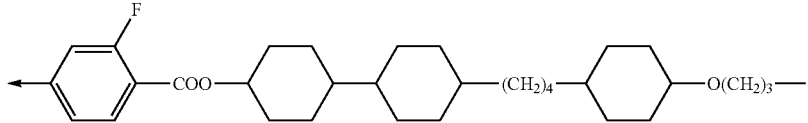
(Q²-38-3)
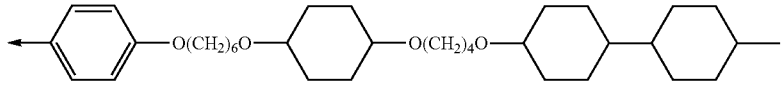
(Q²-38-4)
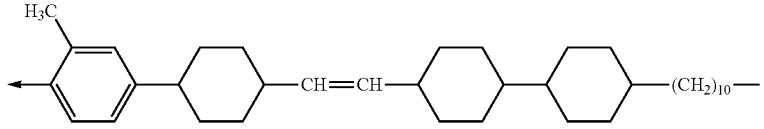
(Q²-38-5)
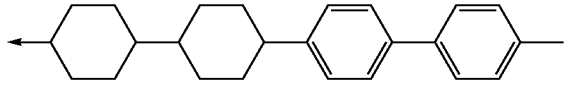
(Q²-39-1)
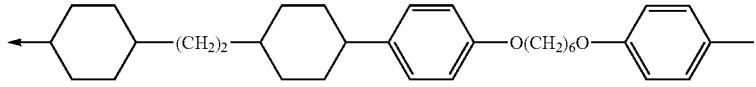
(Q²-39-2)
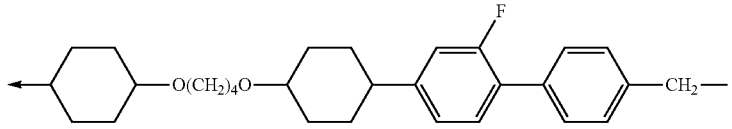
(Q²-39-3)
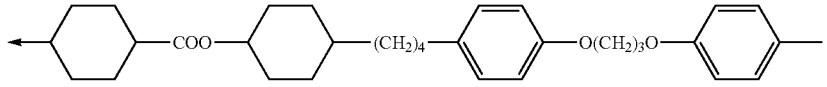
(Q²-39-4)
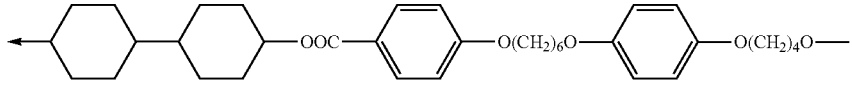
(Q²-39-5)
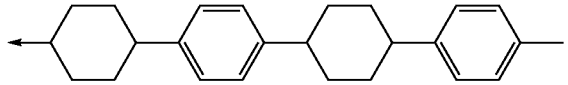
(Q²-40-1)

-continued
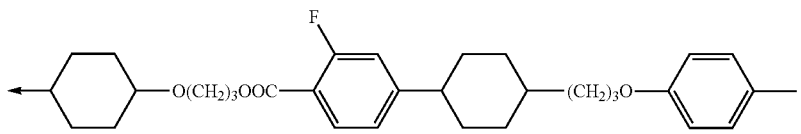
(Q²-40-2)
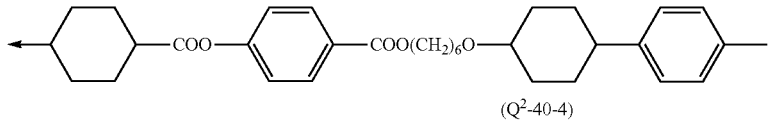
(Q²-40-3)
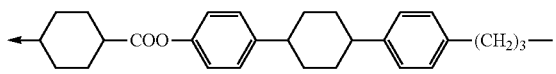
(Q²-40-4)
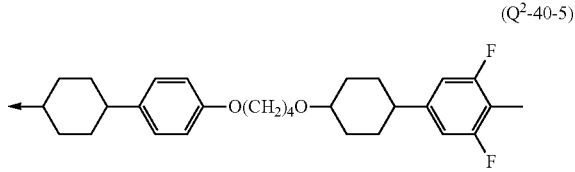
(Q²-40-5)
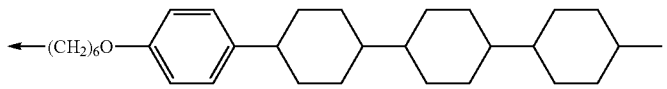
(Q²-41-1)
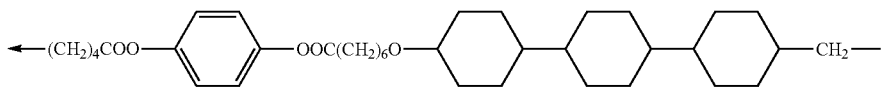
(Q²-41-2)
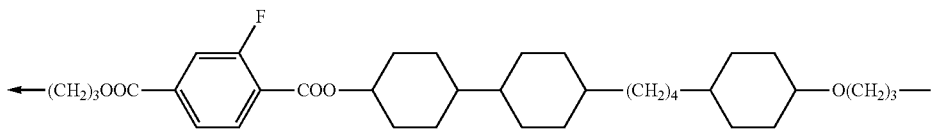
(Q²-41-3)
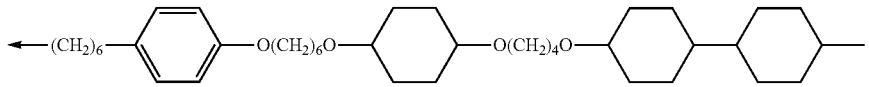
(Q²-41-4)
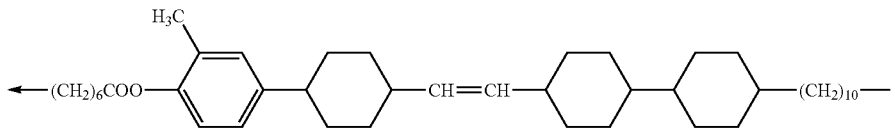
(Q²-41-5)
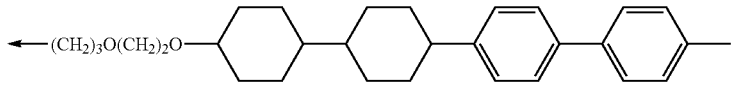
(Q²-42-1)
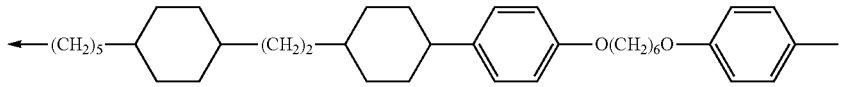
(Q²-42-2)
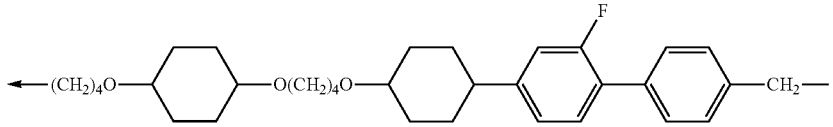
(Q²-42-3)
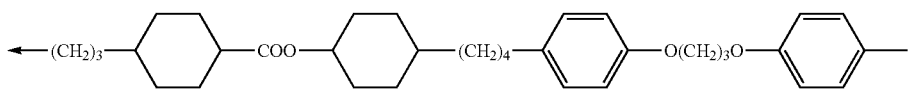
(Q²-42-4)
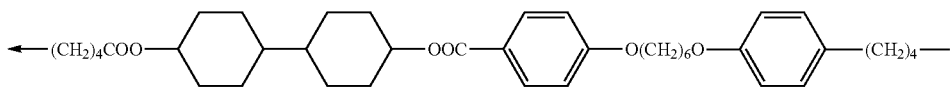
(Q²-42-5)

-continued
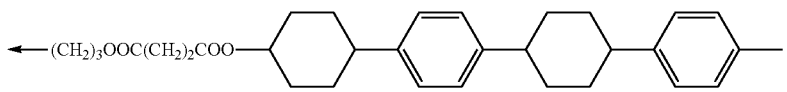
(Q²-43-1)
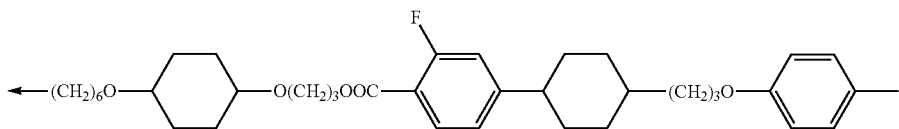
(Q²-43-2)
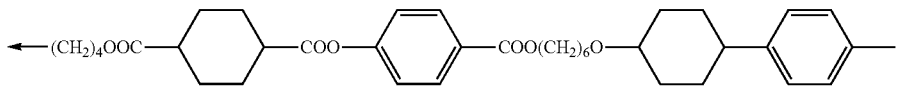
(Q²-43-3)
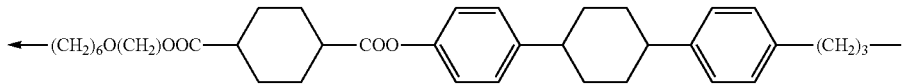
(Q²-43-4)
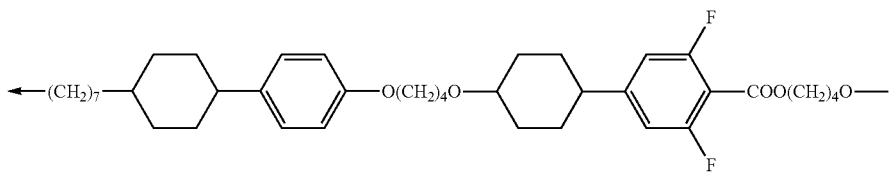
(Q²-43-5)
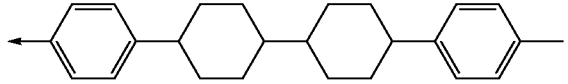
(Q²-44-1)
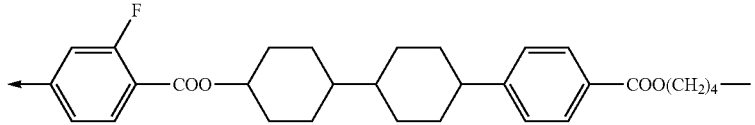
(Q²-44-2)
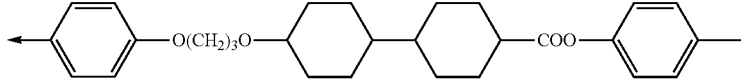
(Q²-44-3)
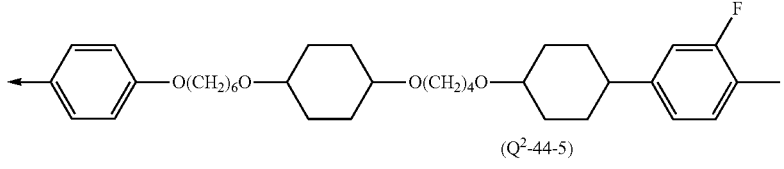
(Q²-44-4)
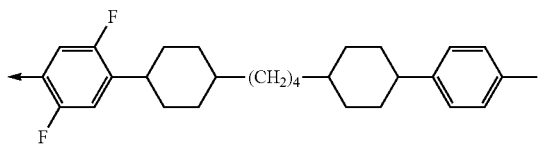
(Q²-44-5)
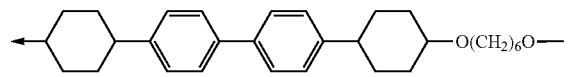
(Q²-45-1)
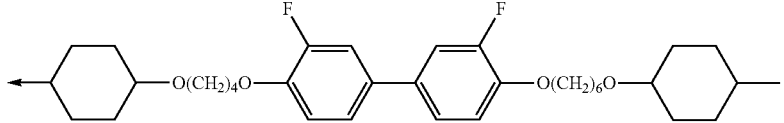
(Q²-45-2)
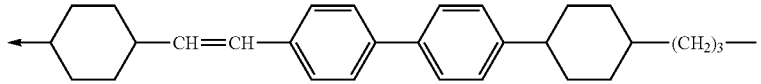
(Q²-45-3)

-continued
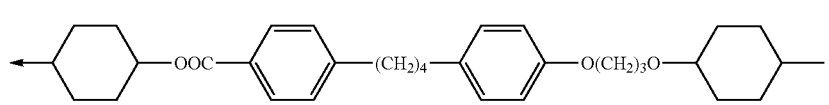
(Q²-45-4)
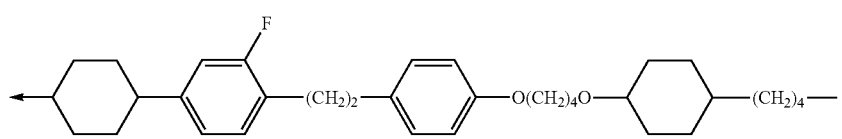
(Q²-45-5)
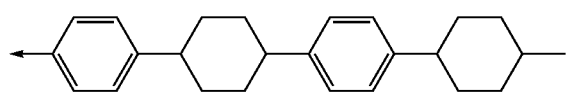
(Q²-46-1)
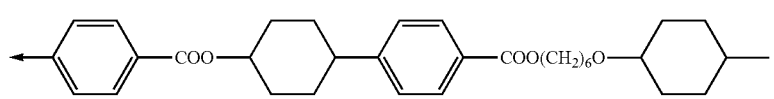
(Q²-46-2)
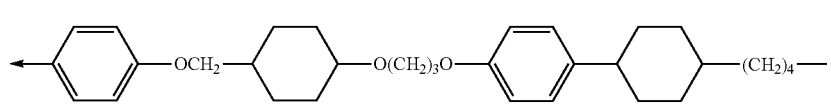
(Q²-46-3)
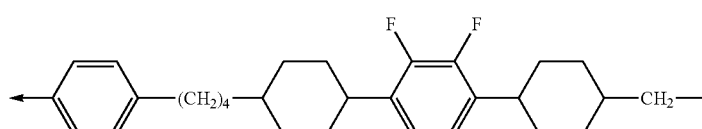
(Q²-46-4)
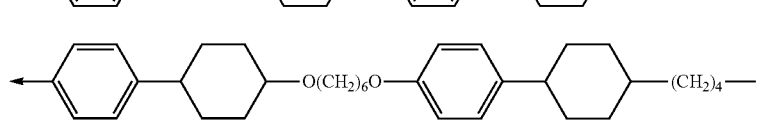
(Q²-46-5)
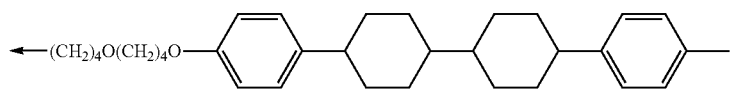
(Q²-47-1)
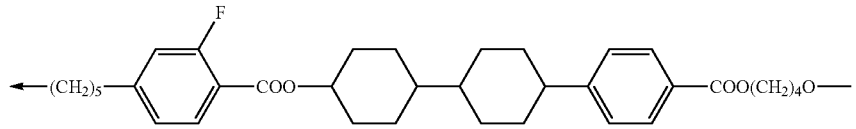
(Q²-47-2)
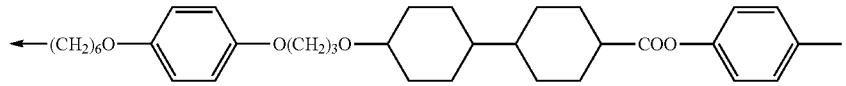
(Q²-47-3)
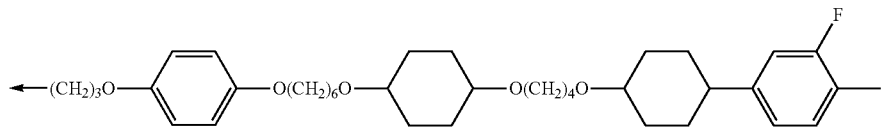
(Q²-47-4)
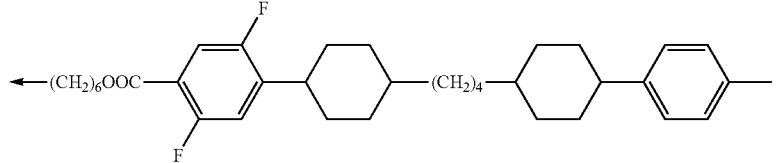
(Q²-47-5)
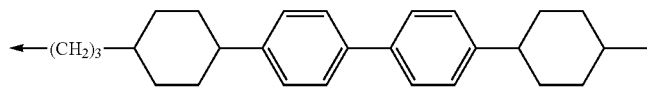
(Q²-48-1)

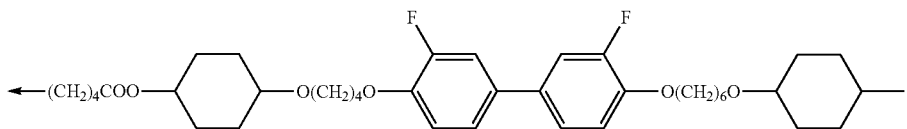
(Q²-48-2)
(Q²-48-3)
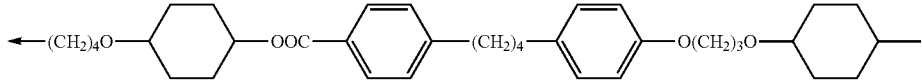
(Q²-48-4)
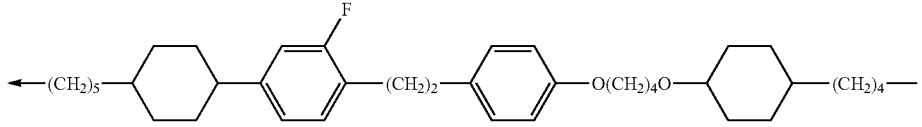
(Q²-48-5)
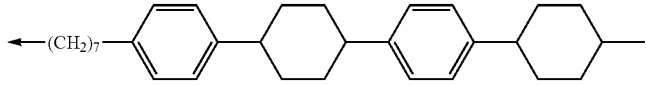
(Q²-49-1)
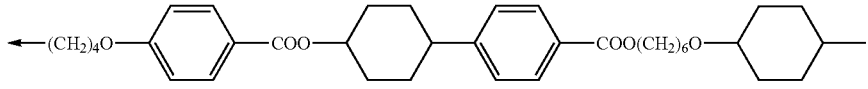
(Q²-49-2)
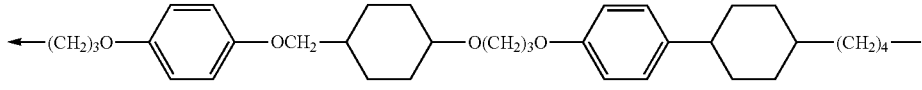
(Q²-49-3)
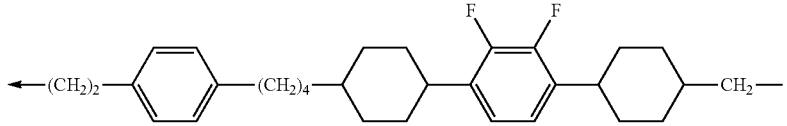
(Q²-49-4)
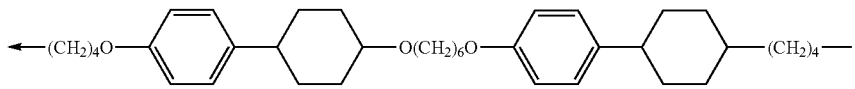
(Q²-49-5)
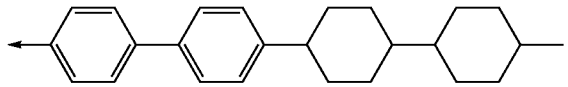
(Q²-50-1)
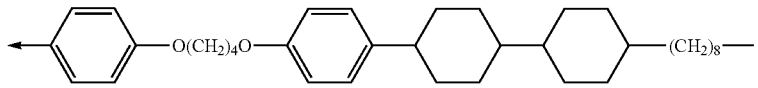
(Q²-50-2)
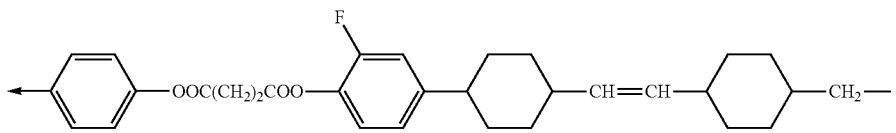
(Q²-50-3)
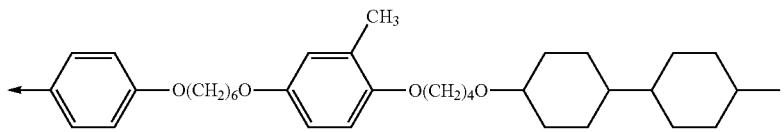
(Q²-50-4)

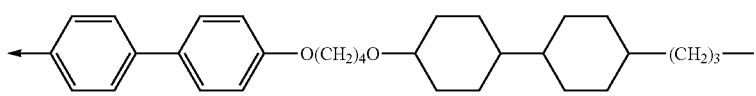
(Q²-50-5)
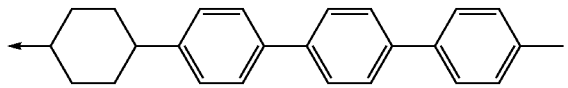
(Q²-51-1)
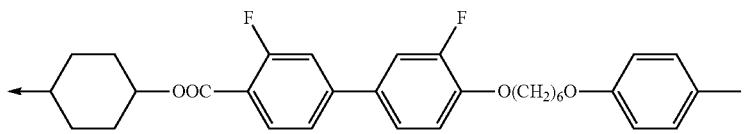
(Q²-51-2)
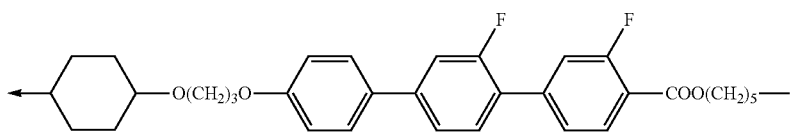
(Q²-51-3)
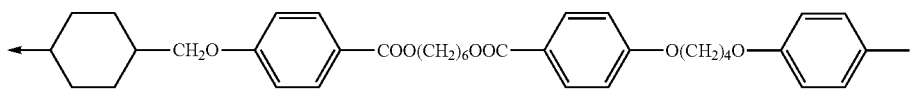
(Q²-51-4)
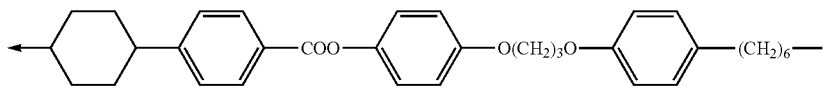
(Q²-51-5)
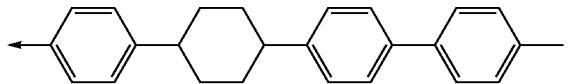
(Q²-52-1)
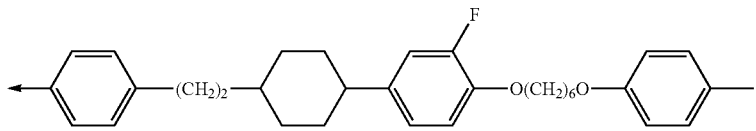
(Q²-52-2)
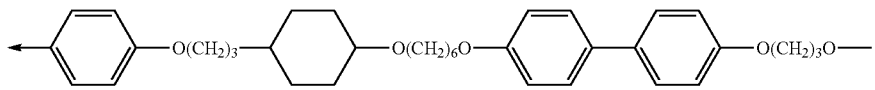
(Q²-52-3)
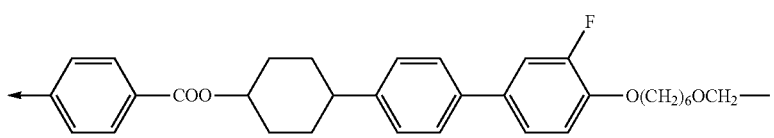
(Q²-52-4)
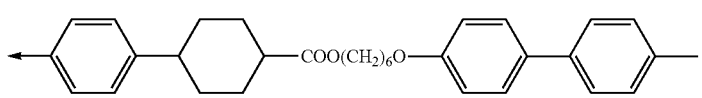
(Q²-52-5)
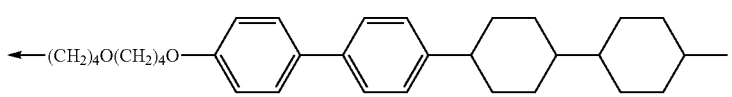
(Q²-53-1)
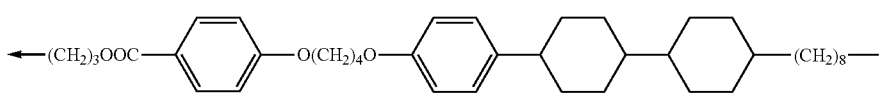
(Q²-53-2)

-continued
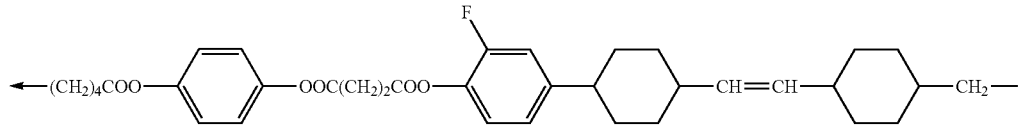
(Q²-53-3)
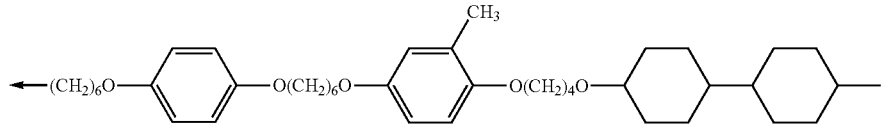
(Q²-53-4)
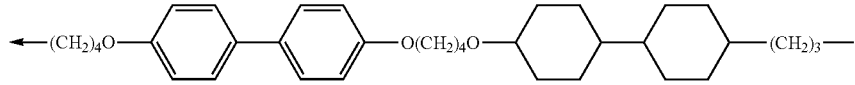
(Q²-53-5)
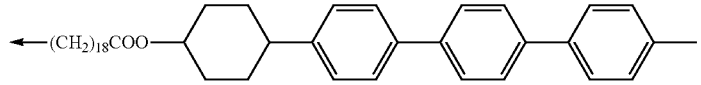
(Q²-54-1)
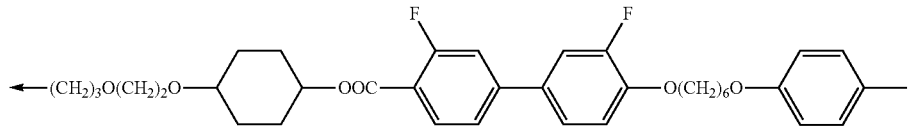
(Q²-54-2)
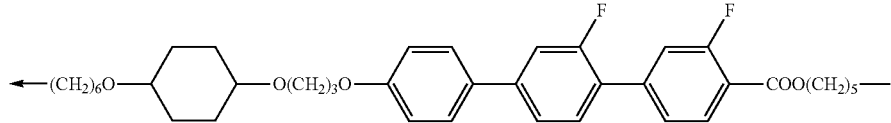
(Q²-54-3)
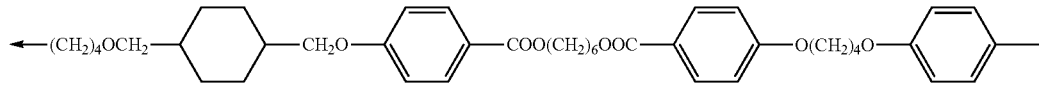
(Q²-54-4)
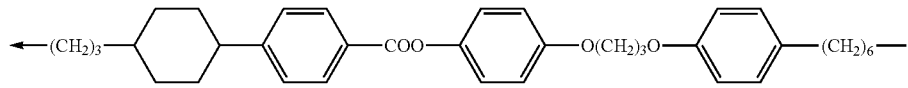
(Q²-54-5)
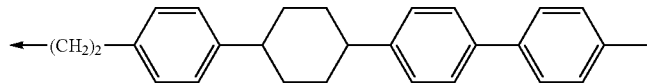
(Q²-55-1)
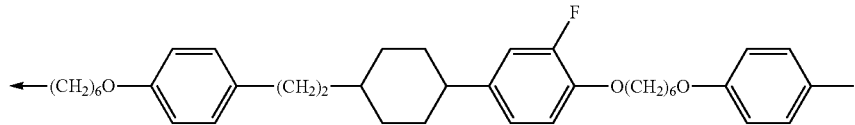
(Q²-55-2)
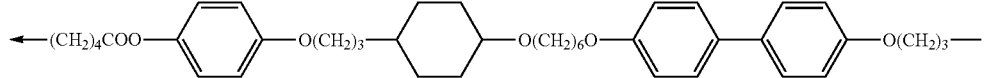
(Q²-55-3)
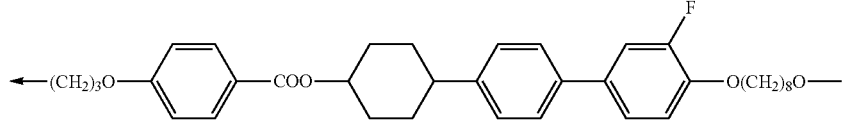
(Q²-55-4)
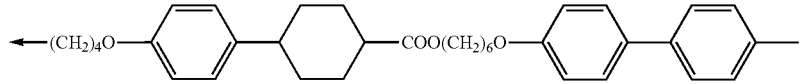
(Q²-55-5)

-continued
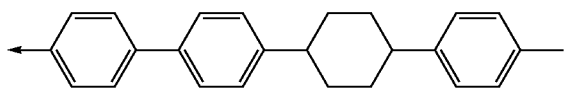
(Q²-56-1)
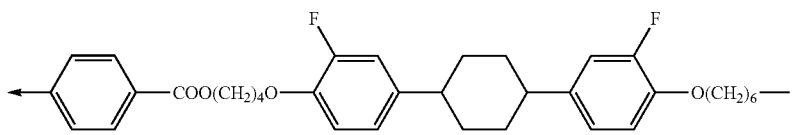
(Q²-56-2)
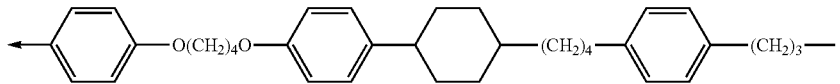
(Q²-56-3)
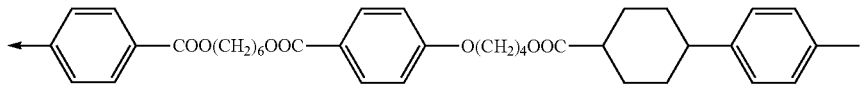
(Q²-56-4)
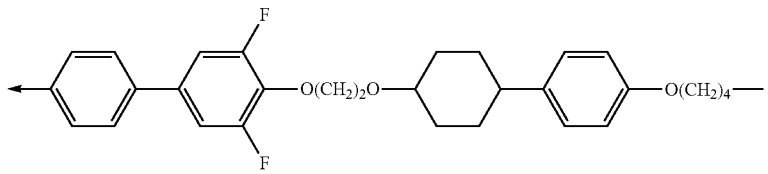
(Q²-56-5)
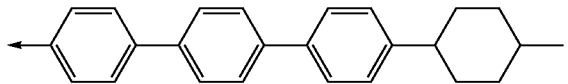
(Q²-57-1)
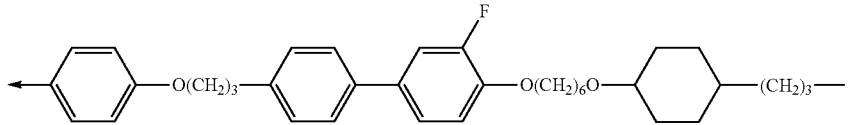
(Q²-57-2)
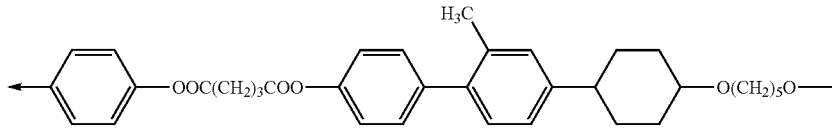
(Q²-57-3)
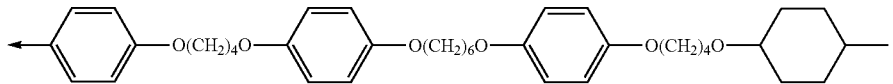
(Q²-57-4)
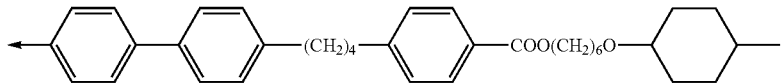
(Q²-57-5)
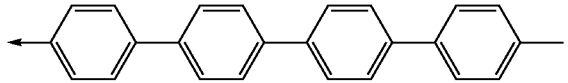
(Q²-58-1)
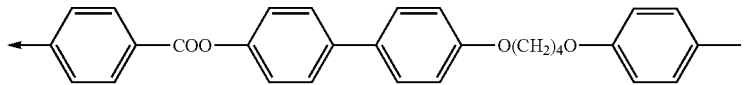
(Q²-58-2)
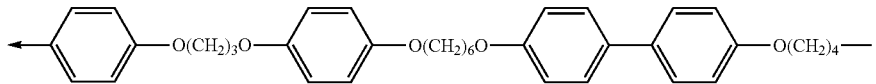
(Q²-58-3)

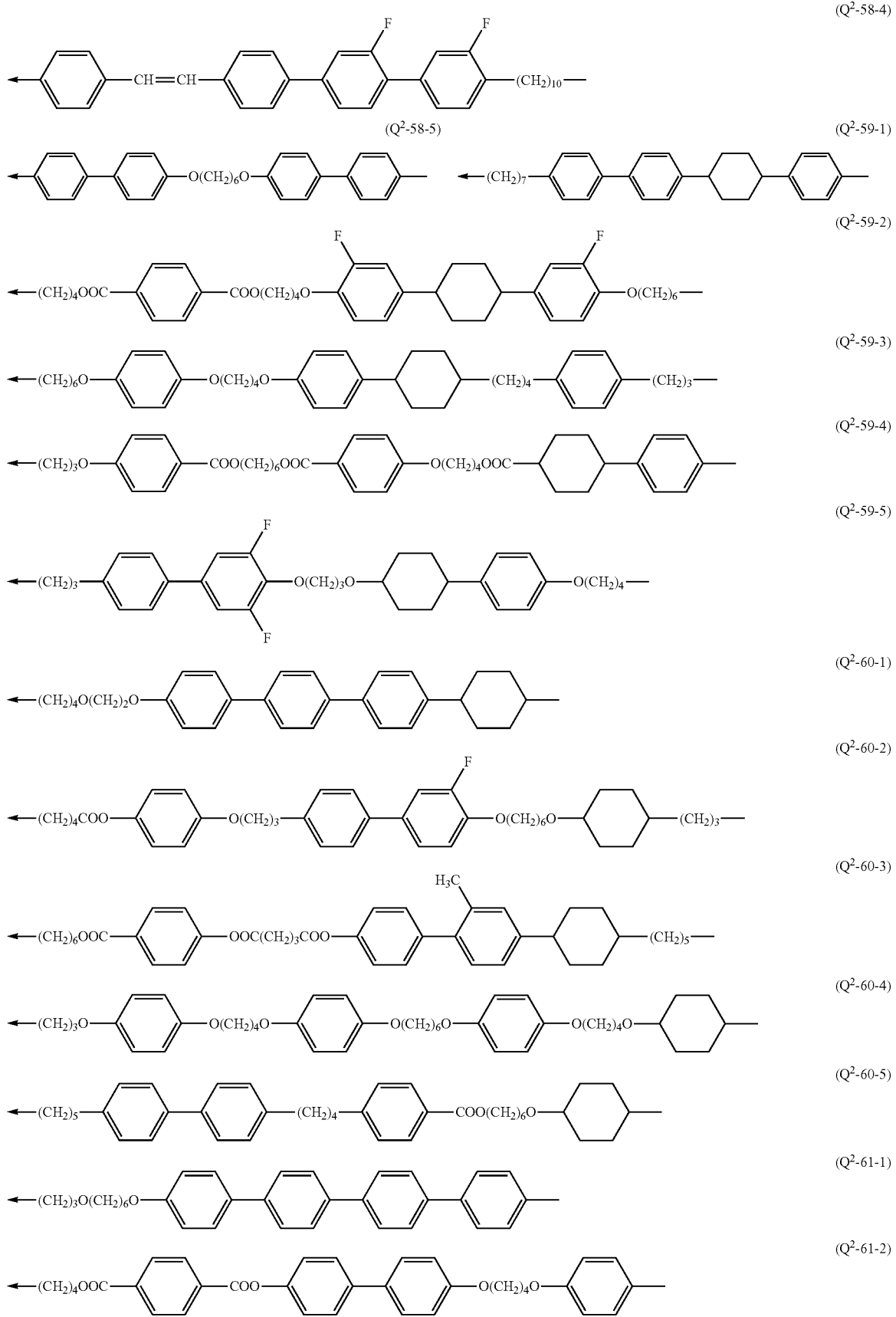

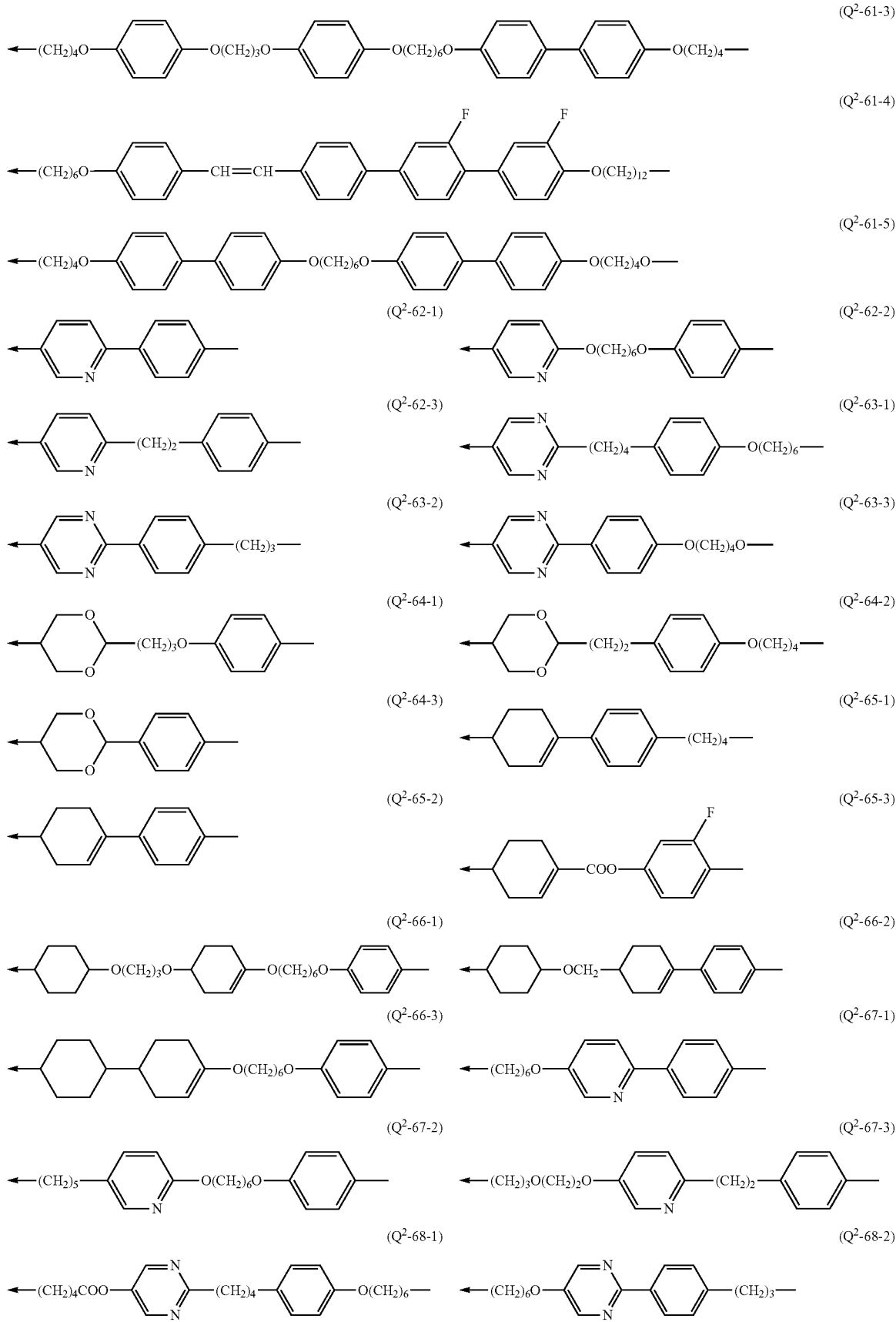

-continued
(Q²-68-3)
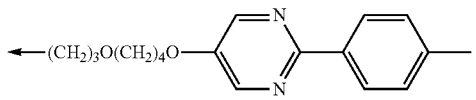
(Q²-69-1)
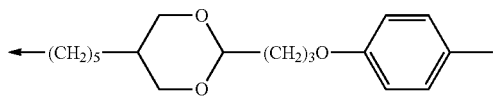
(Q²-69-2)
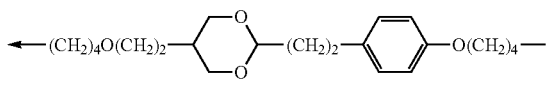
(Q²-69-3)
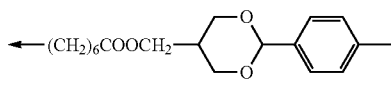
(Q²-70-1)
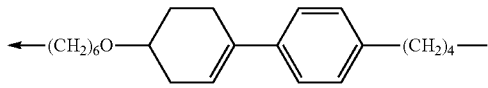
(Q²-70-2)
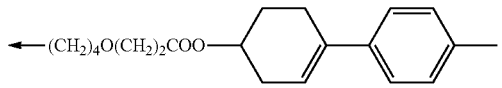
(Q²-70-3)
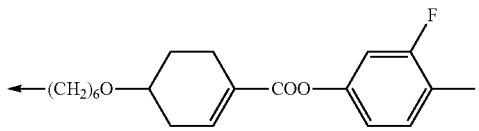
(Q²-71-1)
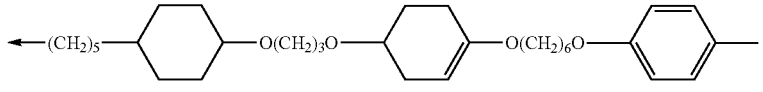
(Q²-71-2)
(Q²-71-3)
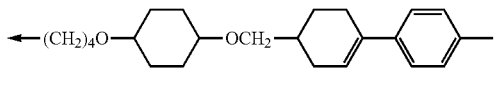
(Q²-72-1)
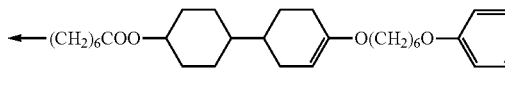
(Q²-72-2)
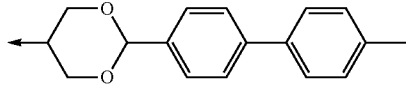
(Q²-72-3)
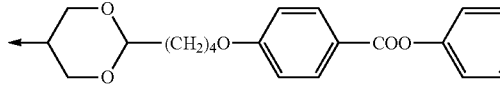
(Q²-73-1)
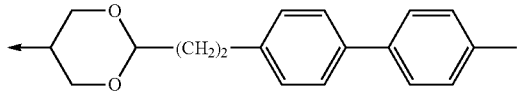
(Q²-73-2)
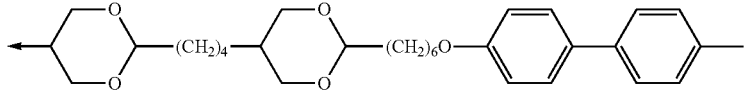
(Q²-73-3)
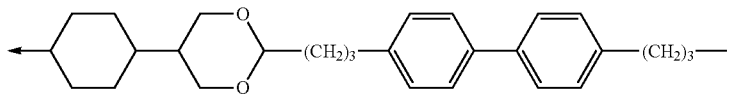
(Q²-74-1)
(Q²-74-2)
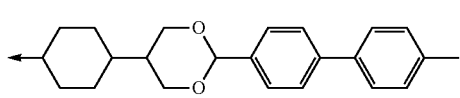
(Q²-74-3)
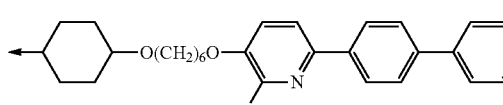
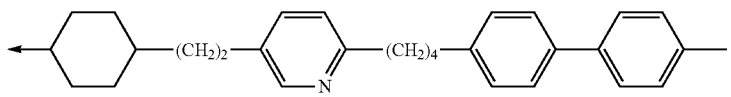
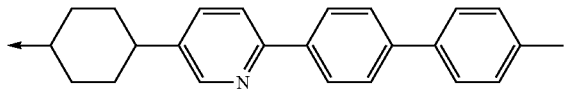

-continued
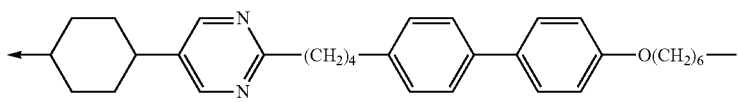 (Q²-75-1)
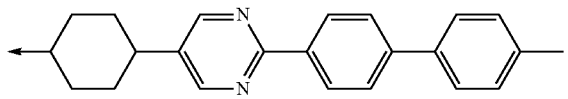 (Q²-75-2)
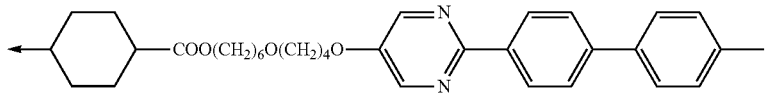 (Q²-75-3)
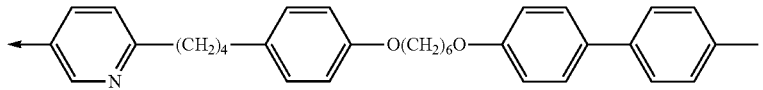 (Q²-76-1)
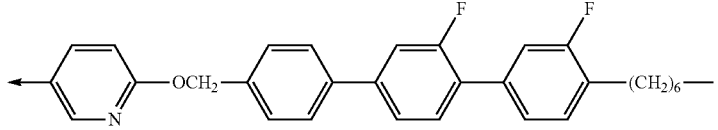 (Q²-76-2)
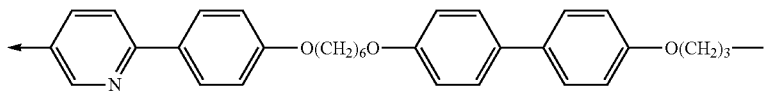 (Q²-76-3)
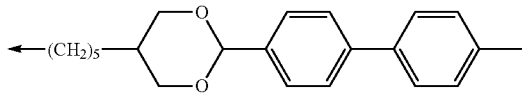 (Q²-77-1)
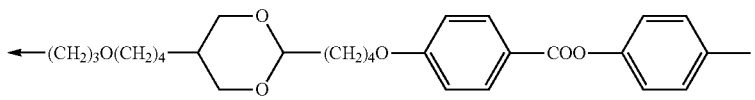 (Q²-77-2)
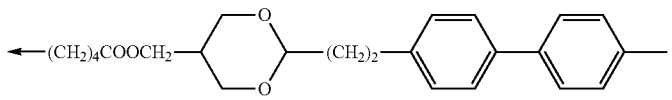 (Q²-77-3)
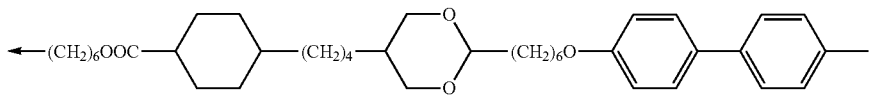 (Q²-78-1)
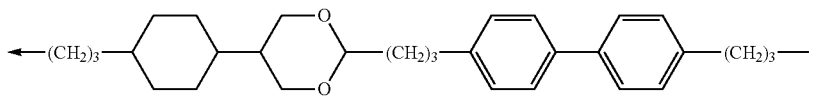 (Q²-78-2)
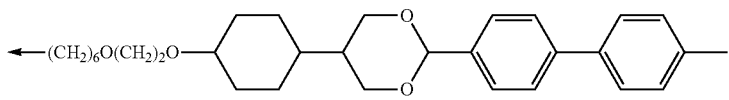 (Q²-78-3)
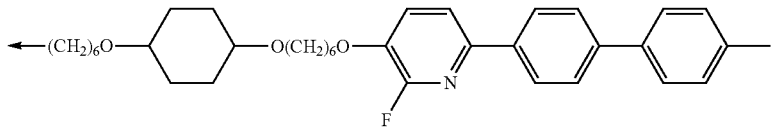 (Q²-79-1)

-continued
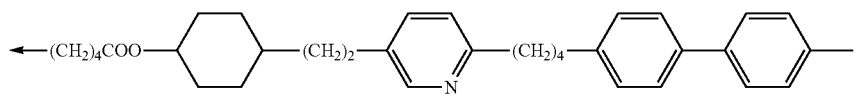
(Q²-79-2)
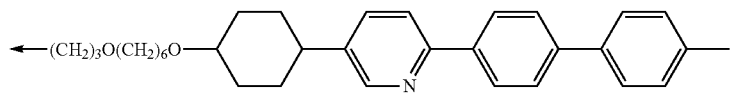
(Q²-79-3)
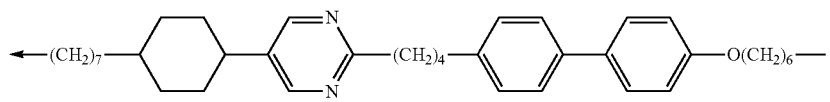
(Q²-80-1)
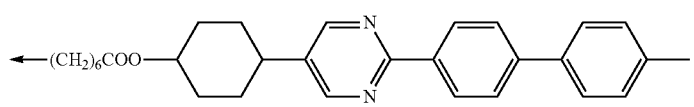
(Q²-80-2)
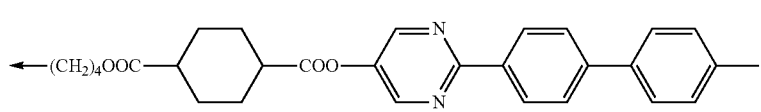
(Q²-80-3)
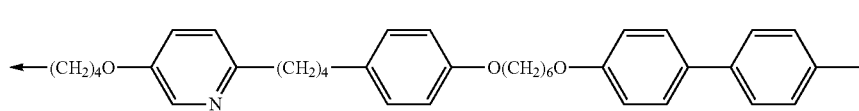
(Q²-81-1)
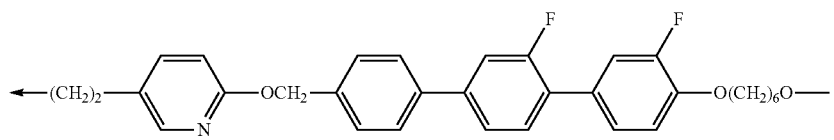
(Q²-81-2)
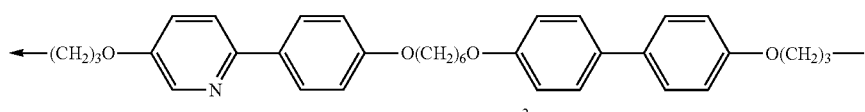
(Q²-81-3)
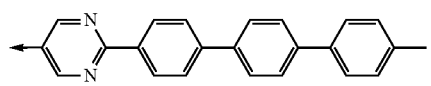
(Q²-82-1)
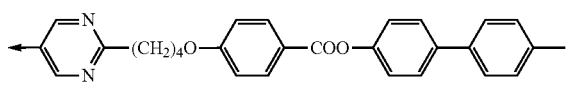
(Q²-82-2)
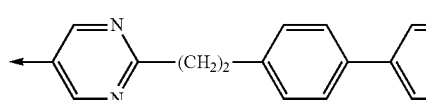
(Q²-82-3)
(Q²-83-1)
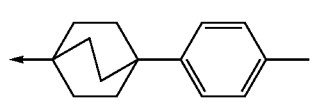
(Q²-83-2)
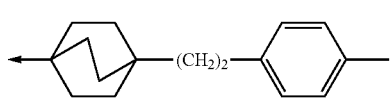
(Q²-84-1)
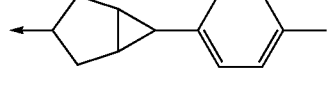
(Q²-84-2)
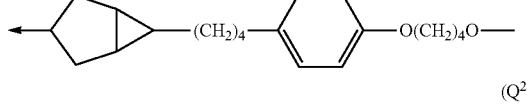
(Q²-85-1)
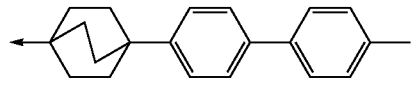
(Q²-85-2)
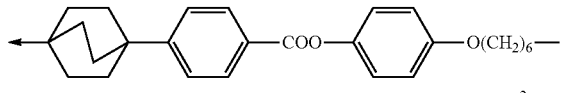
(Q²-86-1)
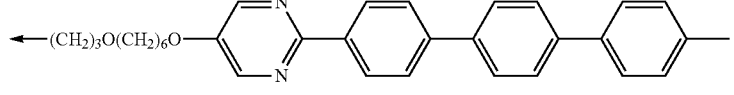

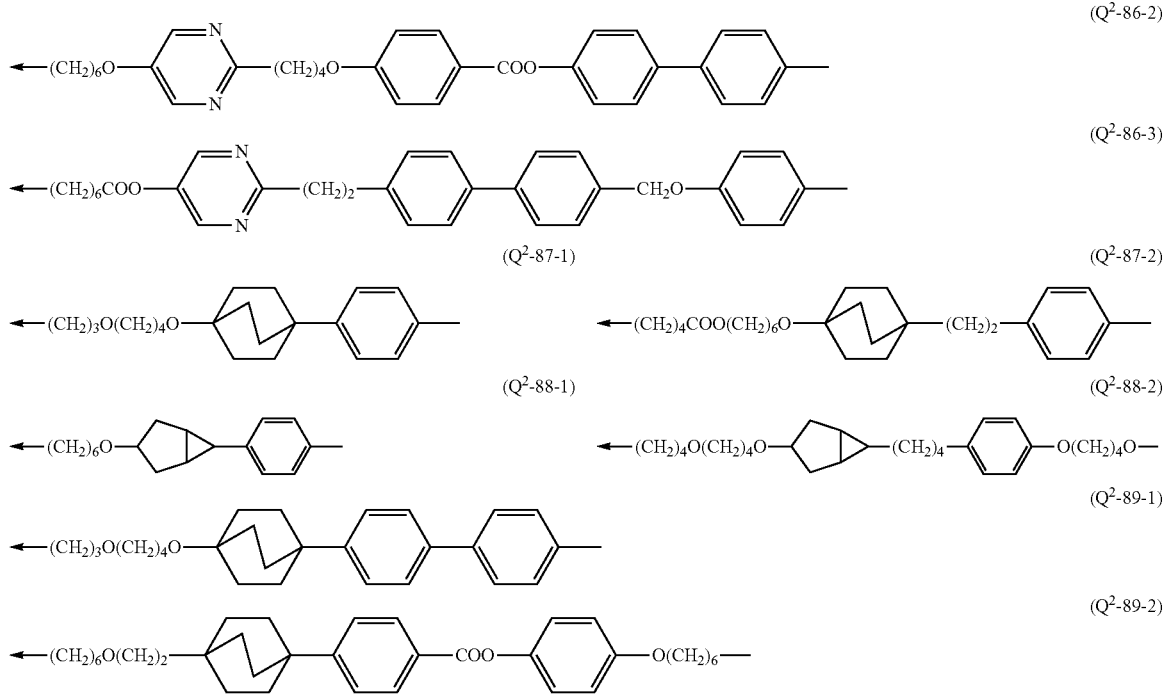

Comparative Example 1

Production 1 of Polyamic Acid

An NMP (45 g) solution of 4,4'-diaminodiphenyl ether (2.39 g) was cooled under nitrogen atmosphere. Pyromellitic dianhydride (2.61 g) was added to the above solution while maintaining the temperature of the reaction system in a range of 5 to 70° C. Then, the solution was stirred for 20 hours to obtain a polyamic acid vanish (50 g) having a polymer concentration of 10% by weight. Polyamic acid contained in the above vanish is named PA acid 1.

Example 7

Production 2 of Polyamic Acid

A polyamic acid vanish (15 g) having a polymer concentration of 20% by weight was obtained in the same manner as in Comparative Example 1, except that pyromellitic dianhydride was changed to Compound (1-1-4) (1.49 g) and 4,4'-diaminodiphenyl ether was changed to Compound (1-3-7) (1.51 g) and that a use amount of NMP was changed to 12 g. Polyamic acid contained in the above vanish is named PA acid 2.

Example 8

Production 3 of Polyamic Acid

A polyamic acid vanish (15 g) having a polymer Concentration of 20% by weight was obtained in the same manner as in Example 7, except that Compound (1-1-4) was changed to pyromellitic dianhydride (0.39 g) and that a use amount of Compound (1-3-7) was changed to 2.61 g. Polyamic acid contained in the above vanish is named PA acid 3.

Example 9

Production 4 of Polyamic Acid

A polyamic acid vanish (10 g) having a polymer concentration of 30% by weight was obtained in the same manner as in Example 7, except that a use amount of Compound (1-1-4) was changed to 2.63 g and Compound (1-3-7) was changed to 4,4'-diaminodiphenyl ether (0.38 g) and that a use amount of NMP was changed to 7 g. Polyamic acid contained in the above vanish is named PA acid 4.

Example 10

The respective vanishes of PA acid 1 to PA acid 4 were diluted to suitable concentrations by butyl cellosolve and coated on a glass substrate by means of a spinner. It was pre-baked at 80° C. for about 5 minutes and then subjected to heat treatment at 220° C. for 30 minutes and then at 300° C. for 60 minutes to form the respective polyimide thin films. These polyimide thin films are designated as PI-1, PI-2, PI-3 and PI-4. PI-1 to PI-4 were measured for physical properties, and the results thereof are shown in Table 29.

Example 11

Production of Polyester

Two drops of titanium triisopropoxide were added to a mixture of Compound (1-1-2) (3.12 g, 2.25 mmol) and butanediol (0.40 g, 4.44 mmol) under nitrogen atmosphere, and the solution was heated and stirred at 220° C. for one hour. After cooling, the content was taken out to obtain 1.91 g of a polyester.

Example 12

A part of the polyester obtained in Example 11 was completely dissolved in NMP (9 g), and this solution was diluted to a suitable concentration by butyl cellosolve and coated on a glass substrate by means of a spinner. It was pre-dried at 80° C. for about 5 minutes and then subjected to heat treatment at 100° C. for one hour and then at 220° C. for 3 hours to obtain a polyester thin film PE-1. PE-1 was measured for physical properties, and the results thereof are shown in Table 29.

TABLE 29

|  | PI-1 | PI-2 | PI-3 | PI-4 | PE-1 |
|---|---|---|---|---|---|
| Pencil hardness | 3H | 2H | 2H | 2H | HB |
| Refractive index | >1.710 | 1.599 | 1.601 | 1.556 | 1.58 |
| Light transmittance (%) | 49 | 91.2 | 87.5 | 95.8 | 99.6 |
| Surface free energy | 40.4 | 31.7 | 31.9 | 29.8 | 31.6 |
| Thermal cracking-starting temperature (° C.) | 182 | 375 | 360 | 377 | 366 |
| 5% weight-reducing temperature (° C.) | 199 | 438 | 460 | 448 | 387 |
| 10% weight-reducing temperature (° C.) | 231 | 502 | 518 | 496 | 413 |

(Remark 1): the light transmittance is a value measured at 400 nm.
(Remark 2): the unit of the surface free energy is erg/cm$^2$.

Example 13

The polyester (0.26 g) obtained in Example 11 was pressed by means of a pressing machine (upper face, lower face temperature: 260° C., press pressure: 19.6 MPa) to obtain a polyester substrate having an average thickness of 244 μm.

Comparative Example 2

Production 1 of Epoxy Resin

Bisphenol A glycidyl ether (brand name: EPICLON 850S, manufactured by Dainippon Ink & Chemicals Inc.) (0.3 g) and 4,4'-diaminodiphenyl ether (0.176 g) were dissolved in NMP (1.11 g) to obtain an epoxy compound solution having a compound concentration of 30% by weight. This solution was coated on a copper foil, pre-baked at 80° C. for about 30 minutes and then subjected to heat treatment at 220° C. for 60 minutes and then at 220° C. for 60 minutes under reduced pressure, and it was subjected to etching treatment to obtain an epoxy resin film having a thickness of about 40 μm. The above film had an average light transmittance of 65.2% in 400 to 800 nm, and a wavelength in which the light transmittance was less than 1% was 345 nm.

Example 14

Production 2 of Epoxy Resin

An epoxy compound solution having a compound concentration of 30% by weight was obtained in the same manner as in Comparative Example 2, except that EPICLON 850S was changed to Compound (1-1-5) (1.0 g) and a use amount of 4,4'-diaminodiphenyl ether was changed to 0.145 g and that a use amount of NMP was changed to 2.67 g. The above solution was treated in the same manner as in Comparative Example 2 to obtain an epoxy resin film having a thickness of about 100 μm. This film had an average light transmittance of 81.4% in 400 to 800 nm, and a wavelength in which the light transmittance was less than 1% was 260 nm. That is, it is apparent that a PSQ skeleton can be introduced into the epoxy resin without adding polysiloxane and that the resulting coat-ing film is improved in transparency as compared with the coating film prepared in Comparative Example 2.

INDUSTRIAL APPLICABILITY

The compound of the present invention has a good compatibility with other compounds and polymers, and can readily provide a polymer of a high molecular weight having a silsesquioxane skeleton in a principal chain and/or side chains by homopolymerization or copolymerization. The polymer is excellent in characteristics such as mechanical strength, coating property, compatibility, transparency, heat resistance, water repellency and electrical insulating property. The polymer can be used for a coating agent, a plastic substrate and an optical material.

What is claimed is:

1. A polymer having a structural unit represented by Formula (3):

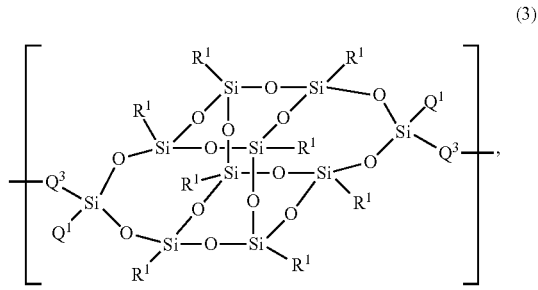

wherein $R^1$ is phenyl in which any hydrogen may be replaced by halogen or alkyl having 1 to 5 carbon atoms; in the alkyl having 1 to 5 carbon atoms, any —CH$_2$—, which is not adjacent to each other, may be replaced by —O—, and any hydrogen may be replaced by halogen; $Q^1$ is hydrogen, halogen, alkyl having 1 to 10 carbon atoms, cyclopropyl, cyclobutyl, cyclopentyl, cyclohexyl, cyclohexenyl, or phenyl in which any hydrogen may be replaced by halogen or alkyl having 1 to 5 carbon atoms; in the alkyl having 1 to 10 carbon atoms and alkyl having 1 to 5 carbon atoms which is a substituent of phenyl, any —CH$_2$—, which is not adjacent to each other, may be replaced by —O—, —CH=CH— or —C≡C—, and any hydrogen may be replaced by halogen; and $Q^3$ is a group represented by Formula (4):

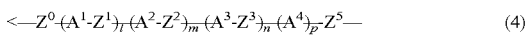

wherein a code < represents a bonding point with silicon; l, m, n and p are independently 0, 1, 2 or 3; $A^1$, $A^2$, $A^3$ and $A^4$ are independently a single bond, 1,4-cyclohexylene, 1,4-cyclohexenylene, a condensed ring group having 6 to 10 carbon atoms which is a divalent group, or 1,4-phenylene; in these rings, any —CH$_2$—, which is not adjacent to each other, may be replaced by —O—, and any —CH= may be replaced by —N=; any hydrogen in all rings may be replaced by halogen, —CN, —NO$_2$ or alkyl having 1 to 5 carbon atoms; in the alkyl having 1 to 5 carbon atoms, any —CH$_2$—, which is not adjacent to each other, may be replaced by —O—, —CH=CH— or —C≡C—, and any hydrogen may be replaced by halogen; $Z^0$, $Z^1$, $Z^2$ and $Z^3$ are independently a single bond, —CH=CH—, —C≡C—, —COO—, —OCO— or alkylene in which the number of carbon atoms is 1 to 20 and any —CH$_2$— may be replaced by —O—, —S—, —NH—, —SiR$^2_2$—, —SiR$^2_2$O—, —OSiR$^2_2$—, —OSiR²₂O—, —SiR²₂OSiR²₂—, —COO—, —OCO—, —CH=CH— or —C≡C—; R² is halogen, alkyl having 1 to 10 carbon atoms, cyclopropyl, cyclobutyl, cyclopentyl, cyclohexyl, cyclohexenyl, or phenyl in which any hydrogen may be replaced by halogen or alkyl having 1 to 5 carbon atoms; in the alkyl having 1 to 10 carbon atoms and alkyl having 1 to 5 carbon atoms which is a substituent of phenyl, any —CH₂—, which is not adjacent to each other, may be replaced by —O—, —CH=CH— or —C≡C—, and any hydrogen may be replaced by halogen; $Z^5$ is a single bond, —CH=CH—, —C≡C—, —COO—, —OCO— or a group represented by —$W^1$-$T^1$-; $W^1$ is a single bond or alkylene in which the number of carbon atoms is 1 to 20 and any —CH₂—, which is not adjacent to each other, may be replaced by —O—, —COO—, —OCO—, —CH=CH— or —C≡C—; and $T^1$ is —O—, —S—, —SiR²₂—, —SiR²₂O—, —OSiR²₂—, —OSiR²₂O—, —SiR²₂OSiR²₂—, —CO—, —COO—, —OCO—, —CSO—, —OCS—, —CONR¹⁰—, —NR¹⁰CO—, —CONR¹⁰O—, —ONR¹⁰CO—, —OCONR¹⁰—, —NR¹⁰CONR¹⁰—, —NR¹⁰COO—, —OCOO—, —CH(OH)CH₂—, —CH₂CH(OH)—, —CH=CH—, —CH₂CR⁵=CR⁶CH₂—, —C≡C—, —SO₂—, —SO₂O—, —OSO₂—, —SO₂S—, —SSO₂—, —NR¹⁰SO₂—, or any one of groups shown below:

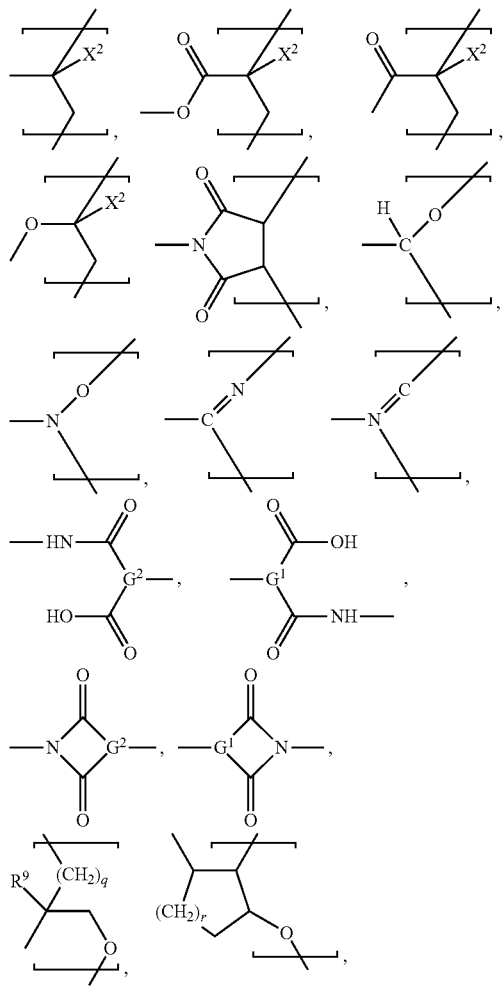

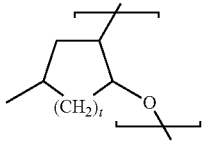

in the groups related to $T^1$, $R^2$ is the same as described above; $R^{10}$ is hydrogen, cyclopropyl, cyclobutyl, cyclopentyl, cyclohexyl, cyclohexenyl, alkyl in which the number of carbon atoms is 1 to 10, and any hydrogen may be replaced by halogen, or phenyl in which any hydrogen may be replaced by halogen or alkyl having 1 to 5 carbon atoms; in the alkyl having 1 to 5 carbon atoms which is a substituent of phenyl, any —CH₂—, which is not adjacent to each other, may be replaced by —O—, —CH=CH— or —C≡C—, and any hydrogen may be replaced by halogen; $R^5$, $R^6$ and $X^2$ are independently hydrogen, halogen, —CN or alkyl in which the number of carbon atoms is 1 to 10, any —CH₂—, which is not adjacent to each other, may be replaced by —O—, and any hydrogen may be replaced by halogen; $G^1$ is a trivalent organic group; $G^2$ is a part of tricarboxylic acid-derivative's residue or a part of tetracarboxylic acid-derivative's residue; $R^9$ is hydrogen or alkyl having 1 to 5 carbon atoms; q is 1 or 0; r is an integer of 0 to 5; and t is an integer of 1 to 5.

2. The polymer according to claim 1, wherein $R^1$ is phenyl in which any hydrogen may be replaced by fluorine or chlorine.

3. The polymer according to claim 1, wherein $R^1$ is phenyl in which any hydrogen may be replaced by fluorine or chlorine; $Q^1$ is cyclopropyl, cyclobutyl, cyclopentyl, cyclohexyl, alkyl in which the number of carbon atoms is 1 to 10 and any hydrogen may be replaced by fluorine, or phenyl in which any hydrogen may be replaced by fluorine, chlorine or alkyl having 1 to 5 carbon atoms; and in the alkyl having 1 to 5 carbon atoms which is a substituent of phenyl, any —CH₂—, which is not adjacent to each other, may be replaced by —O—, and any hydrogen may be replaced by fluorine.

4. The polymer according to claim 1, wherein $R^1$ is phenyl in which any hydrogen may be replaced by fluorine or chlorine; $Q^1$ is cyclopropyl, cyclobutyl, cyclopentyl, cyclohexyl, alkyl in which the number of carbon atoms is 1 to 10 and any hydrogen may be replaced by fluorine, or phenyl in which any hydrogen may be replaced by fluorine, chlorine or alkyl having 1 to 5 carbon atoms; in the alkyl having 1 to 5 carbon atoms which is a substituent of phenyl, any —CH₂—, which is not adjacent to each other, may be replaced by —O—, and any hydrogen may be replaced by fluorine; $A^1$, $A^2$, $A^3$ and $A^4$ are independently a single bond, 1,4-cyclohexylene, 1,4-cyclohexenylene, 1,4-phenylene or a condensed ring group having 6 to 10 carbon atoms which is a divalent group; in these rings, any hydrogen may be replaced by fluorine, chlorine or alkyl having 1 to 5 carbon atoms; in the alkyl having 1 to 5 carbon atoms, any —CH₂—, which is not adjacent to each other, may be replaced by —O—, and any hydrogen may be replaced by fluorine; $Z^0$, $Z^1$, $Z^2$ and $Z^3$ are independently a single bond, —CH=CH—, —C≡C—, —COO—, —OCO— or alkylene in which the number of carbon atoms is 1 to 20 and any —CH₂—, which is not adjacent to each other, may be replaced by —O—, —NH—, —SiR²₂—, —SiR²₂O—, —OSiR²₂—, —SiR²₂OSiR²₂—, —COO—, —OCO—, —CH=CH— or —C≡C—; $R^2$ is halogen, cyclopropyl, cyclobutyl, cyclopentyl, cyclohexyl, alkyl in which the number of carbon atoms is 1 to 10 and any hydrogen may be replaced by fluorine, or phenyl in which any hydrogen may be replaced by fluorine, chlorine or alkyl having 1 to 5 carbon atoms; in the alkyl having 1 to 5 carbon atoms which is a substituent of phenyl, any —CH$_2$—, which is not adjacent to each other, may be replaced by —O—, and any hydrogen may be replaced by fluorine; $Z^5$ is a single bond, —CH=CH—, —C≡C—, —COO—, —OCO— or a group represented by —W$^1$-T$^1$; W$^1$ is a single bond or alkylene in which the number of carbon atoms is 1 to 20 and any —CH$_2$—, which is not adjacent to each other, may be replaced by —O—, —COO—, —OCO—, —CH=CH— or —C≡C—; and T$^1$ is —O—, —COO—, —OCO—, —CONR$^{10}$—, —NR$^{10}$CO—, —OCOO—, —CH(OH)CH$_2$—, —CH$_2$CH(OH)—, —CH=CH—, —C≡C—, —SO$_2$—, or any one of groups shown below:

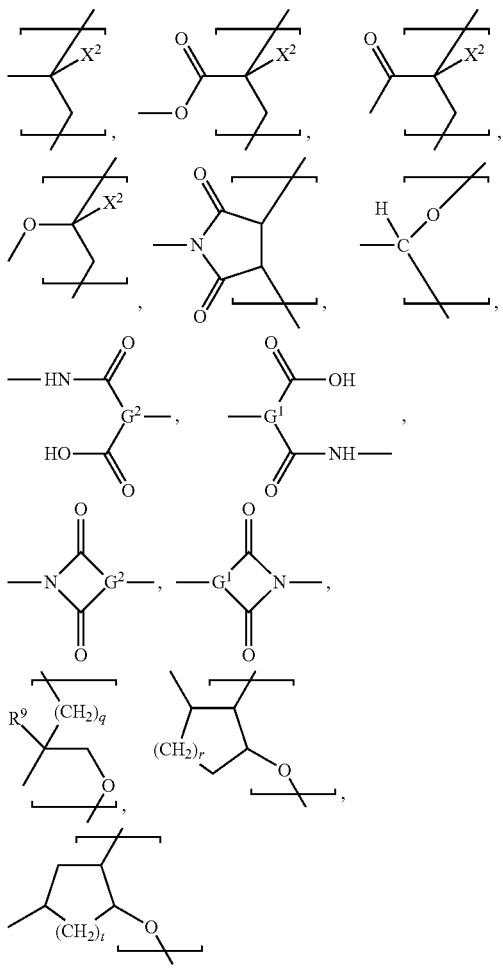

in these groups related to T$^1$, R$^{10}$ is hydrogen, cyclopentyl, cyclohexyl, alkyl in which the number of carbon atoms is 1 to 5 and any hydrogen may be replaced by fluorine, or phenyl in which any hydrogen may be replaced by fluorine, chlorine or alkyl having 1 to 5 carbon atoms; in the alkyl having 1 to 5 carbon atoms which is a substituent of phenyl, any —CH$_2$—, which is not adjacent to each other, may be replaced by —O—, and any hydrogen may be replaced by fluorine; X$^2$ is hydrogen, fluorine, chlorine or alkyl in which the number of carbon atoms is 1 to 5, any —CH$_2$—, which is not adjacent to each other, may be replaced by —O— and any hydrogen may be replaced by fluorine; G$^1$ is a trivalent organic group; G$^2$ is a part of tricarboxylic acid-derivative's residue or a part of tetracarboxylic acid-derivative's residue; R$^9$ is hydrogen, methyl or ethyl; q is 1 or 0; r is an integer of 0 to 5; and t is an integer of 1 to 5.

5. The polymer according to claim 4, wherein R$^1$ is phenyl.

6. The polymer according to claim 4, wherein R$^1$ is phenyl; Q$^1$ is cyclopentyl, cyclohexyl, alkyl in which the number of carbon atoms is 1 to 5 and any hydrogen may be replaced by fluorine, or phenyl in which any hydrogen may be replaced by fluorine or alkyl having 1 to 5 carbon atoms; and in the alkyl having 1 to 5 carbon atoms which is a substituent of phenyl, any —CH$_2$—, which is not adjacent to each other, may be replaced by —O—, and any hydrogen may be replaced by fluorine.

7. The polymer according to claim 4, wherein R$^1$ is phenyl; Q$^1$ is cyclopentyl, cyclohexyl, alkyl having 1 to 5 carbon atoms, or phenyl in which any hydrogen may be replaced by fluorine or alkyl having 1 to 5 carbon atoms; in the alkyl having 1 to 5 carbon atoms which is a substituent of phenyl, any —CH$_2$—, which is not adjacent to each other, may be replaced by —O—, and any hydrogen may be replaced by fluorine; A$^1$, A$^2$, A$^3$ and A$^4$ are independently a single bond or 1,4-phenylene in which any hydrogen may be replaced by fluorine, chlorine or alkyl having 1 to 5 carbon atoms; in the alkyl having 1 to 5 carbon atoms which is a substituent of 1,4-phenylene, any —CH$_2$—, which is not adjacent to each other, may be replaced by —O—, and any hydrogen may be replaced by fluorine; Z$^0$, Z$^1$, Z$^2$ and Z$^3$ are independently a single bond, —COO—, —OCO— or alkylene in which the number of carbon atoms is 1 to 20 and any —CH$_2$—, which is not adjacent to each other, may be replaced by —O—, —COO— or —OCO—; Z$^5$ is a single bond, —COO—, —OCO— or a group represented by —W$^1$-T$^1$; W$^1$ is a single bond or alkylene in which the number of carbon atoms is 1 to 20 and any —CH$_2$—, which is not adjacent to each other, may be replaced by —O—, —COO— or —OCO—; and T$^1$ is —O—, —COO—, —OCO—, —CONR$^{10}$—, —NR$^{10}$CO—, or any one of groups shown below:

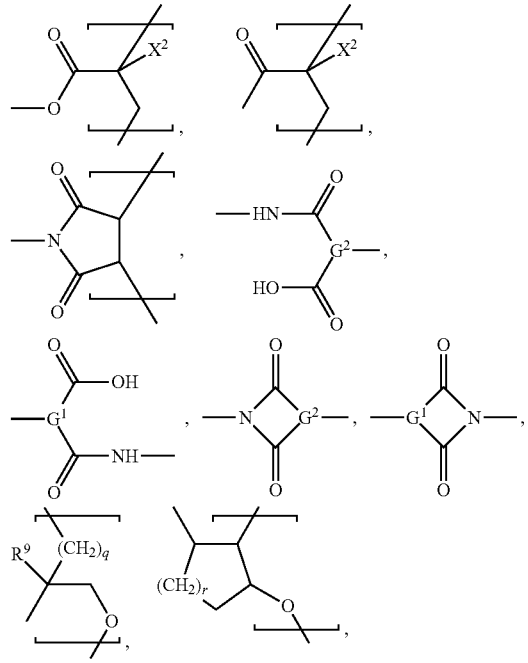

-continued

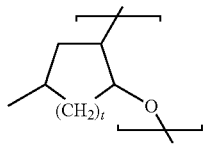

in these groups related to $T^1$, $R^{10}$ is hydrogen, alkyl having 1 to 5 carbon atoms, or phenyl; $X^2$ is hydrogen, fluorine or alkyl having 1 to 5 carbon atoms; $G^1$ is a trivalent organic group; $G^2$ is a part of tricarboxylic acid-derivative's residue or a part of tetracarboxylic acid-derivative's residue; $R^9$ is hydrogen, methyl or ethyl; q is 1 or 0; r is an integer of 0 to 5; and t is an integer of 1 to 5.

8. The polymer according to claim 7, wherein $Q^1$ is methyl or phenyl.

9. The polymer according to claim 7, wherein $Q^1$ is methyl or phenyl; $A^1$, $A^2$, $A^3$ and $A^4$ are independently a single bond or 1,4-phenylene; $Z^0$, $Z^1$, $Z^2$ and $Z^3$ are independently a single bond, —COO—, —OCO— or alkylene in which the number of carbon atoms is 1 to 20 and any —CH$_2$—, which is not adjacent to each other, may be replaced by —O—, —COO— or —OCO—; $Z^5$ is a single bond, —COO—, —OCO— or a group represented by —$W^1$-$T^1$; $W^1$ is a single bond or alkylene in which the number of carbon atoms is 1 to 20 and any —CH$_2$—, which is not adjacent to each other, may be replaced by —O—, —COO— or —OCO—; and $T^1$ is —O—, —COO—, —OCO—, —CONR$^{10}$—, —NR$^{10}$CO—, or any one of groups shown below:

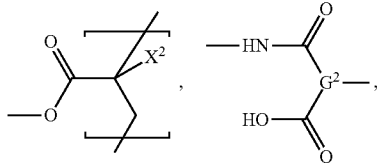

-continued

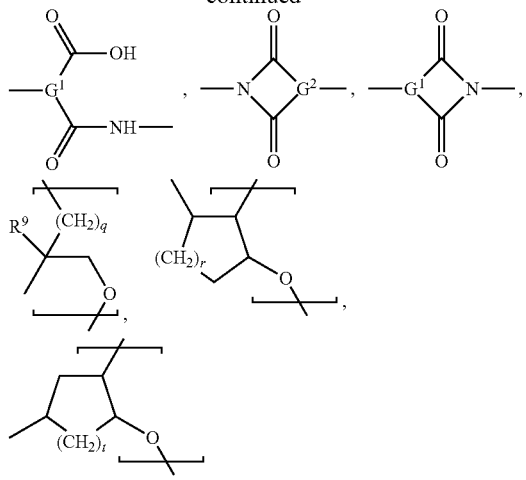

in these groups related to $T^1$, $R^{10}$ is hydrogen or methyl; $X^2$ is hydrogen or methyl; $G^1$ is a trivalent organic group; $G^2$ is a part of tricarboxylic acid-derivative's residue or a part of tetracarboxylic acid-derivative's residue; $R^9$ is hydrogen, methyl or ethyl; q is 1 or 0; r is an integer of 0 to 5; and t is an integer of 1 to 5.

10. The polymer according to claim 9, wherein $T^1$ is —O—, —COO—, —OCO—, —CONR$^{10}$—, —NR$^{10}$CO—, or any one of groups shown below:

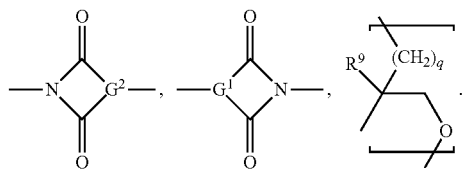

* * * * *